(12) United States Patent
Crawford et al.

(10) Patent No.: US 12,286,398 B2
(45) Date of Patent: Apr. 29, 2025

(54) ANTI-BACTERIAL STILBENE DERIVATIVES AND METHODS OF USE

(71) Applicant: YALE UNIVERSITY, New Haven, CT (US)

(72) Inventors: Jason Crawford, Shelton, CT (US); Tyler Goddard, Cambridge, MA (US); Hyun Bong Park, West Haven, CT (US); Jaymin Patel, New Haven, CT (US)

(73) Assignee: Yale University, New Haven, CT (US)

( * ) Notice: Subject to any disclaimer, the term of this patent is extended or adjusted under 35 U.S.C. 154(b) by 786 days.

(21) Appl. No.: 17/604,908

(22) PCT Filed: Apr. 17, 2020

(86) PCT No.: PCT/US2020/028841
§ 371 (c)(1),
(2) Date: Oct. 19, 2021

(87) PCT Pub. No.: WO2020/215006
PCT Pub. Date: Oct. 22, 2020

(65) Prior Publication Data
US 2022/0194888 A1    Jun. 23, 2022

Related U.S. Application Data

(60) Provisional application No. 62/969,814, filed on Feb. 4, 2020, provisional application No. 62/836,489, filed on Apr. 19, 2019.

(51) Int. Cl.
*C07C 50/28* (2006.01)
*A01N 35/06* (2006.01)
*A01P 1/00* (2006.01)
*A61K 9/00* (2006.01)
*A61P 31/02* (2006.01)

(52) U.S. Cl.
CPC .............. *C07C 50/28* (2013.01); *A01N 35/06* (2013.01); *A01P 1/00* (2021.08); *A61K 9/0014* (2013.01); *A61P 31/02* (2018.01)

(58) Field of Classification Search
CPC .................................................... C07C 50/28
See application file for complete search history.

(56) References Cited

U.S. PATENT DOCUMENTS

2003/0149003 A1    8/2003  Chaplin
2010/0247462 A1    9/2010  Snyder

OTHER PUBLICATIONS

Crawford, Jason M., Renee Kontnik, and Jon Clardy. "Regulating alternative lifestyles in entomopathogenic bacteria." Current Biology 20.1 (2010): 69-74.

Eleftherianos, Ioannis, et al. "An antibiotic produced by an insect-pathogenic bacterium suppresses host defenses through phenoloxidase inhibition." Proceedings of the National Academy of Sciences 104.7 (2007): 2419-2424.
Hu, Kaiji, et al. "A novel antimicrobial epoxide isolated from larval Galleria mellonella infected by the nematode symbiont, *Photorhabdus luminescens* (Enterobacteriaceae)." Bioorganic & medicinal chemistry 14.13 (2006): 4677-4681.
International Search Report and Written Opinion issued in App. No. PCT/US20/28841, dated Jul. 28, 2020, 7 pages.
Joyce, Susan A., et al. "Bacterial biosynthesis of a multipotent stilbene." Angewandte Chemie-International Edition in English—47.10 (2008): 1942.
Kontnik, Renee, Jason M. Crawford, and Jon Clardy. "Exploiting a global regulator for small molecule discovery in Photorhabdus luminescens." ACS chemical biology 5.7 (2010): 659-665.
Likhitwitayawuid et al., "A New Dimeric Stilbene with Tyrosine Inhibitory Activity from Artocarpus gomezianus", J. Nat. Prod., (20010000), vol. 64, pp. 1457-1459, XP002267827.
Park, Hyun Bong, and Jason M. Crawford. "Lumiquinone A, an α-aminomalonate-derived aminobenzoquinone from Photorhabdus luminescens." Journal of natural products 78.6 (2015): 1437-1441.
Park, Hyun Bong, et al. "Stilbene epoxidation and detoxification in a *Photorhabdus luminescens*—nematode symbiosis." Journal of Biological Chemistry 292.16 (2017): 6680-6694.

(Continued)

*Primary Examiner* — Shawquia Jackson
(74) *Attorney, Agent, or Firm* — Saul Ewing LLP; Domingos Silva

(57) ABSTRACT

Provided herein are novel antibacterial compounds of Formula I. The compounds can be made through enzymatic oxidative dimerization in the presence of a suitable organism and one or more metal salts. Pathogenic bacteria exposed to the compound of Formula I do not develop resistance to these compounds even after prolonged exposure. Also provided herein are methods of treating bacterial infections, and method of killing or disinfecting bacteria.

23 Claims, 27 Drawing Sheets
Specification includes a Sequence Listing.

Formula I

(56) References Cited

OTHER PUBLICATIONS

Perez, Corey E., and Jason M. Crawford. "Characterization of a hybrid nonribosomal peptide-carbohydrate biosynthetic pathway in Photorhabdus luminescens." Biochemistry 58.8 (2019): 1131-1140.
Shi, Danshu, et al. "Stilbene derivatives from Photorhabdus temperata SN259 and their antifungal activities against phytopathogenic fungi." Journal of agricultural and food chemistry 65.1 (2017): 60-65.
Shi, Yi-Ming, and Helge B. Bode. "Chemical language and warfare of bacterial natural products in bacteria-nematode-insect interactions." Natural product reports 35.4 (2018): 309-335.
Somvanshi, Vishal S., et al. "A single promoter inversion switches Photorhabdus between pathogenic and mutualistic states." Science 337.6090 (2012): 88-93.
Vizcaino, Maria I., Xun Guo, and Jason M. Crawford. "Merging chemical ecology with bacterial genome mining for secondary metabolite discovery." Journal of Industrial Microbiology and Biotechnology 41.2 (2014): 285-299.
Wu et al., "New Chalcone and Dimeric Chalcones with 1,4-p-benzoquinone Residue from Combretum yunnanense", Planta Med., (20110000), vol. 77, doi: 10.1055/s-0030-1250492, pp. 481-484, XP018500709.
Zong, Yao, et al. "Computational design and synthesis of novel fluoro-analogs of combretastatins A-4 and A-1." Journal of fluorine chemistry 203 (2017): 193-199.

C

ANTI-BACTERIAL STILBENE DERIVATIVES AND METHODS OF USE

CROSS-REFERENCE TO RELATED APPLICATIONS

The present application is a 35 U.S.C. § 371 national phase application from, and claims priority to, International Application No. PCT/US2020/028841 filed Apr. 17, 2020, which claims priority to U.S. Provisional Patent Application Ser. No. 62/836,489 entitled "ANTI-BACTERIAL STILBENE DERIVATIVES AND METHODS OF USE," filed Apr. 19, 2019, and U.S. Provisional Patent Application Ser. No. 62/969,814 entitled "ANTI-BACTERIAL STILBENE DERIVATIVES AND METHODS OF USE," filed Feb. 4, 2020, the disclosures of all of which are incorporated herein by reference in their entireties.

STATEMENT REGARDING FEDERALLY SPONSORED RESEARCH

This invention was made with government support under grant nos. CA186575 and GM097096, awarded by National Institutes of Health. The government has certain rights in this invention.

SEQUENCE LISTING

The present application contains a Sequence Listing that has been submitted in ASCII format via EFS-Web and is hereby incorporated by reference in its entirety. The ASCII copy, created Apr. 17, 2020, is named 047162-7217WO1_Seq_Listing.txt and is 1 kilobytes in size

BACKGROUND

Psoriasis is a chronic autoimmune disease of the skin, and the microbial consortia on our skin and even in our gut contribute to disease severity. Patients with psoriasis have a higher risk of other inflammatory diseases, including psoriatic arthritis, diabetes, inflammatory bowel disease (IBD), and Parkinson's disease. There is a growing understanding of the genetic and molecular bases of psoriasis; however, the disease is currently incurable and its incidence continues to rise, affecting more than 125 million people worldwide.

Common small molecule drugs, including topical corticosteroids, immuno-suppressants such as methotrexate and cyclosporine, and biologics for treating psoriasis can have unintended side effects that vary in a patient-dependent manner, such as skin thinning, skin cancer, lymphoma, and dysfunction of the immune system. Accordingly, there is a need for new small molecule drugs to extend the therapeutic arsenal for psoriasis treatments and for a better understanding of both the structural and functional drug transformations that take place.

Tapinarof (1) is a topical non-steroidal anti-inflammatory drug (NSAID) that is currently in phase 3 clinical trials to treat psoriasis and atopic dermatitis. Tapinarof is an isopropyl-substituted stilbene metabolite produced by members of the gammaproteobacterial *Photorhabdus* genus. Recent studies demonstrated that tapinarof activates the arylhydrocarbon receptor (AhR) signaling program in both human skin cells and mouse models, which largely accounts for the drug's clinical efficacy. The AhR is a conserved ligand-dependent transcription factor and is thought to be a key regulator involved in the metabolism of drugs, xenobiotics, and endogenous small molecules. However, it has become clear that the AhR pathway plays important roles in immune signaling in various cell types. Tapinarof has also been shown to activate the nuclear factor erythroid 2-related factor 2 (Nrf2) antioxidant signaling pathway involved in the cellular defense of reactive oxygen species (ROS) and electrophilic cell stress, which is also thought to in part contribute to the drug's clinical efficacy.

Natural stilbenes (i.e., compounds having a 1,2-diphenylethylene core), including the dietary supplement resveratrol, are a vast class of phenylpropanoid polyketides commonly found in dietary plants (e.g., grapes, peanuts, blueberries, and others). Plant stilbenes have been used as alternative therapies in the treatment of IBDs and are known to access the bloodstream. However, clinical trials for IBDs ultimately failed due to inter-individual clinical variability. In these studies, the structural and functional biotransformations mediated by the microbiome were not considered, and it is now well known that microbiome composition can affect clinical responses to drugs and vary dramatically among patients. These plant-derived stilbenes are constructed by stilbene synthase (STS), a member of the type III polyketide synthase (PKS) superfamily. Modifications of stilbene monomers, including glycosylation, prenylation, dimerization, and polymerization, result in enormous overall chemical complexity. Even modest structural modifications can dramatically alter their biological functions. Intriguingly, *Photorhabdus* is a rare bacterial stilbene producer that convergently evolved an atypical type II PKS route for their biosynthesis, suggesting a selective pressure to generate "plant-type" stilbenes in their ecological niche.

*Photorhabdus* members are endosymbionts of parasitic nematodes that typically infect diverse insect larvae (entomopathogens). *Photorhabdus asymbiotica* is a pathogen of both insects and humans, whereas *Photorhabdus luminescens* is limited to insect hosts. *P. asymbiotica* causes severe soft tissue infections of the skin and systemic infections of the bloodstream. Clinical diagnoses of *P. asymbiotica* infections have largely occurred in the United States and Australia, although this emerging pathogen is now being recognized worldwide. The bacteria engage in stochastic phase variation P-form and M-form to adapt to this multipartite lifecycle, which is regulated by an ON/OFF invertible promoter switch. The pathogenic P-form produces diverse secondary metabolites to modulate the host immune system, promote nematode development, kill microbial competitors, and manage immune-associated oxidative cell stress. However, the small colony variant M-form colonizes specific cells in the host nematode intestinal tract to facilitate vertical transmission to nematode progeny. Tapinarof and related analogs are produced in the P-form and contribute to innate immunosuppression, nematode development, and antioxidant defense. The metabolites also exhibit some activity against fungi and Gram-positive bacteria.

Due to the widespread use of antibiotics, antibiotic resistance is large public health problem. Antibiotic resistance is rising to dangerously high levels in all parts of the world. New resistance mechanisms are emerging and spreading globally, threatening the ability of medical professionals to treat common infectious diseases. A growing list of infections—such as pneumonia, tuberculosis, blood poisoning, gonorrhea, and foodborne diseases—are becoming harder, and sometimes impossible, to treat as antibiotics become less effective.

Where antibiotics can be bought for human or animal use without a prescription, the emergence and spread of resistance is made worse. Similarly, in countries without standard treatment guidelines, antibiotics are often over-prescribed by health workers and veterinarians and over-used by the public.

There is therefore a need to develop new antibiotics to treat resistant bacteria and/or to develop antibiotics to which bacteria have difficulty developing resistance to. The present invention addresses this need.

BRIEF SUMMARY OF THE INVENTION

In some embodiments, this disclosure provides compounds of Formula I as described herein. Compounds of Formula I have the following structure:

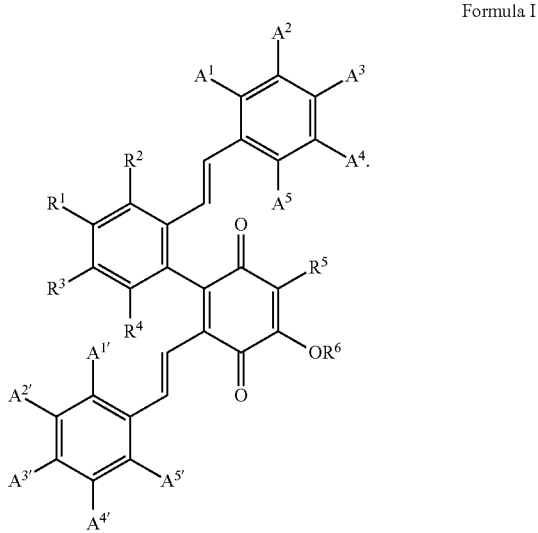

Formula I

In the compound of Formula I, at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein at each occurrence R is independently hydrogen, (C$_1$-C$_{100}$)hydrocarbyl, alkyl, acyl, cycloalkyl, aryl, aralkyl, heterocyclyl, heteroaryl, or heteroarylalkyl;

and at each occurrence $R^6$ is independently selected from hydrogen, CF$_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R. In some embodiments, R is (C$_1$-C$_{12}$) hydrocarbyl.

Compounds of Formula I, in some embodiments, have anti-bacterial and can kill pathogenic bacteria that cause deleterious infections and/or diseases in mammals, including Gram-positive bacteria. Surprisingly and unexpectedly, in some embodiments, bacteria do not develop resistance to the compounds of Formula I even after coming into contact with or becoming exposed to these compounds for 12 weeks or more.

In some embodiments, the compounds of Formula I can be used to treat or ameliorate psoriasis and/or atopic dermatitis in a subject. The treatment includes applying a compound of Formula I, and/or a composition containing a compound of Formula I, to an affected area of the skin of the subject. The composition can be a topical or transdermal composition.

BRIEF DESCRIPTION OF THE FIGURES

The drawings illustrate generally, by way of example, but not by way of limitation, various embodiments of the present invention.

FIG. 11A. TIC chromatogram of duotap-520 (5). FIG. 11B. TIC chromatogram of duotap-520 (5) incubated for overnight at 37° C. in buffer.

(FIG. 20B) Resistance mutations observed by whole genome sequencing for duotap-resistant MRSA. (FIG. 20C) Mutant allele frequencies of candidate resistance genes (quantified as the percent of total whole genome sequencing reads at each position) observed after culturing strains for 30, 60, and 90 days in duotap Given sequencing coverage. the limit of detection is 0.6%.

(FIG. 21B) Accumulation of the cell wall precursor UDP-MurNAc-pentapeptide in MRSA treated with duotap-520 compared to cells treated with DMSO. Vancomycin was used as a positive control. The UDP-MurNAc-pentapeptide was identified by mass spectrometry, with an $[M+H]^+$ of 1150.3590. Error bars represent the standard deviation of three biological replicates. (FIG. 21C) Supplementation of lipid II into growth medium can restore growth of MRSA exposed to duotap-520 (Compound 1) and vancomycin (known to bind lipid II) to antibiotic-free levels. Lipid II cannot rescue bacteria grown in the presence of ciprofloxacin (an inhibitor of DNA replication). Data from three biological replicates are shown. (FIG. 21D) Accumulation of lipid II in MRSA treated with duotap-520 compared to cells treated with DMSO. Vancomycin was used as a positive control. Lipid II was boiled to remove the lipid tail, and de-lipidated lipid II was quantified by mass spectrometry, with an $[M+H]^+$ of 1331.5362. Error bars represent the standard deviation of three biological replicates.

DETAILED DESCRIPTION OF THE INVENTION

Figure 1A:
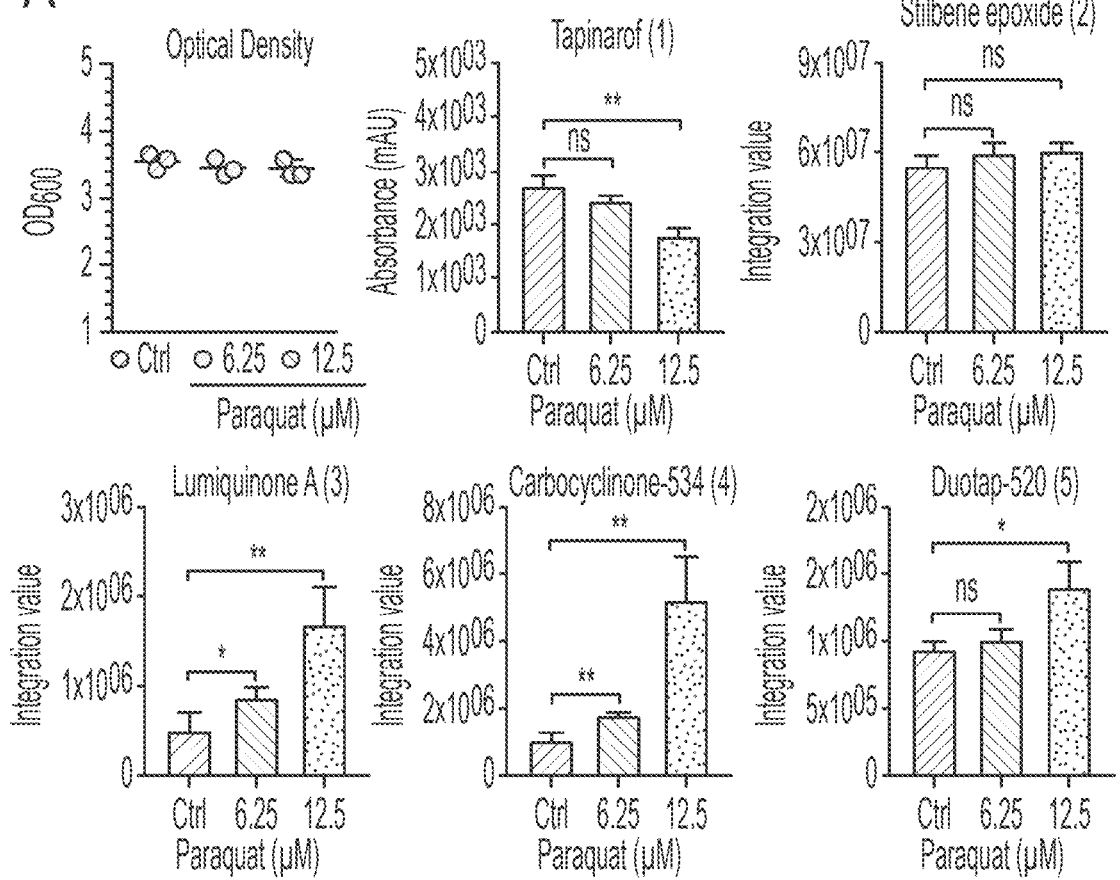
FIG. 1A shows the response of metabolites in *P. luminescens* to paraquat-induced redox stress. Optical densities of cell cultures were measured at 48 h after paraquat exposure compared to controls (Ctrl) lacking paraquat. They axis shows integration values of peaks extracted with corresponding positively charged m/z of 1-5. Data are mean±SEM for three biological replicates. *P<0.05; P<0.01; *P<0.001 by two-tailed student's t-test. ns indicates non-significant.

Described herein are tapinarof derivatives obtained by enzymatic action in *P. luminescens* and *P. asymbiotica*. These stilbene dimer derivatives have high potency against methicillin-resistant *Staphylococcus aureus* (MRSA) and vancomycin-resistant *Enterococcus faecalis* (VRE). Subsequent studies showed that MRSA failed to develop resistance even after prolonged exposure to these antibacterial agents.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Definitions

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The terms "epoxy-functional" or "epoxy-substituted" as used herein refers to a functional group in which an oxygen atom, the epoxy substituent, is directly attached to two adjacent carbon atoms of a carbon chain or ring system. Examples of epoxy-substituted functional groups include, but are not limited to, 2,3-epoxypropyl, 3,4-epoxybutyl, 4,5-epoxypelityl, 2,3-epoxypropoxy, epoxypropoxypropyl, 2-glycidoxyethyl, 3-glycidoxypropyl, 4-glycidoxybutyl, 2-(glycidoxycarbonyl)propyl, 3-(3,4-epoxycylohexyl)propyl, 2-(3,4-epoxycyclohexyl)ethyl, 2-(2,3-epoxycylopentyl)ethyl, 2+1-methyl-3,4-epoxycyclohexyl)propyl, 2-(3,4-epoxy-3-methylcylohexyl)-2-methylethyl, and 5,6-epoxyhexyl.

The term "monovalent" as used herein refers to a substituent connecting via a single bond to a substituted molecule. When a substituent is monovalent, such as, for example, F or Cl, it is bonded to the atom it is substituting by a single bond.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as ($C_a$-$C_b$)hydrocarbyl, wherein a and b are integers and mean having any of a to b number of carbon atoms. For example, ($C_1$-$C_4$)hydrocarbyl means the hydrocarbyl group can be methyl ($C_1$), ethyl ($C_2$), propyl ($C_3$), or butyl ($C_4$), and ($C_0$-$C_b$)hydrocarbyl means in certain embodiments there is no hydrocarbyl group.

The term "solvent" as used herein refers to a liquid that can dissolve a solid, liquid, or gas. Non-limiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "standard temperature and pressure" as used herein refers to 20° C. and 101 kPa.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system.

An appropriate therapeutic amount in any individual case may be determined by one of ordinary skill in the art using routine experimentation.

As used herein, the term "efficacy" refers to the maximal effect (Emax) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, P-hydroxybutyric, salicylic, galactaric and galacturonic acid.

Suitable pharmaceutically acceptable base addition salts of compounds of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein the term "minimum inhibitory concentration" (MIC) is the lowest concentration of a compound that prevents visible growth of a bacterium. The visible growth can be measured spectroscopically or through an optical microscope, for example.

Preparation of Compounds

Compounds of Formula I or compounds otherwise described herein can be prepared by the general schemes described herein, using the synthetic method known by those skilled in the art. The following examples illustrate non-limiting embodiments of the invention.

The compounds described herein can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}$H, $^{3}$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

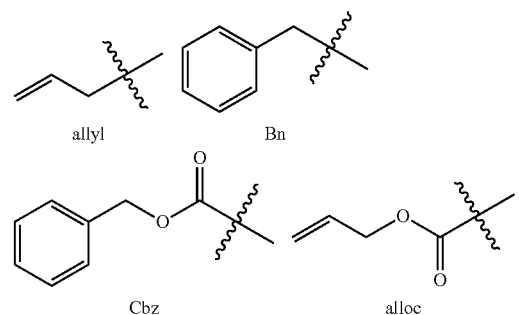

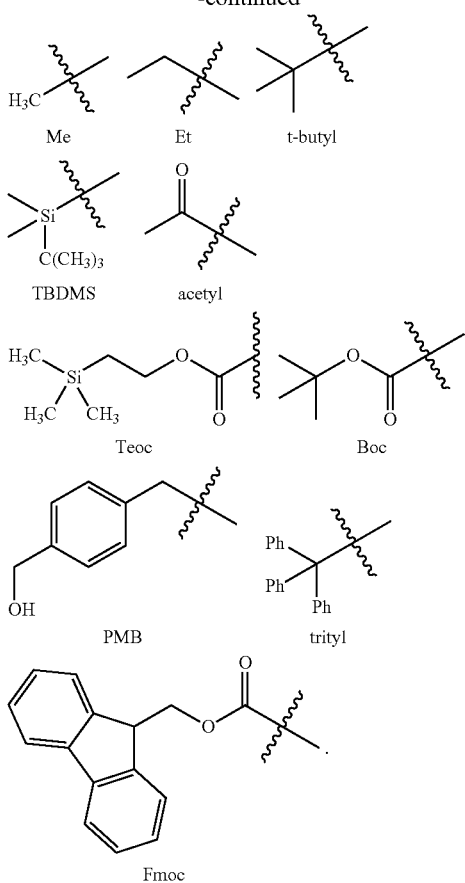

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Compositions

The invention includes a pharmaceutical composition comprising at least one compound of the invention and at least one pharmaceutically acceptable carrier. In certain embodiments, the composition is formulated for an administration route such as oral or parenteral, for example, transdermal, transmucosal (e.g., sublingual, lingual, (trans)buccal, (trans)urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intra-arterial, intravenous, intrabronchial, inhalation, and topical administration. In various embodiments, a pharmaceutical composition includes the compound of Formula I, or salts and solvates thereof, and at least one pharmaceutically acceptable excipient.

Administration/Dosage/Formulations

The regimen of administration may affect what constitutes an effective amount. The therapeutic formulations may be administered to the subject either prior to or after the onset of a disease or disorder contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated herein. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated herein in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated herein in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physician taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 350 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated herein in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or similar alcohol.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration. As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated herein in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

Anti-Bacterial Stilbene Derivatives

In various embodiments, the compounds of the invention are compounds of Formula I, or a salt, solvate, tautomer, enantiomer, or geometric isomer thereof:

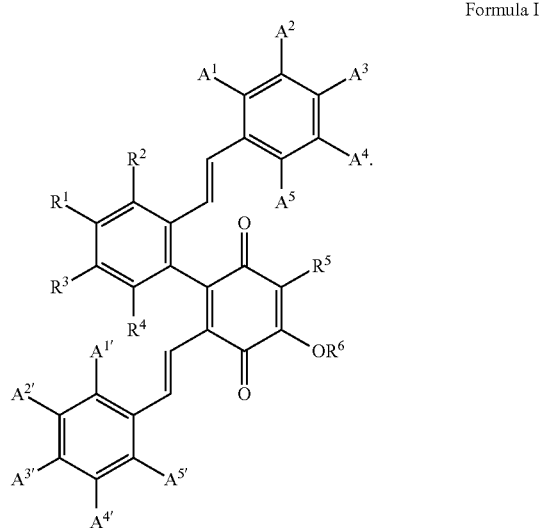

Formula I

In certain embodiments, in the compound of Formula I, at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R.

In certain embodiments, in the compound of Formula I, at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO$_2$, azido, CF$_3$, OCF$_3$, R, N(R)$_2$, SR, SOR, SO$_2$R, SO$_2$N(R)$_2$, SO$_3$R, C(O)R, C(O)C(O)R, C(O)CH$_2$C(O)R, C(O)OR, OC(O)R, C(O)N(R)$_2$, OC(O)N(R)$_2$, (CH$_2$)$_{0-2}$N(R)C(O)R, N(R)SO$_2$R, N(R)C(O)OR, N(R)C(O)R, N(R)C(O)N(R)$_2$, N(R)C(S)N(R)$_2$, N(OR)R, C(=NH)N(R)$_2$, C(O)N(OR)R, and C(=NOR)R.

In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$ and/or $A^{5'}$ is/are hydrogen. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are F. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are Cl. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are Br. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are I. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are OR. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are OC(O)N(R)$_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are CN. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are NO. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$ and/or $A^{5'}$ is/are NO$_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $ONO_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are azido. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $CF_3$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $OCF_3$. In certain embodiments, $R^1 R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are methylenedioxy. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are ethylenedioxy. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are SR. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are SOR. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $SO_2R$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $SO_2N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $SO_3R$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are C(O)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are C(O)C(O)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $C(O)CH_2C(O)R$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are C(S)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are C(O)OR. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are OC(O)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $C(O)N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $OC(O)N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $C(S)N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $(CH_2)_{0-2}N(R)C(O)R$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $(CH_2)_{0-2}N(R)N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are N(R)N(R)C(O)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are N(R)N(R)C(O)OR. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $N(R)N(R)CON(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $N(R)SO_2R$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $N(R)SO_2N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are N(R)C(O)OR. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are N(R)C(O)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are N(R)C(S)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $N(R)C(O)N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $N(R)C(S)N(R)_2$. In certain embodiments, R', R2, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are N(COR)COR. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are N(OR)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are $C(=NH)N(R)_2$. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are C(O)N(OR)R. In certain embodiments, $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and/or $A^{5'}$ is/are C(=NOR)R.

In certain embodiments, at each occurrence R is independently hydrogen, $(C_1-C_{100})$hydrocarbyl, alkyl, acyl, cycloalkyl, aryl, aralkyl, heterocyclyl, heteroaryl, or heteroarylalkyl.

In certain embodiments, R is hydrogen. In certain embodiments, R is hydrogen. In certain embodiments, R is $(C_1-C_{100})$hydrocarbyl. In certain embodiments, R is $(C_1-C_{12})$ hydrocarbyl. In certain embodiments, R is alkyl. In certain embodiments, R is acyl. In certain embodiments, R is cycloalkyl. In certain embodiments, R is aryl. In certain embodiments, R is aralkyl. In certain embodiments, R is heterocyclyl. In certain embodiments, R is heteroaryl. In certain embodiments, R is heteroarylalkyl.

In certain embodiments, each occurrence $R^6$ is independently selected from hydrogen, $CF_3$, R, methylenedioxy, ethylenedioxy, C(O)R, C(O)C(O)R, $C(O)CH_2C(O)R$, C(S)R, C(O)OR, OC(O)R, $C(O)N(R)_2$, $OC(O)N(R)_2$, $C(S)N(R)_2$, $(CH_2)_{1-2}N(R)C(O)R$, $(CH_2)_{1-2}N(R)N(R)_2$, $C(=NH)N(R)_2$, C(O)N(OR)R, and C(=NOR)R. In some embodiments, R is $(C_1-C_{12})$ hydrocarbyl.

In certain embodiments, $R^6$ is hydrogen. In certain embodiments, $R^6$ is $CF_3$. In certain embodiments, $R^6$ is R. In certain embodiments, $R^6$ is methylenedioxy. In certain embodiments, $R^6$ is ethylenedioxy. In certain embodiments, $R^6$ is C(O)R. In certain embodiments, $R^6$ is C(O)C(O)R. In certain embodiments, $R^6$ is $C(O)CH_2C(O)R$. In certain embodiments, $R^6$ is C(S)R. In certain embodiments, $R^6$ is C(O)OR. In certain embodiments, $R^6$ is OC(O)R. In certain embodiments, $R^6$ is $C(O)N(R)_2$. In certain embodiments, $R^6$ is $OC(O)N(R)_2$. In certain embodiments, $R^6$ is $C(S)N(R)_2$. In certain embodiments, $R^6$ is $(CH_2)_{1-2}N(R)C(O)R$. In certain embodiments, $R^6$ is $(CH_2)_{1-2}N(R)N(R)_2$. In certain embodiments, $R^6$ is $C(=NH)N(R)_2$. In certain embodiments, $R^6$ is C(O)N(OR)R. In certain embodiments, $R^6$ is C(=NOR)R.

In various embodiments, $A^1$ and $A^{1'}$ are the same. In various embodiments, $A^2$ and $A^{2'}$ are the same. In various embodiments, $A^3$ and $A^{3'}$ are the same. In various embodiments, $A^4$ and $A^{4'}$ are the same. In various embodiments, $A^5$ and $A^{5'}$ are the same. In various embodiments, $A^1$, $A^2$, $A^3$, $A^4$, and $A^5$ are all hydrogen. In various embodiments, $A^{1'}$, $A^{2'}$, $A^{3'}$, $A^{4'}$, and $A^{5'}$ are all hydrogen. In various embodiments, $R^3$ and $R^5$ are iso-propyl. In various embodiments, $R^1$ and $R^4$ are OH. In various embodiments, $R^3$ and $R^5$ are hydrogen. In various embodiments, $A^3$ and $A^{3'}$ are OH.

The compounds of the invention, in various embodiments, can be compounds of Formula II, or a salt, solvate, tautomer, enantiomer, or geometric isomer thereof:

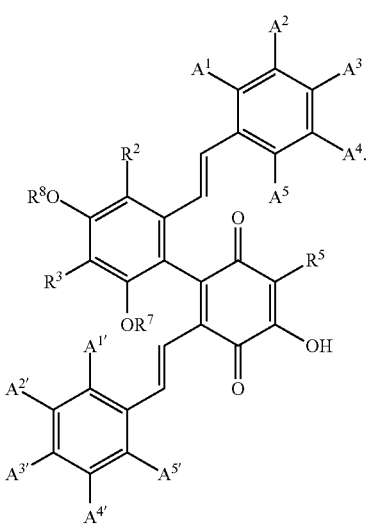

Formula II

In the compound of Formula II, at each occurrence $R^7$ and $R^8$ are independently selected from hydrogen, $CF_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R. In various embodiments, $R^7$ and $R^8$ are hydrogen.

In certain embodiments, $R^7$ is hydrogen. In certain embodiments, $R^7$ is $CF_3$. In certain embodiments, $R^7$ is R. In certain embodiments, $R^7$ is methylenedioxy. In certain embodiments, $R^7$ is ethylenedioxy. In certain embodiments, $R^7$ is C(O)R. In certain embodiments, $R^7$ is C(O)C(O)R. In certain embodiments, $R^7$ is C(O)CH$_2$C(O)R. In certain embodiments, $R^7$ is C(S)R. In certain embodiments, $R^7$ is C(O)OR. In certain embodiments, $R^7$ is OC(O)R. In certain embodiments, $R^7$ is C(O)N(R)$_2$. In certain embodiments, $R^7$ is OC(O)N(R)$_2$. In certain embodiments, $R^7$ is C(S)N(R)$_2$. In certain embodiments, $R^7$ is (CH$_2$)$_{1-2}$N(R)C(O)R. In certain embodiments, $R^7$ is (CH$_2$)$_{1-2}$N(R)N(R)$_2$. In certain embodiments, $R^7$ is C(=NH)N(R)$_2$. In certain embodiments, $R^7$ is C(O)N(OR)R. In certain embodiments, $R^7$ is C(=NOR)R. n certain embodiments, $R^8$ is hydrogen. In certain embodiments, $R^8$ is $CF_3$. In certain embodiments, $R^8$ is R. In certain embodiments, $R^8$ is methylenedioxy. In certain embodiments, $R^8$ is ethylenedioxy. In certain embodiments, $R^8$ is C(O)R. In certain embodiments, $R^8$ is C(O)C(O)R. In certain embodiments, $R^8$ is C(O)CH$_2$C(O)R. In certain embodiments, $R^8$ is C(S)R. In certain embodiments, $R^8$ is C(O)OR. In certain embodiments, $R^8$ is OC(O)R. In certain embodiments, $R^8$ is C(O)N(R)$_2$. In certain embodiments, $R^8$ is OC(O)N(R)$_2$. In certain embodiments, $R^8$ is C(S)N(R)$_2$. In certain embodiments, $R^8$ is (CH$_2$)$_{1-2}$N(R)C(O)R. In certain embodiments, $R^8$ is (CH$_2$)$_{1-2}$N(R)N(R)$_2$. In certain embodiments, $R^8$ is C(=NH)N(R)$_2$. In certain embodiments, $R^8$ is C(O)N(OR)R. In certain embodiments, $R^8$ is C(=NOR)R.

In various embodiments, $R^7$ and $R^8$ are hydrogen.

A compound of the invention can also be a compound of Formula III, or a salt, solvate, tautomer, enantiomer, or geometric isomer thereof:

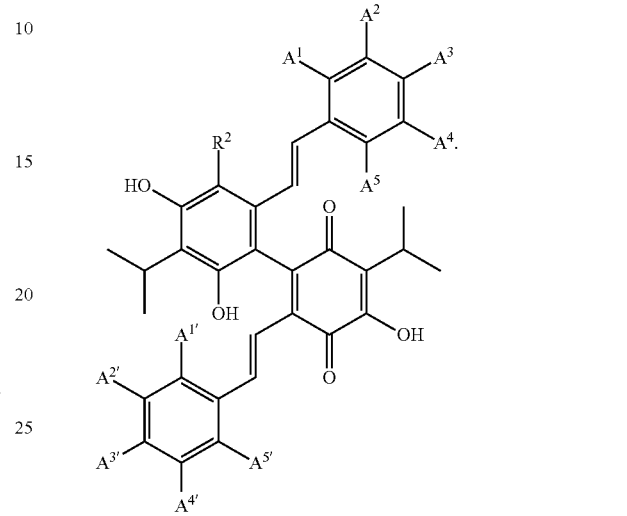

Formula III

In various embodiments, in the compound of Formula III, at least one of $A^1$, $A^2$, $A^3$, $A^4$, $A^5$, $A^{1'}$, $A^{2'}$, $A^{3'}$, $A^{4'}$, and $A^{5'}$ is not hydrogen. In various embodiments, $A^1$ is not hydrogen. In various embodiments, $A^2$ is not hydrogen. In various embodiments, $A^3$ is not hydrogen. In various embodiments, $A^4$ is not hydrogen. In various embodiments, $A^5$ is not hydrogen. In various embodiments, $A^{1'}$ is not hydrogen. In various embodiments, $A^{2'}$ is not hydrogen. In various embodiments, $A^{3'}$ is not hydrogen. In various embodiments, $A^{4'}$ is not hydrogen. In various embodiments, $A^{5'}$ is not hydrogen.

In various embodiments, the compound is selected from the group consisting of

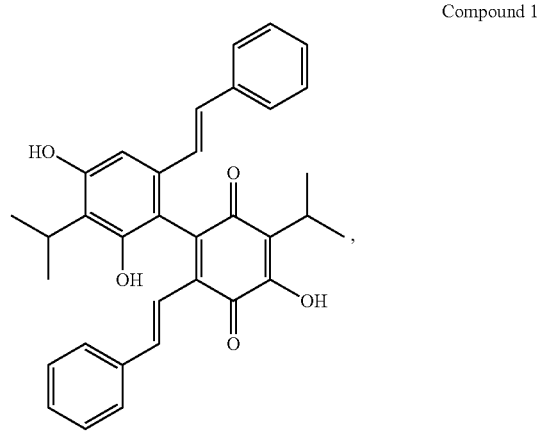

Compound 1

Compound 2

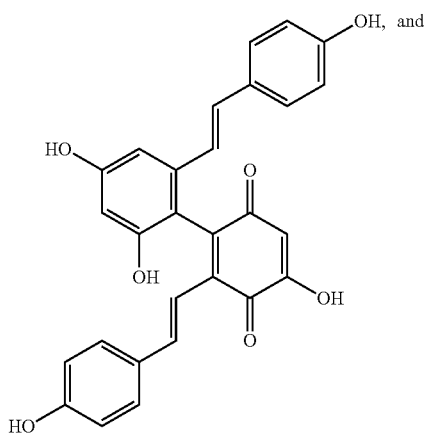

Compound 3

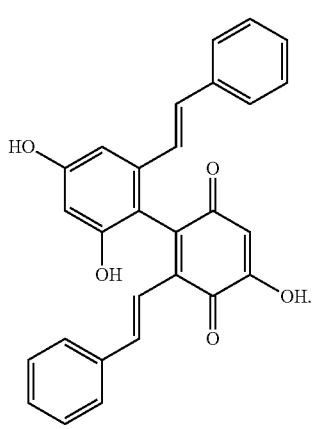

Scheme 1

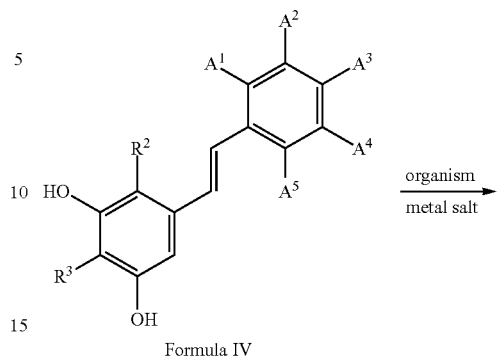

Formula IV

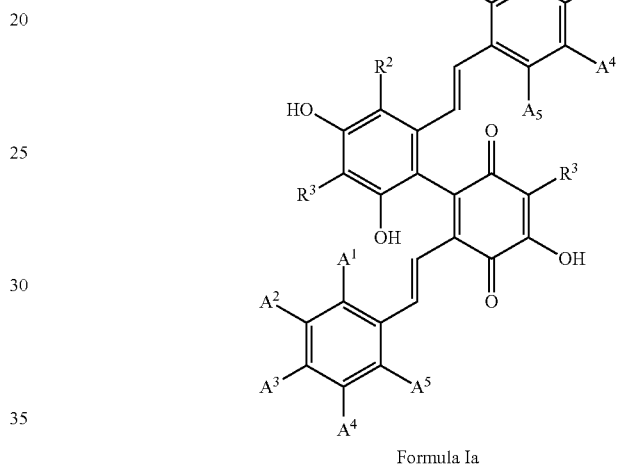

Formula Ia

In various embodiments, one or more hydroxyl or amine groups, when present in the compound of Formula I, can be substituted with a metabolizable group that is removed by metabolic processes in the subject (e.g., a prodrug). For example, if the compound of Formula I is dosed non-topically, these groups can be removed by enzymes in the mouth, stomach, small intestine, large intestine, other portions of the gastrointestinal tract, or the liver. Non-limiting examples of suitable metabolizable groups include esters, sulfonamides, carboxamides, carbamates, phosphate esters, and the like.

Methods of Synthesizing Anti-bacterial Stilbene Derivatives

The compounds of Formula I form when stilbene derivatives oxidatively dimerize. For example, a compound of Formula IV can undergo oxidative dimerization in the presence of certain organisms to produce a compound of Formula Ia. Suitable organisms include bacteria, such as E. coli, that have been transformed with a gene capable of effecting the reaction in Scheme 1.

In various embodiments, a method of making a compound of Formula Ia includes contacting a compound of Formula IV with a medium including an organism and at least one metal salt, to produce a compound of Formula Ia. In various embodiments, the compound of Formula Ia can be produced in a suitable medium capable of sustaining the organism and one or more metal salts. In various embodiments, the organism includes a transformed organism containing a Plu1886 gene. In various embodiments, the organism is a transformed bacterial strain that, when it incorporates a gene, is capable of effecting the transformation in Scheme 1. In various embodiments, the organism is a transformed E. coli BL21 (DE3) containing the Plu1886 gene from P. luminescens, or a gene that has at least about, greater than, or less than 80%, 85%, 90%, 92%, 94%, 96%, 98%, or 99% homology with the Plu1886 gene from P. luminescens. The medium capable of sustaining the organism can be any art-recognized medium that is capable of maintaining the viability and functioning of the organism until the reaction in Scheme 1 is complete or a sufficient amount of the compound of Formula I has formed. In various embodiments, the medium comprises a pH buffered medium that buffers at a pH of about 6.5 to about 8.5. In various embodiments, the medium comprises sodium phosphate buffer at a pH of 7.4.

In various embodiments, a Plu1886 gene from P. luminescens has the sequence of SEQ ID NO. 1.

SEQ ID NO. 1:
ATGGAATTTATTAAAAATAGATTTTGTCACTGGAA

CGGTGAACACCTTGTTGTCGATACAATGGCCAGAA

ATCATAAAATGGTTAACAGTATGGGAACGGGCGAG

GGATTAGTTTCGTTTGATGGCTTTGGTGCTGATCT

AATTCGTTTCAGCAAAGATGAGGGGATGCAGAATC

ATACTCACTTAGGGCATCATATCTTATTTGTCCTC

GCAGGAACGGGTTATGTTATTTATGCGGGTGAAAA

GCATAAAATAGAGCCTGGAGTTTGTTATTTTGTGA

ATGGAGAAATAGATCACGCGATTAAAGCAACCAGC

GATTTGGTTATGCTTGTTGTCGGTAATAATCATTG

TGCGGTTGATGCGCAAGATAGGACGACGCTGGTGC

CATATAGAGAGGGAACGCCAGAGGAATTAAAGGTT

TAA.

The compound of Formula I (starting material) can be present in the medium at a concentration of about 0.01 µM to about 50 µM, 0.05 mM to about 10 mM, about 0.1 mM to about 5 mM, or about 0.5 mM to about 3 mM. The compound of Formula I can be present in the medium at a concentration of at least, greater than, or less than about 0.01 µM, 0.05 µM, 0.1 µM, 0.2 µM, 0.4 µM, 0.6 µM, 0.8 µM, 1 µM, 1.5 µM, 2 µM, 2.5 µM, 3 µM, 3.5 µM, 4 µM, 4.5 µM, 5 µM, 5.5 µM, 6 µM, 6.5 µM, 7 µM, 7.5 µM, 8 µM, 8.5 µM, 9 µM, 9.5 µM, 10 µM, 12 µM, 14 µM, 16 µM, 18 µM, 20 µM, 22 µM, 24 µM, 26 µM, 28 µM, 30 µM, 35 µM, 40 µM, 45 µM, 0.05 mM, 0.15 mM, 0.25 mM, 0.35 mM, 0.45 mM, 0.55 mM, 0.65 mM, 0.75 mM, 0.85 mM, 0.95 mM, 1 mM, 1.2 mM, 1.4 mM, 1.6 mM, 1.8 mM, 2 mM, 2.2 mM, 2.4 mM, 2.6 mM, 2.8 mM, 3 mM, 3.2 mM, 3.4 mM, 3.6 mM, 3.8 mM, 4 mM, 4.2 mM, 4.4 mM, 4.6 mM, 4.8 mM, 5 mM, 5.2 mM, 5.4 mM, 5.6 mM, 5.8 mM, 6 mM, 6.2 mM, 6.4 mM, 6.6 mM, 6.8 mM, 7 mM, 7.2 mM, 7.4 mM, 7.6 mM, 7.8 mM, 8 mM, 8.2 mM, 8.4 mM, 8.6 mM, 8.8 mM, 9 mM, 9.2 mM, 9.4 mM, 9.6 mM, 9.8 mM, or 10 mM.

The metal salt can be an organic or inorganic salt of at least one metal from Group I through Group XII in the periodic table. Suitable organic salts include metal salts of any of the organic acids described herein. Suitable inorganic salts include chloride, bromide, iodide, fluoride, sulfate ($SO_4^{2-}$), phosphate ($PO_4^{2-}$), nitrate, carbonate, and the like. In various embodiments, the metal salt is a salt of Li, Na, K, Cs, Mg, Ca, Sr, Ba, Sc, Ti, V, Cr, Mn, Fe, Co, Ni, Cu, Zn, Zr, Ru, Rh, Pd, Ag, W, Re, Os, Ir, Pt, or Au. When a metal can have more than one oxidation state, such as Mn, salts of any of the oxidation states can be used provided they are capable of carrying out the transformation depicted in Scheme 1. In various embodiments, the metal salt is a salt of Ni, Ca, Fe, Cu, Zn, Co, Mg, or Mn. In various embodiments, the metal salt is a chloride or a sulfate. In various embodiments, the metal salt is at least one salt selected from $NiCl_2$, $CaCl_2$, $FeSO_4$, $CuSO_4$, $ZnSO_4$, $CoCl_2$, $MgSO_4$, or $MnCl_2$.

The metal salt can be present in the medium at a concentration of about 0.05 mM to about 5 mM, or about 0.1 mM to about 4 mM, or about 0.2 mM to about 3 mM, or about 0.3 mM to about 2 mM. The metal salt can be present in the medium at a concentration of at least, greater than, or less than about 0.05 mM, 0.15 mM, 0.25 mM, 0.35 mM, 0.45 mM, 0.55 mM, 0.65 mM, 0.75 mM, 0.85 mM, 0.95 mM, 1 mM, 1.2 mM, 1.4 mM, 1.6 mM, 1.8 mM, 2 mM, 2.2 mM, 2.4 mM, 2.6 mM, 2.8 mM, 3 mM, 3.2 mM, 3.4 mM, 3.6 mM, 3.8 mM, 4 mM, 4.2 mM, 4.4 mM, 4.6 mM, 4.8 mM, or 5 mM.

In various embodiments, the Plu1886 gene from *P. luminescens* encodes an enzyme capable carrying out the transformation in Scheme 1. In various embodiments, the enzyme is present in the medium at a concentration of about 0.01 µM to about 100 µM. The enzyme can be present in the medium at a concentration of at least, greater than, or less than about 0.01 µM, 0.05 µM, 0.1 µM, 0.2 µM, 0.4 µM, 0.6 µM, 0.8 µM, 1 µM, 1.5 µM, 2 µM, 2.5 µM, 3 µM, 3.5 µM, 4 µM, 4.5 µM, 5 µM, 5.5 µM, 6 µM, 6.5 µM, 7 µM, 7.5 µM, 8 µM, 8.5 µM, 9 µM, 9.5 µM, 10 µM, 12 µM, 14 µM, 16 µM, 18 µM, 20 µM, 22 µM, 24 µM, 26 µM, 28 µM, 30 µM, 35 µM, 40 µM, 45 µM, 55 µM, 60 µM, 65 µM, 70 µM, 75 µM, 80 µM, 85 µM, 90 µM, 95 µM, or 100 µM. The enzyme encoded by the Plu1886 gene from *P. luminescens* is, in various embodiments, isolated from the transformed *E. coli* (or other suitable organism) prior to reacting with compounds of Formula I. Isolation of the enzyme can be accomplished by techniques known in the art. In various embodiments, compounds of Formula I can react with the metal salt(s) described herein in the absence of any organism or enzyme to form compounds of Formula Ia.

Compounds of Formula Ia can also be produced in situ in a subject by exposing a compound of Formula IV to gut microorganisms (microbiome) that are capable of effecting the transformation in Scheme 1, with or without the presence of a metal salt, or the addition of a metal salt. For example, the in situ site can be any portion of the gastrointestinal tract of a subject, including the esophagus, stomach, small intestine, and/or large intestine. The microorganisms can be existing populations found in the digestive tract of a subject, or the microorganisms can be provided to the subject. In various embodiments, the medium includes a gastrointestinal tract of a subject, the organism includes a bacterial population (microbiome) in the subject, and the metal salt comprises a metal salt in the gastrointestinal tract of the subject. The metal salt in the gastrointestinal tract of the subject can be a naturally occurring metal salt or a metal salt that was given to (e.g., ingested) the subject. In various embodiments, a microorganism capable of transforming a compound of Formula IV to a compound of Formula Ia can be administered to a subject together with a compound of Formula IV. For example, a composition that contains a compound of Formula IV and at least one microorganism capable of transforming a compound of Formula IV to a compound of Formula Ia can be administered, either separately, concomitantly, or in a co-formulated manner.

Methods of Treatment and Use

A method of killing or disinfecting bacteria includes, in various embodiments, contacting a bacterial population with a compound of Formula I, wherein the bacterial population is killed or disinfected after coming into contact with the compound of Formula I.

The compounds of Formula I have anti-bacterial properties, and are able to kill at least, or greater than about 95%, 98%, 99%, 99.1%, 99.2%, 99.3%, 99.4%, 99.5%, 99.6%, 99.7%, 99.8%, 99.9%, 99.99%, 99.999%, or 99.9999% of bacteria that come in contact with or are exposed to the compounds of Formula I. In various embodiments, the bacteria that are killed are pathogenic bacteria that cause deleterious infections and/or diseases in mammals. In various embodiments, the bacteria are Gram-positive. In various embodiments, the mammal is a cat, dog, human, sheep, horse, mouse, rabbit, rat, cow, goat, pig, and the like. The term "kill" as used herein means that the bacteria are no longer able to exhibit or produce any harmful effect to or in a living organism, and/or that the bacteria are unable to cause further infection, and/or the bacteria cease to live.

The types of bacteria that can be killed by the compounds of the invention is not particularly limited. Non-limiting examples of bacteria genera that are killed when exposed to compounds of Formula I include *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia*. Additionally, the compounds of Formula I can kill any species of bacteria in the aforementioned genera that are known to infect humans or other mammals. In various embodiments, the compounds of Formula I kill VRE and/or MRSA. In various embodiments, the bacterial population includes methicillin-resistant *Staphylococcus aureus* (MRSA), vancomycin-resistant *Enterococcus faecalis* (VRE), and/or a combination thereof.

In various embodiments, the compounds of Formula I have a minimum inhibitory concentration (MIC) with respect to any of the bacteria described herein of about 0.01 µM to about 100 µM, about 0.5 µM to about 50 µM, about 1 µM to about 40 µM, about 2 µM to about 30 µM, about 3 µM to about 20 µM, or about 1 µM to about 10 µM. In various embodiments, the compounds of Formula I have a MIC with respect to any of the bacteria described herein of at least, greater than, or less than about 0.05 µM, 0.15 µM, 0.25 µM, 0.35 µM, 0.45 µM, 0.55 µM, 0.65 µM, 0.75 µM, 0.85 µM, 0.95 µM, 1 µM, 1.2 µM, 1.4 µM, 1.6 µM, 1.8 µM, 2 µM, 2.2 µM, 2.4 µM, 2.6 µM, 2.8 µM, 3 µM, 3.2 µM, 3.4 µM, 3.6 µM, 3.8 µM, 4 µM, 4.2 µM, 4.4 µM, 4.6 µM, 4.8 µM, 5 µM, 5.2 µM, 5.4 µM, 5.6 µM, 5.8 µM, 6 µM, 6.2 µM, 6.4 µM, 6.6 µM, 6.8 µM, 7 µM, 7.2 µM, 7.4 µM, 7.6 µM, 7.8 µM, 8 µM, 8.2 µM, 8.4 µM, 8.6 µM, 8.8 µM, 9 µM, 9.2 µM, 9.4 µM, 9.6 µM, 9.8 µM, or 10 µM. In various embodiments, the compounds of Formula I have a higher MIC against VRE than against MRSA.

Surprisingly and unexpectedly it was discovered that, in various embodiments, bacteria do not develop resistance to the compounds of Formula I after coming into contact with or becoming exposed to these compounds. The phrase "do not develop resistance" means that the killing ability of the compounds described herein does not substantially diminish over time. Bacterial resistance typically occurs after bacteria have been exposed to an antibiotic for a period of time. Certain small sub-populations of bacteria are not affected or as affected by an antibiotic, or develop mutations that make the bacteria resistant to the antibiotic. These sub-populations can grow and multiply so that eventually a particular bacterial population is no longer affected by a particular antibiotic. In these cases, different classes of antibiotics need to be used, but bacterial populations can change such that eventually they become resistant to all types of commonly used antibiotics.

However, it was unexpectedly discovered that the compounds of Formula I do not produce antibiotic resistance in bacteria. Bacteria treated with the compounds described herein for a prolonged period continue to be killed to substantially the same extent as when the bacteria was first exposed to the compounds of Formula I. In various embodiments, bacteria do not develop resistance after at least, less than, or greater than about 1 week, 2 weeks, 3 weeks, 4 weeks, 5 weeks, 6 weeks, 7 weeks, 8 weeks, 9 weeks, 10 weeks, 11 weeks, or 12 weeks of exposure to the compounds of Formula I. In various embodiments, bacteria do not develop resistance after at least, less than, or greater than about 6 weeks. The exposure can include any of the dosing regimens described herein. In various embodiments, bacteria are killed at least or greater than about 100%, 99.99%, 99.9%, 99.5%, 99%, 98%, 97%, 96%, or 95% as effectively by the compounds of Formula I after exposure for any of the periods described herein as compared to the first exposure of the bacteria to the compounds of Formula I. In various embodiments, the bacterial population is killed at least about 95%, 96%, 97%, 98%, 99%, 99.5%, 99.9%, 99.99%, or 100% as effectively after coming into contact with the compound for the prolonged period as compared to the percentage of a similar bacterial population killed after first coming into contact with the compound. A "similar bacterial population" is a population that contains at least, greater than, or less than about 10%, 20%, 30%, 40%, 50%, 60%, 70%, 80%, 90%, 95%, or 100% of the same bacterial genus, or the same bacterial species, as another comparative bacterial population.

In various embodiments, the compounds of Formula I can be used to treat bacterial infections present in the body or on the skin of a mammal. Non-limiting examples of bacterial infections include bacterial vaginosis, bacterial meningitis I, bacterial pneumonia, bacterial upper respiratory infections, ear infections, eye infections, skin infections, thrush, urinary tract infection, bacterial gastroenteritis, impetigo, erysipelas, and cellulitis. A method of treating a bacterial infection in a subject includes administering to the subject a therapeutically effective amount of a composition comprising at least one pharmaceutically acceptable excipient and a compound of Formula I. The subject is, in various embodiments, a human.

In various embodiments, the compounds of Formula I can be used to disinfect non-living objects, including non-living objects or surfaces made from metals, ceramics, glass, wood, fabrics, rubber, plastic, polymers, and composite materials made from any combination of the foregoing, and combinations thereof. In various embodiments, the bacterial population is present on or in a non-living object. As used herein, the term "disinfect" means at least about 95%, 98%, 99%, 99.1%, 99.2%, 99.3%, 99.4%, 99.5%, 99.6%, 99.7%, 99.8%, 99.9%, 99.99%, 99.999%, or 99.9999% of bacteria on or in a non-living object that come into contact with or are exposed to the compounds of Formula I are no longer able to exhibit or produce any harmful effect to or in a living organism, and/or that the bacteria are unable to cause further infection, and/or the bacteria cease to live. In various embodiments, the bacteria disinfected on or from a non-living surface are pathogenic bacteria that can cause deleterious infections and/or diseases in mammals.

The compound of Formula I can also be formulated in a non-pharmaceutical composition that is intended for use on non-living objects or is used on living objects. Suitable non-pharmaceutical compositions can be in the form of sprays, gels, slow-dissolving tablets (e.g. for a toilet water reservoir), porous materials that incorporate the compounds of Formula I, and the like. The non-pharmaceutical compositions can include one or more excipients such as surfactants (cationic, anionic, neutral), emulsifiers, fragrances, thickening agents, artificial colors or dyes, detergents, water, salts, buffers, and the like.

Methods of Treating Psoriasis or Atopic Dermatitis

In some embodiments, the compounds of Formula I can be used to treat or ameliorate psoriasis and/or atopic dermatitis in a subject. In other embodiments, the method comprises applying a compound of Formula I, and/or a composition containing a compound of Formula I, to an affected area of the skin of the subject. The composition can be a topical or transdermal composition. Suitable topical compositions or transdermal compositions include, but are not limited to, creams, lotions, gels, or patches. The amount of a compound of Formula I used in a topical composition can range from about 0.0001 to about 10% (w/w) relative to the amount of topical composition applied to a subject's skin. In various embodiments, the amount of compound of Formula I used in a topical composition can range from about 0.0001 to about 5% (w/w), about 0.0001 to about 1% (w/w), about 0.001 to about 1% (w/w), or about 0.01 to about 1% (w/w) relative to the amount of topical composition applied to a subject's skin.

In various embodiments, the amount of compound of Formula I used in a topical composition can be about 0.0001, 0.001, 0.01, 0.05, 0.1, 0.2, 0.4, 0.6, 0.8, 1, 1.2, 1.4, 1.6, 1.8, 2, 3, 4, 5, 6, 7, 8, 9, or about 10% (w/w) relative to the amount of topical composition applied to a subject's skin. In some embodiments, the compound of Formula I is the only active agent in the topical composition. In other embodiments, the topical composition includes at least one other active agent that treats or ameliorates psoriasis and/or atopic dermatitis, or at least one active agent that provides another therapeutic effect aside from treating or ameliorating psoriasis and/or atopic dermatitis, such as an anti-inflammatory agent, an analgesic agent, an anti-microbial agents, and the like. These additional agents can be present in the amounts described herein for the compound of Formula I. The topical formulation can include additional excipients conventionally used in pharmaceutical or cosmetic compositions, such as perfumes, colorants, emulsifying agents, thickening agents, skin penetration enhancers, agents that increases the viscosity of the topical composition, agents that decreases the viscosity of the topical composition, gel-forming agents, hydrogel-forming agents, and the like. With respect to methods of treating or ameliorating psoriasis and/or atopic dermatitis in a subject, statements regarding topical compositions apply equally to transdermal compositions.

Suitable steroidal anti-inflammatory agents include, but are not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Suitable non-steroidal anti-inflammatory agents, include, but are not limited to, piroxicam, isoxicam, tenoxicam, sudoxicam, aspirin, disalcid, benorylate, trilisate, safapryn, solprin, diflunisal, fendosal, diclofenac, fenclofenac, indomethacin, sulindac, tolmetin, isoxepac, furofenac, tiopinac, zidometacin, acematacin, fentiazac, zomepiract, clidanac, oxepinac, felbinac, mefenamic, meclofenamic, flufenamic, niflumic, tolfenamic, ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, tiaprofenic, phenylbutazone, oxyphenbutazone, feprazone, azapropazone, trimethazone, and mixtures thereof.

Suitable analgesic agents include, but are not limited acetaminophen, aspirin, diflunisal, ibuprofen, Motrin, Naprosyn, Nalfon, and Trilisate, indomethacin, glucametacine, acematacin, sulindac, naproxen, piroxicam, diclofenac, benoxaprofen, ketoprofen, oxaprozin, etodolac, ketorolac tromethamine, ketorolac, nabumetone, fentanyl, buprenorphine, codeine sulfate, morphine hydrochloride, codeine, hydromorphone (DILAUDID®), levorphanol (LEVO-DROMORAN®), methadone (DOLOPHINE®), morphine, oxycodone (in PERCODAN®), and oxymorphone (NU-MORPHAN®), and the like.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Experimental Methods

General Experimental Procedures. Optical rotation was obtained from a Rudolph Autopol VI (Hackettstown, NJ, USA) polarimeter with a path length of 10 mm. Electronic circular dichroism (ECD) was measured on a Chirascan (Applied Photophysics, Surrey, UK) spectrophotometer. Nuclear magnetic resonance (NMR) spectra were recorded on an Agilent 600 MHz NMR (Agilent, Santa Clara, CA, USA) spectrometer with a cold probe. Vacuum liquid chromatography (VLC) was performed using either LICHROPREP® RP-18 (40-63 µm) (Merck Millipore, Billerica, MA, USA) or SEP-PAK® Vac 35 cc (10 g) C18 cartridge (Waters, Milford, MA, USA). High performance liquid chromatography (HPLC) purification was accomplished on an Agilent Prepstar HPLC system, when needed, with an Agilent Polaris C18-A 5 µm (21.2×250 mm), Phenomenex Luna C18(2) or C8(2) (100 Å) 10 µm (10.0×250 mm) (Phenomenex, Torrance, CA, USA), and an Agilent Phenyl-Hexyl 5 µm (9.4×250 mm) columns. Analytical HPLC-mass (MS) was acquired by using an Agilent 1260 Infinity Quaternary LC system consisting of an autosampler, a quaternary solvent delivery system, thermostatted column compartment, and a photo diode array (PDA) detector coupled to an Agilent 6120 Quadrupole low-resolution (LR) electrospray ionization (ESI) mass spectrometer. High-resolution mass spectra (HRMS) were obtained from an Agilent iFunnel 6550 QTOF (quadrupole time of flight) MS instrument fitted with an ESI source coupled to an Agilent 1290 Infinity HPLC system. Agilent Software packages, including OpenLAB CDS ChemStation (Version C.01.04), MassHunter Workstation Data Acquisition (Version B.05.01), and MassHunter Qualitative Analysis (Version B.05.00), were used for the analyses of UV-HPLC-MS spectra.

LC-HRMS Metabolite Profiles from *P. luminescens* in Response to Redox Stress. A frozen stock of *Photorhabdus luminescens* TT01 was thawed, streaked, grown, and when needed, the strain was cultivated on lysogeny broth (LB) agar plates in a 30° C. stationary incubator. In the biological triplicate experiments, three single colonies were inoculated into 5 mL LB liquid medium in 3×14 mL polypropylene round-bottom culture tubes and incubated with 250 rpm at 30° C. for 18 h. Methyl viologen dichloride hydrate (MilliporeSigma, Burlington, MA, USA) was prepared and supplemented to fresh LB medium in two sublethal concentrations of 12.5 and 6.25 µM, which was followed by sterile filtration through 0.2 µm diameter filters. 2 µL overnight *P. luminescens* cultures were then dispensed into the paraquat-conditioned LB medium in the three biological replicates. *P. luminescens* under the sublethal paraquat-induced redox stress was incubated in a shaker with 250 rpm at 30° C., and the $OD_{600}$ was measured at the 48 h post-stressed condition. The cultures (5 mL) were centrifuged at 2,000×g for 20 min at 4° C. and the supernatants were extracted with ethyl acetate (6 mL). The ethyl acetate-soluble layers were dried under reduced pressure on a HT-4× evaporation system (Genevac Inc., Gardiner, NY). Dried crude materials were redissolved in 100 µL methanol, and 2 µL was injected for the high-resolution ESI-QTOF-MS analysis [column; Phenomenex Kinetex $C_{18}$ (100 Å) 5 µm (4.6×250 mm), flow rate; 0.7 mL min$^{-1}$, mobile phase; a H$_2$O/ACN gradient containing 0.1% formic acid (v/v): 0-30 min, 10-100% ACN; hold for 5 min, 100% ACN; 2 min, 100-10% ACN; 5 min post-time, 10% ACN]. Metabolic profiles were achieved by the comparison of UV and LC-FIRMS traces of the non-stressed group versus the stressed group, which was followed by extracted ion counts (EIC) corresponding to the observed m/z of the compounds of interest. Cultivation, Extraction, and Isolation. 5 mL *P. luminescens* culture was prepared, and 5 µl of overnight culture was dispensed into 12×5 mL fresh LB medium and further incubated in 250 rpm at 30° C. 12×4 L Erlenmeyer flasks each containing 1 L LB medium were prepared for the larger-scale cultivation. Each 5 mL culture was transferred into the corresponding 1 L LB medium and grown for 4 days. Dark brownish *P. luminescens* culture broth was centrifuged with 14,000×g for 30 min and the supernatant was subsequently extracted by ethyl acetate (2×121), and evaporated in vacuo. A sticky crude extract (approx. 800 mg from 12 L culture broth) was powdered with adsorbent SiO$_2$ (CELITE® 110, Millipore Sigma, St. Louis, MO, USA), and the sample was loaded and fractionated by solid phase extraction (SPE) on a vacuum manifold equipped with SEP-PAK® Vac 35 cc (10 g) C18 cartridge with a step gradient elution (40%, 60%, 80% and 100% aqueous MeOH). The desired 80% MeOH fraction was separated by a reversed-phase Agilent HPLC system with an Agilent Polaris C18 column (20×250 mm, 8 mL min$^{-1}$, 50-100% aqueous ACN in 0.01% TFA for 60 min, 1 min fraction). Compounds 4 and 5 were collected in fractions 36 and 38, and further isolated by Phenomenex C18 column (10×250 mm, 4 mL min$^{-1}$, 50-100% aqueous ACN in 0.01% TFA for 30 min), eluting the impure 4 and 5 at $t_R$=16.3 and 17.4 min, respectively. Compounds 4 (0.2 mg) and 5 (0.1 mg) were purified by Phenyl-Hexyl column (10×250 mm, 4 mL min$^{-1}$, 60-100% aqueous ACN in 0.01% TFA for 30 min) at $t_R$=11.2 and 13.6 min. Of note, this entire process was repeated 10 times, resulting in a yield of ~1 mg of natural 4 and 5 from a total of ~100 L *P. luminescens* cultivation.

NMR Studies. $^1$H and $^{13}$C chemical shifts given in ppm (δ) and coupling constants (J) in Hz were referenced to the residual peaks of MeOH-d$_4$ ($\delta_H$ 3.29 and $\delta_C$ 47.6). NMR spectra were analyzed using MestReNova software (Version 10.0.1). LR-HSQMBC was performed utilizing the t1 increments (indirect dimension) of 640, to evolve long-range heteronuclear correlations with the $^nJ_{CH}$ value being optimized to 2 Hz (transfer delay of 250 ms). The 1,1-ADEQUATE was initially implemented with 2 s relaxation time, 128 t1 increments, 160 scans, and $^1J_{CC}$ 50 Hz. The homonuclear coupling constant ($^1J_{CC}$) was adjusted to 10 Hz to specifically develop two-bond correlations for the detection of the core cyclopropyl motif comprising carbocyclinone-534 (4). The practical amount required for this experiment was ~7 mg in the laboratory setting. The 1D NOESY for PANIC analysis was conducted using the double-pulse field gradient spin-echo NOE (DPFGSENOE) excitation sculpted selective sequence incorporated with a zero-quantum filter component (500 ms mixing time, 2 s relaxation time, 64 scans). The resonance for proton at 6.8 ppm was selectively irradiated using 1D NOESY pulse and the corresponding integration was normalized into −1000 as an arbitrary number. The generated NOE intensity for proton at 7.0 ppm was then integrated with reference to −1000. The normalized integration value (NOE$_{reference}$) and the interproton distance of proton at 6.8 ppm with proton 7.0 ppm being 2.5 Å (r$_{reference}$), were used to solve an equation below to calibrate an interproton distance between protons at 3.9 and 4.4 ppm (r$_{unknown}$). The NOE$_{unknown}$ value was acquired by NOE-integration of proton at 3.9 ppm upon selective irradiation of proton at 4.4 ppm and normalization of the NOE integration value (−1000)$^2$.

$$NOE_{unknown}/NOE_{reference} = (r_{reference})^6/(r_{unknown})^6 \quad \text{Equation:}$$

X-ray Crystal Structure Analysis. Low-temperature diffraction data (ω-scans) were collected on a Rigaku MicroMax-007HF diffractometer coupled to a Saturn994+ CCD detector with Cu Kα (λ=1.54178 Ø) for the structure of carbocyclinone-534 (4). The diffraction images were processed and scaled using Rigaku Oxford Diffraction software. The structure was solved with SHELXT and was refined against F2 on all data by full-matrix least squares with SHELXL[3]. All non-hydrogen atoms were refined anisotropically. Hydrogen atoms were included in the model at geometrically calculated positions and refined using a riding model. The isotropic displacement parameters of all hydrogen atoms were fixed to 1.2 times the U value of the atoms to which they are linked (1.5 times for methyl groups). A summary of the general crystallographic information is reported in Table 1. The hydrogen positions associated with oxygen atoms O1, O4, O7, and O10 were found in the difference map and freely refined (see Table 2). One isopropyl group with atoms (C66, C67, C68) showed signs of a positional disorder. The second position was identified with atoms of the same number with the addition of a "B" suffix. When the occupancies of these "B" atoms were freely refined, the site occupancy split between the major and minor components converged to values of 0.839(4)/0.161(4) respectively. The chemically identical C—C bond distances were restrained to be similar. Two of the four acetonitriles were disordered over two positions. In a similar fashion to the isopropyl, the chemically identical C—C and C—N bond distances were restrained to be similar. The site occupancies were freely refined to values of 0.862(3)/0.138(3), with the minor site having atoms labels with the suffix "B". The methyl carbon atom, C74, was shared between the major and minor sites. The atom was split, then constrained to have identical x, y, z parameters for the major and minor site. Due to the small amount of electron density, the thermal parameters of atoms with "B" labels were constrained to be identical to their chemically identical component. All of the hydrogen atoms associated with disordered atoms were generated geometrically to correspond to the disordered atoms on which they ride. The full numbering scheme of carbocyclinone-534 (4) can be found in the full details of the X-ray structure determination (CIF). CCDC number 1871126 contains certain crystallographic data for this paper. These data can be obtained free of charge from The Cambridge Crystallographic Data Center.

TABLE 1

Crystal data and structure refinement for carbocyclinone-534 (4).

| | |
|---|---|
| Identification code | 007b-18001 |
| Empirical formula | $C_{38} H_{37} N_2 O_{6.50}$ |
| Formula weight | 625.69 |
| Temperature | 93(2)K |
| Wavelength | 1.54184 Å |
| Crystal system | Triclinic |
| Space group | P-1 |
| Unit cell dimensions | a = 12.1644(4) Å   a = 74.489(3)°. |
| | b = 13.2656(5) Å   b = 86.231(2)°. |
| | c = 21.5604(5) Å   g = 82.205(3)°. |
| Volume | 3319.88(19) Å$^3$ |
| Z | 4 |
| Density (calculated) | 1.252 Mg/m$^3$ |
| Absorption coefficient | 0.694 mm$^{-1}$ |
| F(000) | 1324 |
| Crystal size | 0.150 × 0.080 × 0.020 mm$^3$ |
| Crystal color and habit | Colorless Plate |
| Diffractometer | Rigaku Saturn 944+ CCD |
| Theta range for data collection | 2.128 to 66.595°. |
| Index ranges | -13 <= h <= 14, -15 <= k <= 15, -25 <= l <= 25 |
| Reflections collected | 119266 |
| Independent reflections | 11536 [R(int) = 0.0624] |
| Observed reflections (I > 2sigma(I)) | 9605 |

TABLE 1-continued

Crystal data and structure refinement for carbocyclinone-534 (4).

| | |
|---|---|
| Completeness to theta = 66.595° | 98.4% |
| Absorption correction | Semi-empirical from equivalents |
| Max. and min. transmission | 1.00000 and 0.88108 |
| Solution method | SHELXT-2014/5 (Sheldrick, 2014) |
| Refinement method | SHELXL-2014/7 (Sheldrick, 2014) |
| Data/restraints/parameters | 11536/18/896 |
| Goodness-of-fit on F$^2$ | 1.016 |
| Final R indices [I > 2sigma(I)] | R1 = 0.0419, wR2 = 0.1035 |
| R indices (all data) | R1 = 0.0528, wR2 = 0.1101 |
| Largest diff. peak and hole | 0.303 and -0.399 e.Å$^{-3}$ |

TABLE 2

Hydrogen bonds for carbocyclinone-534 (4) [Å and °].

| D-H . . . A | d(D-H) | d(H . . . A) | d(D . . . A) | <(DHA) |
|---|---|---|---|---|
| O(1)-H(1) . . . O(2) | 0.85(3) | 2.13(2) | 2.6282(17) | 116.7(19) |
| O(1)-H(1) . . . N(1) | 0.85(3) | 2.14(2) | 2.882(2) | 145(2) |
| O(4)-H(4) . . . O(5) | 0.89(3) | 2.14(3) | 2.6668(16) | 118(2) |
| O(4)-H(4) . . . O(12)#1 | 0.89(3) | 2.12(3) | 2.8509(17) | 139(2) |
| O(7)-H(7) . . . O(3) | 0.87(3) | 1.96(3) | 2.7384(16) | 148(2) |
| O(7)-H(7) . . . O(9) | 0.87(3) | 2.22(2) | 2.6818(17) | 113(2) |
| O(10)-H(10) . . . O(11) | 0.90(4) | 2.16(3) | 2.6301(18) | 111(3) |
| O(10)-H(10) . . . O(13) | 0.90(4) | 1.96(4) | 2.767(2) | 148(3) |
| O(13)-H(13A) . . . N(4) | 0.85 | 2.14 | 2.990(3) | 176.8 |
| O(13)-H(13B) . . . O(8)#2 | 0.85 | 2.09 | 2.9213(18) | 167 |

Symmetry transformations used to generate equivalent atoms:
1 x + 1, y, z
2 -x, -y + 2, -z + 1

Computational ECD Calculation. The initial conformers for ECD calculation were found at the MMFF94 force field and optimized at the B3LYP/6-31+G(d,p) using the polarizable continuum model (PCM) mode with a dielectric constant representing MeOH, and excited state calculations were performed at the identical theory level and basis set. The generated excitation energies were weighted based upon the Boltzmann population from the calculated Gibbs free energy of each conformer (see Table 3) and fitted with a Gaussian function to visualize the ECD spectrum, utilizing SpecDis.

TABLE 3

Gibbs free energies (kcal/mol) and Boltzmann populations (%) of conformers.

| Conformer | Gibbs free energies | Boltzmann populations |
|---|---|---|
| Carbo A 1 | -1764.63 | 10.7 |
| Carbo A 2 | -1764.63 | 21.5 |
| Carbo A 3 | -1764.63 | 14.0 |
| Carbo A 4 | -1764.63 | 39.8 |
| Carbo A 5 | -1764.63 | 14.0 |

Cloning and Expression of Plu1886. The gene encoding Plu1886 was PCR amplified from *P. luminescens* genomic DNA using the primers noted in Table 5. Following PCR purification, the gene was digested with NdeI/HindIII restriction enzymes and ligated into plasmid pET28a. The ligation reaction was transformed into *E. coli* DH10b, purified, and sequence validated. Purified plasmid encoding Plu1886 with an N-terminal His$_6$ tag was transformed into BL21(DE3) cells for expression. An overnight culture (5 mL) in LB supplemented with kanamycin (50 μg ml$^{-1}$) was subcultured into 1 L of terrific broth (TB) and grown at 37° C. until the OD$_{600}$ reached ~0.5. Protein expression was then induced with 1 mM IPTG and cells were grown overnight at 25° C. Cells were harvested by centrifugation at 5000 rpm for 30 min and resuspended in lysis buffer (50 mM $NaH_2PO_4$, 300 mM NaCl, 10 mM imidazole, 1 mg mL$^{-1}$ lysozyme, pH 8.0). Following incubation on ice for 30 min, cells were lysed via sonication (10 seconds on, 10 seconds off, 2 min total). The lysate was cleared by centrifugation at 30,000×g for 30 min. The supernatant was then incubated with 500 µL Ni-NTA resin with agitation at 4° C. for 1 h. The resin was then washed with 1×5 mL lysis buffer followed by 2×5 mL wash buffer (100 mM Tris, 300 mM NaCl, 50 mM imidazole, 10% glycerol, pH 8.0), and the protein was eluted with 4×500 µL elution buffer (100 mM Tris, 300 mM NaCl, 250 mM imidazole, 10% glycerol, pH 8.0). Fractions were run on SDS-PAGE (FIG. 12) to confirm the presence, size and purity of Plu1886 and were then combined and concentrated.

Enzymatic Assays. Small scale (100 µL) enzymatic assays were prepared with 10 µM enzyme and 1 mM tapinarof in 100 mM sodium phosphate buffer (pH 7.4). Metals ions ($NiCl_2$, $CaCl_2$, $FeSO_4$, $CuSO_4$, $ZnSO_4$, $CoCl_2$, $MgSO_4$, $MnCl_2$) were supplemented at 1 mM. Reactions screening various metals (FIGS. 3B-3C) were incubated at 37° C. overnight. Copper-catalyzed reactions producing 5 were incubated at 37° C. for 2 hours, while manganese-catalyzed reactions producing 4 were incubated at 37° C. overnight. Following incubation, all reactions were lyophilized and extracted with MeOH. Enzymatic products were analyzed by single quadrupole LC/MS using a Phenomenex Kinetix C18 (100 Å) 5 µm (4.6×250 mm) column with the following $H_2O$-ACN gradient containing 0.1% formic acid at a flow rate of 0.7 mL min$^{-1}$: 0-30 min 10-100% ACN, 30-35 min 100% ACN, 35-37 min 10% ACN.

Disk Diffusion Test. Growth inhibitory properties of compounds against *Mycobacterium smegmatis* was performed by the disk diffusion method. *Mycobacterium smegmatis* was grown on an LB agar plate at 37° C. for 72 h. A single colony was inoculated into 5 mL of Middlebrook 7H9 liquid medium and incubated for 48 h. The overnight culture was diluted to $OD_{600}$=0.1 with sterilized medium and a sterile cotton swab was soaked in the diluted culture and streaked on an LB agar plate. Compounds (10 µL of each sample with a concentration of 100 µg/disk) were added to sterile paper disks (7 mm) and allowed to air dry. DMSO (Santa Cruz Biotechnology, Dallas, TX, USA) was used as a vehicle negative control. Paper disks soaked with samples were placed and incubated at 37° C. for 48 h, and the zones of inhibition were then imaged.

Growth Inhibition Assays. Compounds were prepared in DMSO to a concentration of 10 mM. DMSO was used as a vehicle negative control, and vancomycin (MRSA) and ampicillin (VRE) were also prepared as positive controls for minimum inhibitory concentration (MIC) tests. Compounds were tested for antimicrobial activity against MRSA and VRE at 100, 50, 25, 12.5, 6.25, 3.13, 1.56, 0.78, and 0.39 µM. MRSA was grown in tryptic soy broth and VRE was grown in brain heart infusion medium. Overnight cultures of bacteria were diluted to $OD_{600}$=0.1 and 50 µL of cell culture broth was added to each well. Media (50 µL) containing compound at the appropriate concentration was then added to the cell cultures and the plates were sealed and incubated at 37° C. overnight. Plates were then read for $OD_{600}$ using a PerkinElmer Envision 2100 multimode plate reader (PerkinElmer, Waltham, MA, USA). The data was fit to a Gompertz model and MICs were determined as the compound concentration that completely inhibited cell growth during the incubation period. All samples were tested in triplicate.

Antioxidant Activity Assay. Antioxidant activity assay of compounds was evaluated through the DPPH free radical scavenging assay in a 96-well plate. 2,2-diphenyl-1-picrylhydrazyl (DPPH) was purchased (MilliporeSigma, Burlington, MA, USA) and used without further manipulation. Desired compounds and L-ascorbic acid (MilliporeSigma, Burlington, MA, USA) as a positive control were dissolved in DMSO with a concentration of 10 mM. A two-fold serial dilution was initiated in fresh DMSO to eight different concentrations. 10 µL of the serial dilution of the compound was then dispensed to the 96-well plate. 90 µL of freshly prepared 0.2 mM DPPH in methanol was subsequently added to the experimental wells, while 100 µL of MeOH containing DMSO was added to the blank controls. The reactions were stored in the dark for 30 minutes and then measured at 517 nm using a PerkinElmer Envision 2100 multimode plate reader. The $IC_{50}$ (the concentration required to scavenge 50% of radicals) values of tested compounds were calculated using the GraphPad Prism 7 software.

TABLE 4

NMR data of duotap-520 (5) in methanol-$d_4$.

| No | $\delta_C$ | type | $\delta_H$ | Multiplet (J) | COSY | HMBC |
|---|---|---|---|---|---|---|
| 1 | 104.3 | CH | 6.77 | s | | |
| 2 | 152.6 | C | | | | |
| 3 | 121.6 | C | | | | |
| 4 | 156.9 | C | | | | |
| 5 | 113.4 | C | | | | |
| 6 | 134.5 | C | | | | |
| 7 | 126.4 | CH | 6.63 | d (16.1) | 8 | 1, 5, 6, 9 |
| 8 | 129.0 | CH | 6.86 | d (16.1) | 7 | 6, 9, 10, 14 |
| 9 | 137.4 | C | | | | |
| 10 | 125.8 | CH | 7.27 | d (7.6) | | 8, 12, 14 |
| 11 | 128.2 | CH | 7.24-7.17 | m | | 9, 13 |
| 12 | 127.1 | CH | 7.14 | t (7.2) | | 10, 14 |
| 13 | 128.2 | CH | 7.24-7.17 | | | 9, 11 |
| 14 | 125.8 | CH | 7.27 | d (7.6) | | 8, 10, 12 |
| 15 | 24.6 | CH | 3.51 | h (7.0) | 16,17 | 2, 3, 4, 16, 17 |
| 16 | 19.5 | $CH_3$ | 1.33 | d (7.0) | 15 | 3, 15, 17 |
| 17 | 19.5 | $CH_3$ | 1.33 | d (7.0) | 15 | 3, 15, 16 |
| 1' | 183.8 | C | | | | |
| 2' | 152.7 | C | | | | |
| 3' | 125.4 | C | | | | |
| 4' | 187.3 | C | | | | |
| 5' | 141.1 | C | | | | |
| 6' | 136.1 | C | | | | |
| 7' | 120.5 | CH | 6.68 | d (16.5) | 8' | 1', 5', 6', 8', 9' |
| 8' | 138.7 | CH | 7.49 | d (16.5) | 7' | 6', 7', 9', 10', 14' |
| 9' | 137.4 | C | | | | |
| 10' | 126.5 | CH | 7.24-7.17 | | | |
| 11' | 128.2$^a$ | CH | 7.24-7.17 | | | |
| 12' | 126.5$^a$ | CH | 7.24-7.17 | | | |
| 13' | 128.2$^a$ | CH | 7.24-7.17 | | | |
| 14' | 126.5 | CH | 7.24-7.17 | | | |
| 15' | 24.4 | CH | 3.25 | m | 16', 17' | 2', 3', 4', 16', 17' |
| 16' | 19.0 | $CH_3$ | 1.25-1.23 | | 15' | 3', 15', 17' |
| 17' | 19.0 | $CH_3$ | 1.25-1.23 | | 15' | 3', 15', 16' |

$^a$not assignable

Figure 1B:
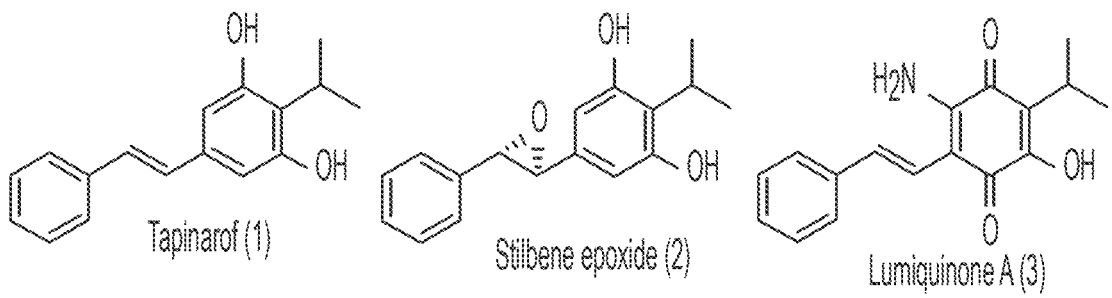
FIG. 1B shows the structures of tapinarof (1), stilbene epoxide (2), and lumiquinone A (3).
Figure 6:
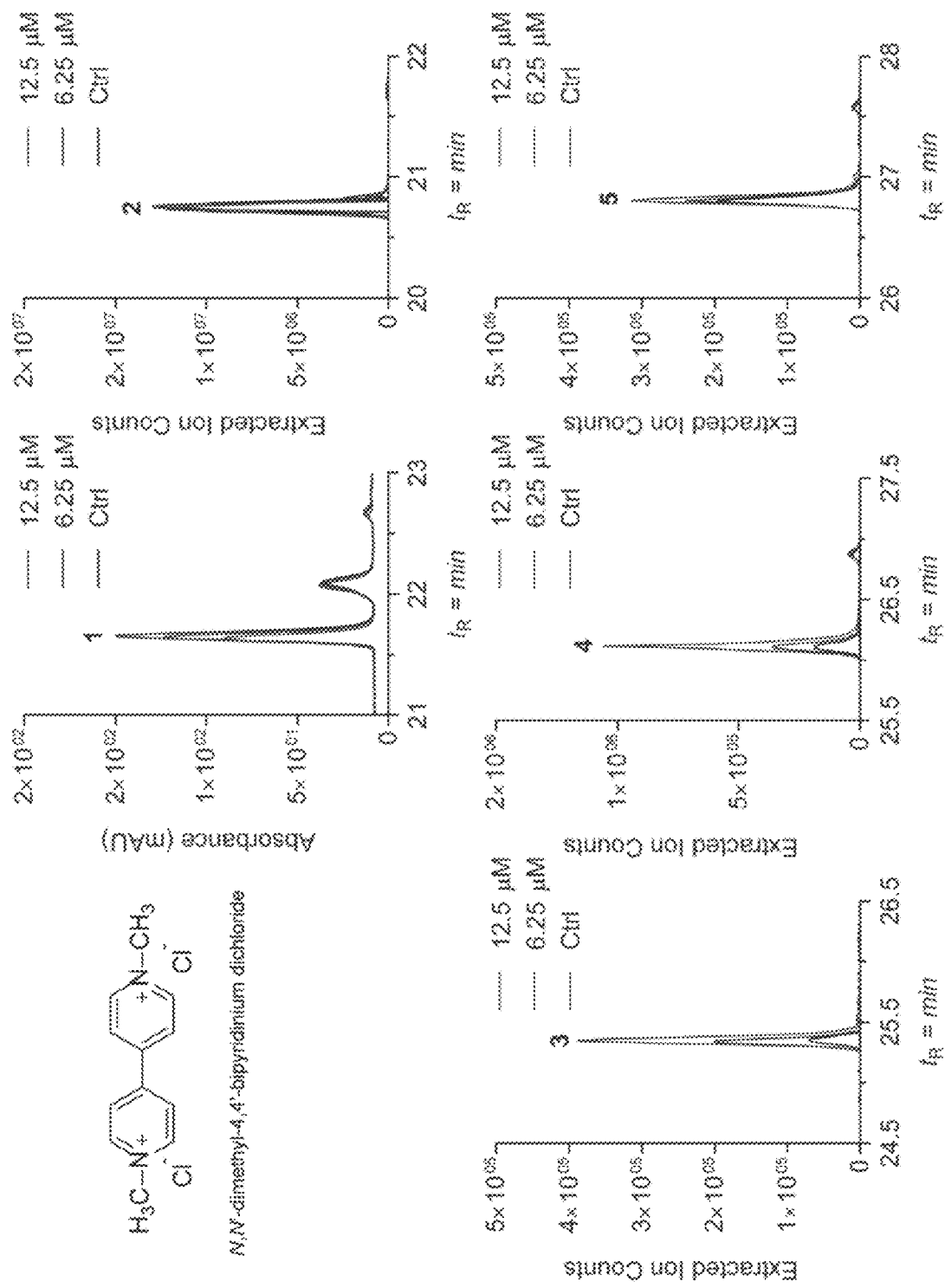
FIG. 6 shows the comparative UV-LC-HRMS profiles for five metabolites 1-5 from *P. luminescens* in response to sublethal paraquat-induced redox stress. UV traces of 1 measured at 254 nm and extracted ion counts (EICs) representing the calculated mass of the positively charged metabolites 2-5 are shown in the same scale of y axis. Structure of paraquat is shown at the top left, and numbers of compounds are noted in bold. Samples prepared in biological triplicates were analyzed using a reversed-phase $C_{18}$ HPLC analytical column (Phenomenex Kinetex $C_{18}$ (100 Å) 5 µm (4.6×250 mm) with a linear gradient from 10 to 100% aqueous ACN in 0.1% formic acid over 30 min with a flow rate of 0.7 mL $min^{-1}$.
Figures 7A, 7B:
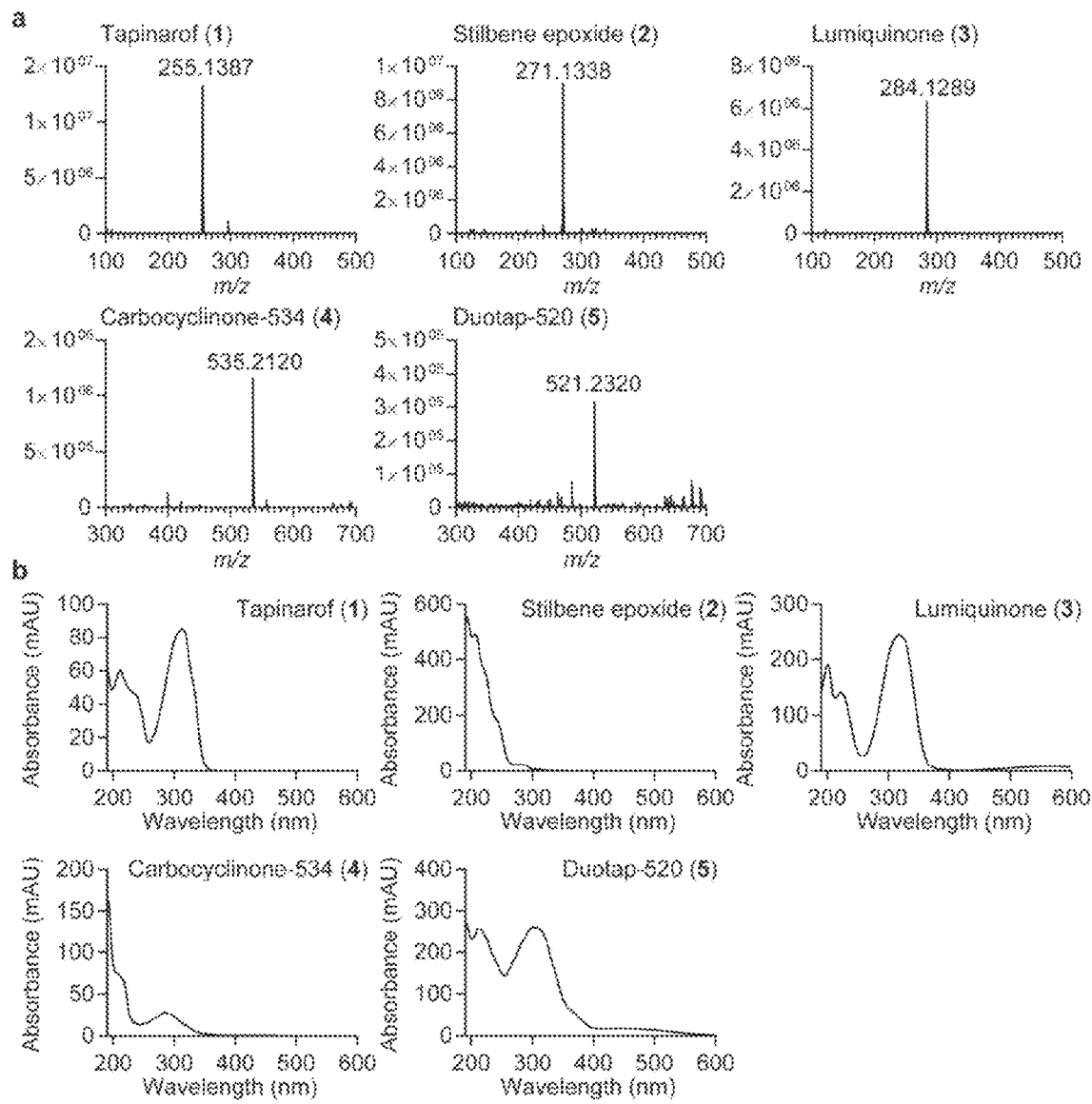
FIGS. 7A and 7B shows the HR-ESI-QTOF-MS spectra (7A) and UV-visible (7B) spectra of metabolites 1-5.

*Photorhabdus* Metabolites Are Induced in Response to Redox Cell Stress. During infections, bacteria respond to a myriad of cellular stresses derived from the host such as redox stress. *Photorhabdus* pathogenicity is associated with the rich circulatory system of infected hosts. Thus, *P. luminescens* was initially challenged to redox stress in a nutrient-rich background. Redox stress was induced by supplementation of sub-inhibitory concentrations of paraquat (1,1'-dimethyl-4,4'-bipyridinium dichloride), which generates reactive oxygen species (ROS) (FIG. 6). Specifically, wild-type P. luminescens was cultivated in lysogeny broth (LB) supplemented with paraquat (12.5 and 6.25 µM) and the cultures compared to non-stressed controls under aerobic conditions at 30° C. until they reached stationary phase (48 h, FIG. 1A). Ethyl acetate extracts of the cultures were analyzed by high-resolution ESI-QTOF-LC-MS (FIG. 6). Relative to the paraquat-free cultures, extracted ion count (EIC)-based LC-MS data of redox-stressed cultures revealed stimulation of three distinct peaks with complex UV-visible chromophores eluting at $t_R$=25.4 (3), 26.1 (4), and 26.8 (5) min (FIG. 1A and FIG. 6). The high-resolution mass data ([M+H]$^+$ m/z 284.1289, 535.2120, and 521.2320) suggested the molecular formulas of 3, 4, and 5 to be $C_{17}H_{17}NO_3$, $C_{34}H_{30}O_6$, and $C_{34}H_{32}O_5$, respectively (FIGS. 7A-7B). Through the analysis of UV-visible chromophores corresponding to 3-5 and comparison to the prior analysis, 3 was demonstrated to be a previously known amino-substituted tapinarof derivative, lumiquinone A, while 4 and 5 were not consistent with those of previous stilbene-derived metabolites (FIGS. 7A-7B). Since lumiquinone A (3) is related to tapinarof, the comparative responses of the two major Photorhabdus stilbenes, tapinarof (1) and its epoxidation product 2 (FIGS. 1A-1B) were also analyzed. While the production levels of 2 ($t_R$=20.7 min) were unaffected, 1 ($t_R$=21.6 min) was significantly decreased in a dose-dependent manner, indicating an inverse correlation between 1 and 3-5 in their production (FIGS. 1A, 1B, and 6).

Figure 1C:
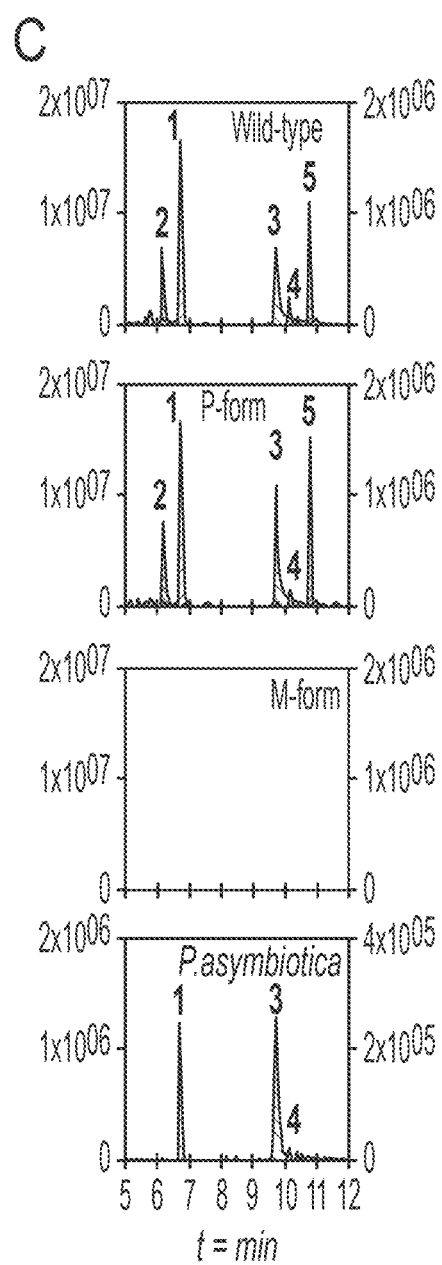
FIG. 1C shows representative EICs of metabolites 1-5 from ethyl acetate-soluble extracts from cultures of *P. luminescens* wild-type (top), genetically locked P- and M-forms (middle), and *P. asymbiotica* (bottom). The scale of y axis on the left: relative intensity of 1 and 2. Right: relative intensity of 3-5. LC/HRMS-QTOF data were analyzed in three independent experiments using a gradient from 50 to 100% aqueous acetonitrile containing 0.1% formic acid over 15 min with a 0.7 mL min$^{-1}$ solvent flow rate.
Figure 8:
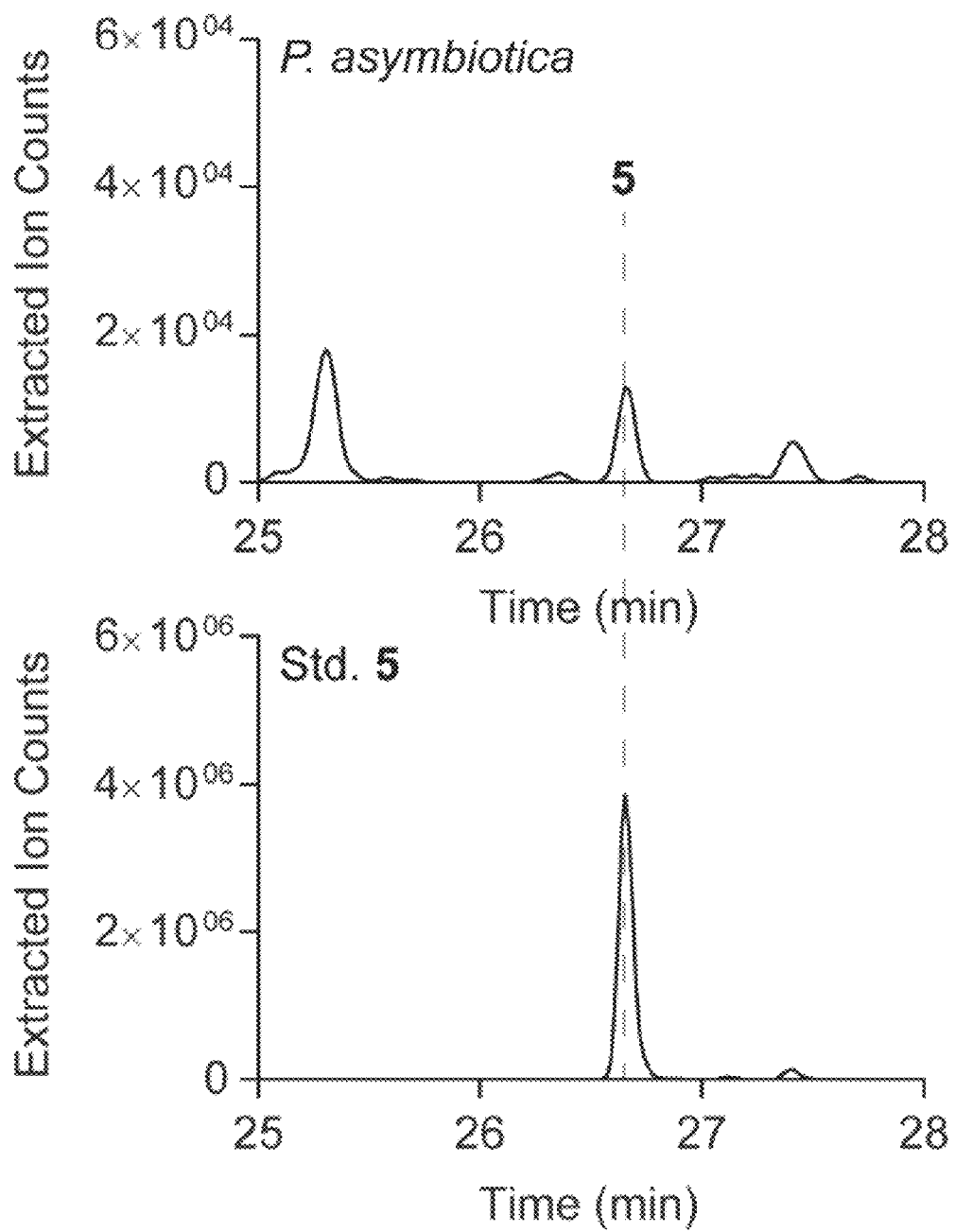
FIG. 8 illustrates the detection of duotap-520 (5) from the 1-liter culture of *P. asymbiotica*.
Figure 9:
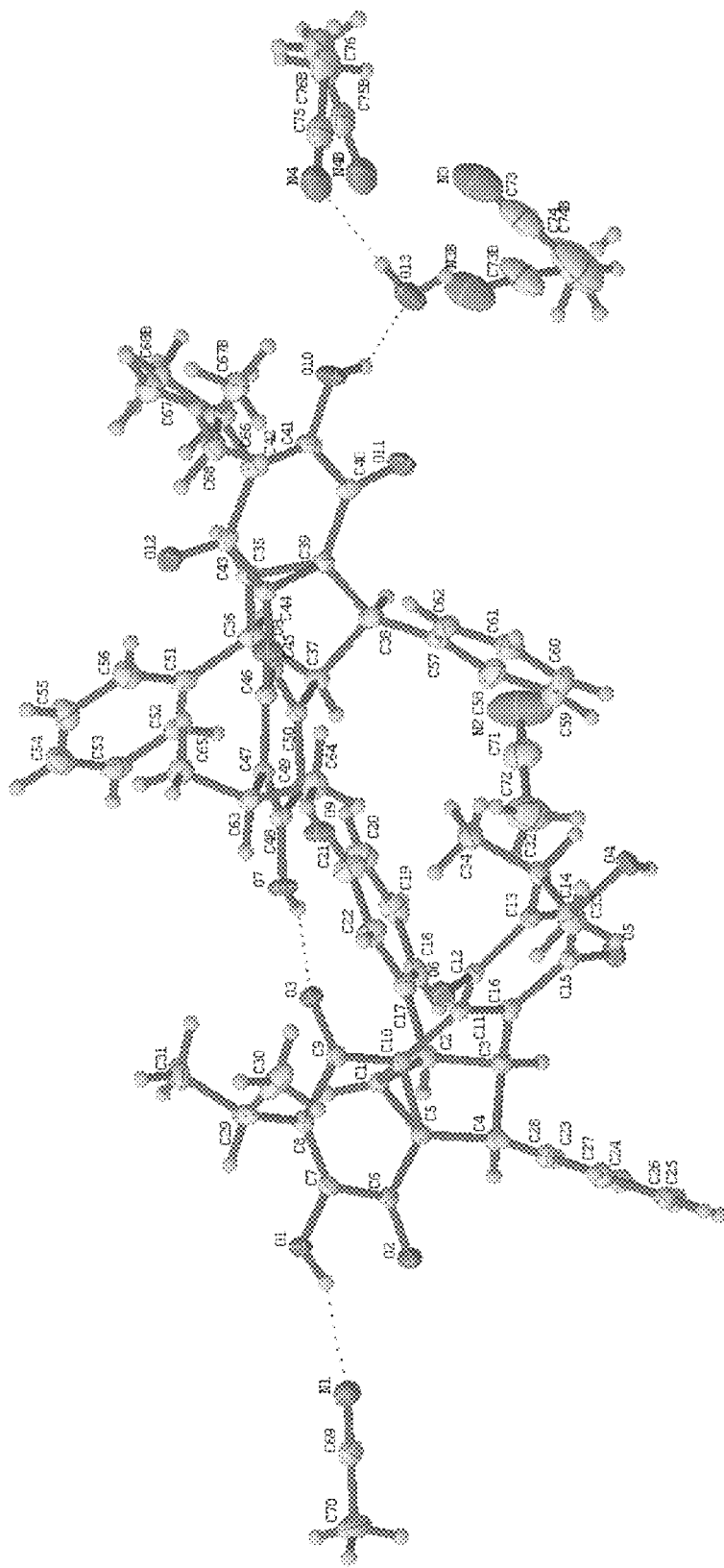
FIG. 9 shows the numbering scheme of carbocyclinone-534 (4) with 50% thermal ellipsoid probability levels. The hydrogen atoms are shown as circles for clarity.
Figure 10:
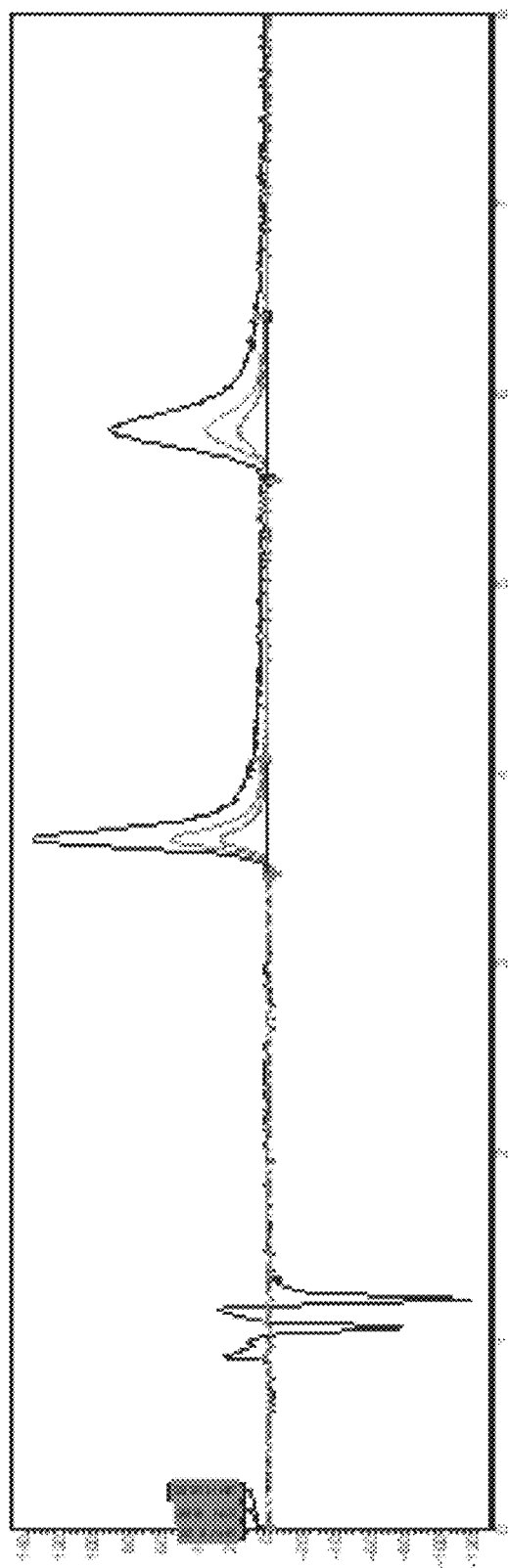
FIG. 10 shows the HPLC separation trace of a racemic carbocyclinone-534 (4). The racemic mixture 4 was separated on an AD-H column (2×25 cm; eluted with 30% isopropanol/$CO_2$ in 0.1% DEA; 60 mL $min^{-1}$) to obtain (+)-4 (3.0 mg, $t_R$=3.48 min) and (−)-4 (1.0 mg, $t_R$=5.45 min). Analytical method is as follows: Column; AD-H (0.46×25 cm; eluted with 30% isopropanol/$CO_2$ in 0.1% DEA; 3 mL $min^{-1}$).

The production of these metabolites was examined in two genetically-locked strains of P. luminescens, in which the M- and P-forms do not stochastically interconvert, to unambiguously evaluate the contributions of bacterial phase variation on metabolite production. $C_{18}$-reversed-phase LC-MS analysis of the extracts demonstrated that the entire family of metabolites were only produced in the P-form associated with pathogenesis and they were undetectable in the M-form cultures (FIG. 1C). A clinical isolate of P. asymbiotica was cultivated, and 1, 3, and 4 were readily detected, whereas 2 and 5 were below detection limits under the conditions of the small-scale experiments (FIG. 1C). A larger-scale culture of P. asymbiotica in LB medium led to detectable levels of 5 (FIG. 8).

Figure 2A:
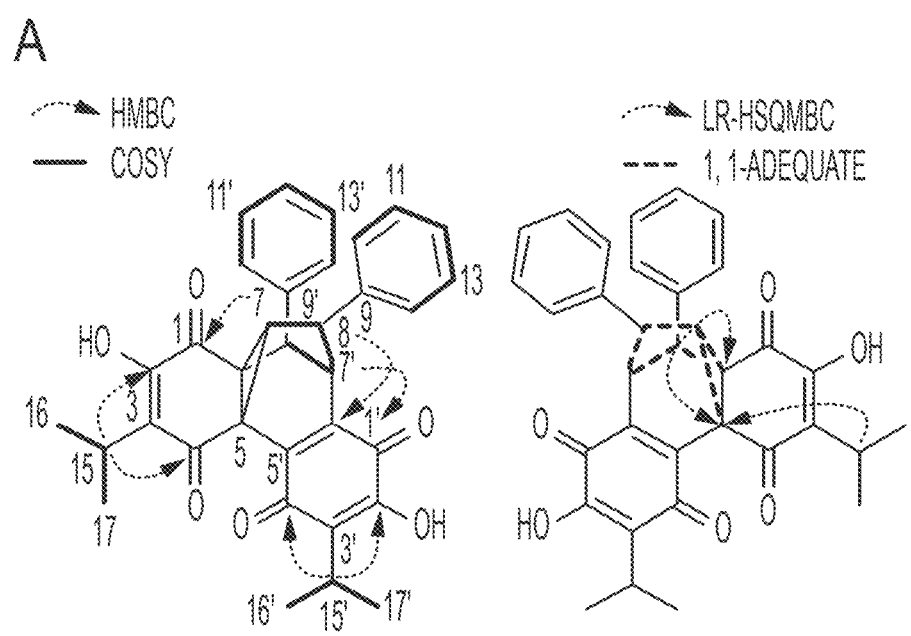
FIG. 2A shows two-dimensional NMR correlations for the structural assignments of 4.

Structural Characterization of Metabolites 4 and 5. To isolate sufficient amounts of material for biological analysis and elucidate the structures of 4 and 5, P. luminescens was cultivated on a 100-liter scale. These metabolites were extracted with ethyl acetate and the materials were purified using HPLC, leading to homogeneous 4 and 5. The structure of 4 was fully characterized by extensive interpretation of 1D ($^1$H, $^{13}$C, and 1D-NOESY) and 2D (H-$^1$H gCOSY, $^1$H-$^{13}$C gHSQCAD, $^1$H-$^{13}$C gHMBCAD, LR-HSQMBC, 1,1-ADEQUATEAD, and ROESYAD) NMR data. $^1$H, $^{13}$C, and gHSQCAD NMR spectra of 4 enabled the assignment of all of the protons to their directly bonded carbons (16×CH and 4×CH$_3$) and identification of fourteen additional quaternary carbons. The interpretation of COSY cross-peaks established three distinguishable fragments: two phenyl rings, two isopropyl groups, and an aliphatic moiety (C-7/C-8/C-7'/C-8') (FIG. 2A). Importantly, four-bond long range COSY correlations between H-10/H-14 and H-8, and H-10'/H-14' and H-8' indicated that C-8 and C-8' are directly connected to the two phenyl rings. The $^3J_{CH}$ HMBC cross-peaks from a methine H-15 to a ketocarbonyl C-4 and a quaternary carbon C-2 functionalized with a hydroxyl group, and from H-7 to two ketocarbonyls C-1 and C-4 constructed a moiety of 2-hydroxy-3-isopropylcyclohexene-1,4-dione. Similarly, a benzoquinone motif was built by the $^3J_{CH}$ HIMBC cross-peaks from H-15' to C-2' and C-4', and from H-7' to C-1' and C-5'. Finally, key HMBC correlations from a methine H-7 to C-1, C-4, C-7' and C-8' led to the construction of a complex 6/3/5/6/6/6-ring system in 4 (FIG. 2A), which was further supported by a LR-HSQMBC experiment capable of displaying long range heteronuclear correlations (i.e., $^4J_{CH}$ and/or $^5J_{CH}$). The existence of a cyclopropane motif in 4 was confirmed by the 1,1-ADEQUATEAD ($^1J_{CC}$=10 Hz) NMR correlations from a methine proton H-7 to two quaternary carbons C-4 and C-5 (FIG. 2A, FIG. 6). Thus, the structure of 4 was characterized to be a novel tapinarof-derived dimer representing a complex hexacyclic framework, which was named carbocyclinone-534 (4). The relative structure of 4 was supported by the interpretation of 2D ROESYAD and 1D NOESY combined with an analysis of measured interproton distance (2.3 Å) in solution between H-8 and H-8', using the peak amplitude normalization for improved cross-relaxation (PANIC) method.

Figure 2B:
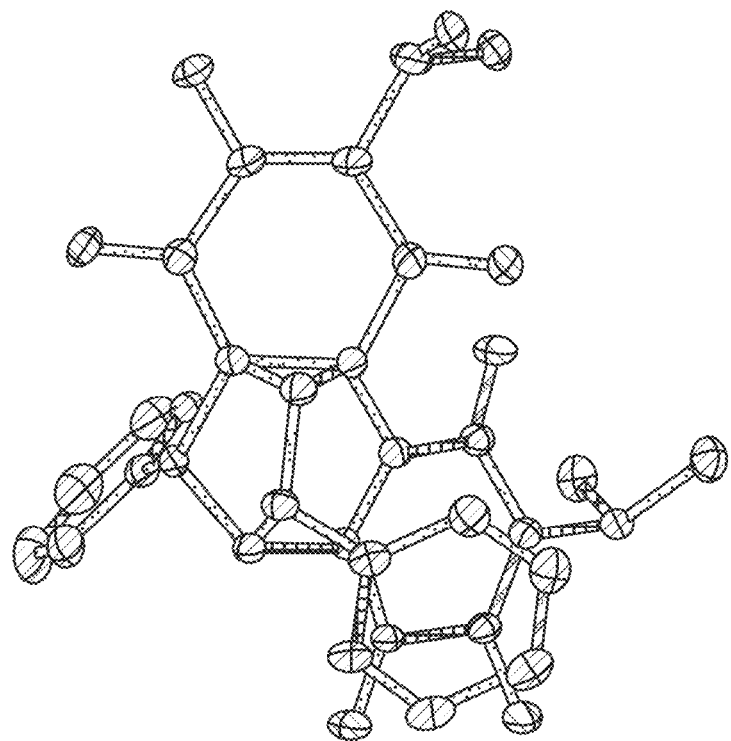
FIG. 2B shows ORTEP drawing of X-ray crystal structure of 4.
Figure 2B:
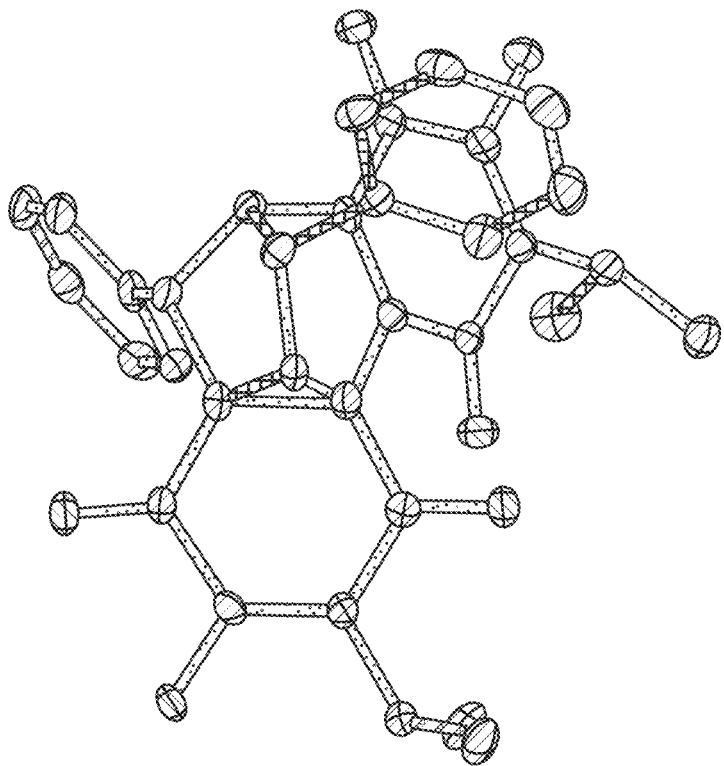
Figure 2C:
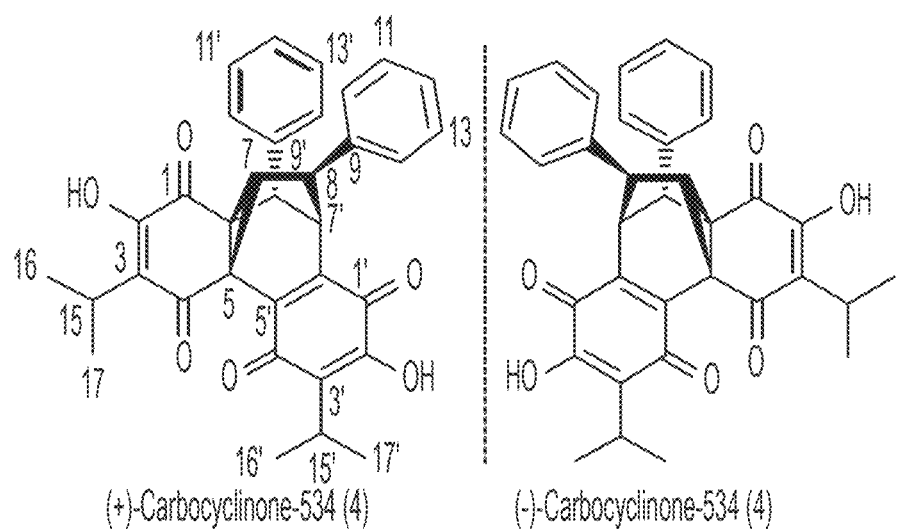
FIG. 2C shows a mirror image structure of 4.
Figure 2D:
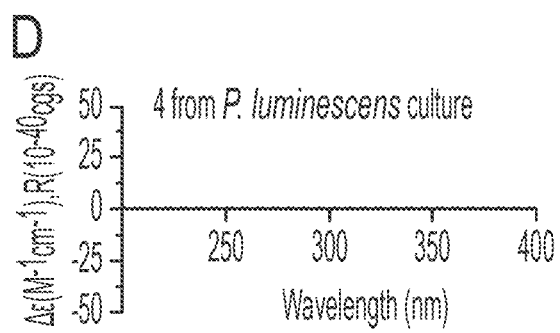
FIG. 2D shows the ECD spectrum of 4 isolated from ethyl acetate extracts of *P. luminescens* culture supernatant.
Figure 2E:
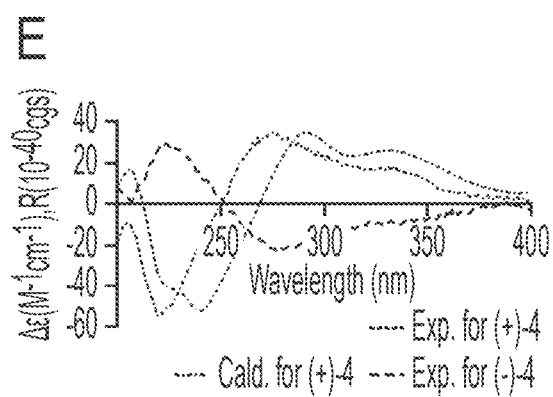
FIG. 2E shows the experimental ECD spectra of optically active 4 purified by chiral-phase chromatography, and ECD comparison of the calculated spectrum of (+)-4 in methanol at the B3LYP/6-31+G(d,p) level and its experimental spectrum.

The complex structure of 4 prompted us to confirm the NMR-based assignments through X-ray crystallography; 4 was successfully crystallized in a combination of water and acetonitrile (a ratio of 1:1) under slow solvent evaporation at 4° C. Single crystal X-ray diffraction analysis conducted with Cu Kα radiation (λ=1.54178 Å) unambiguously supported the absolute structure of 4, and established 4 as a racemic mixture (FIG. 2B and Tables 1-2). Consistent with X-ray crystallographic analysis, the ECD spectrum of 4 had no Cotton effects (FIG. 2D). Thus, 4 was further purified by chiral phase separation, and the corresponding enantiomers (+)-4 ([α]$_D^{25}$+3.5, c 0.01, CH$_3$OH) and (−)-4 ([α]$_D^{25}$−4.7, c 0.01, CH$_3$OH) were isolated in a ratio of ca. 1.2:1 (FIG. 2E). The absolute configurations of (+)-4 and (−)-4 were finally defined as 5R,6S,7R,8S,7'R,8'S and 5S,6R,7S,8R,7'S,8'R, respectively (FIG. 2C), by comparing the experimental and calculated ECD spectra simulated by Gaussian 09 (FIG. 2E and Table 3).

Figure 2F:
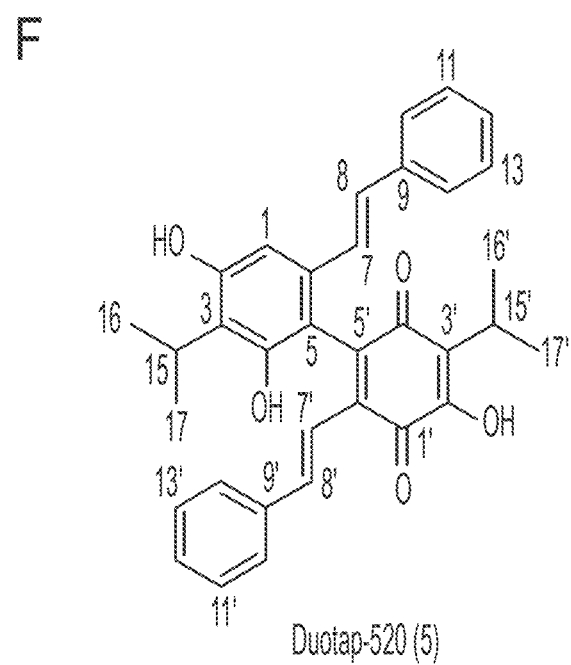
FIG. 2F shows the structure of 5.
Figures 11A, 11B:
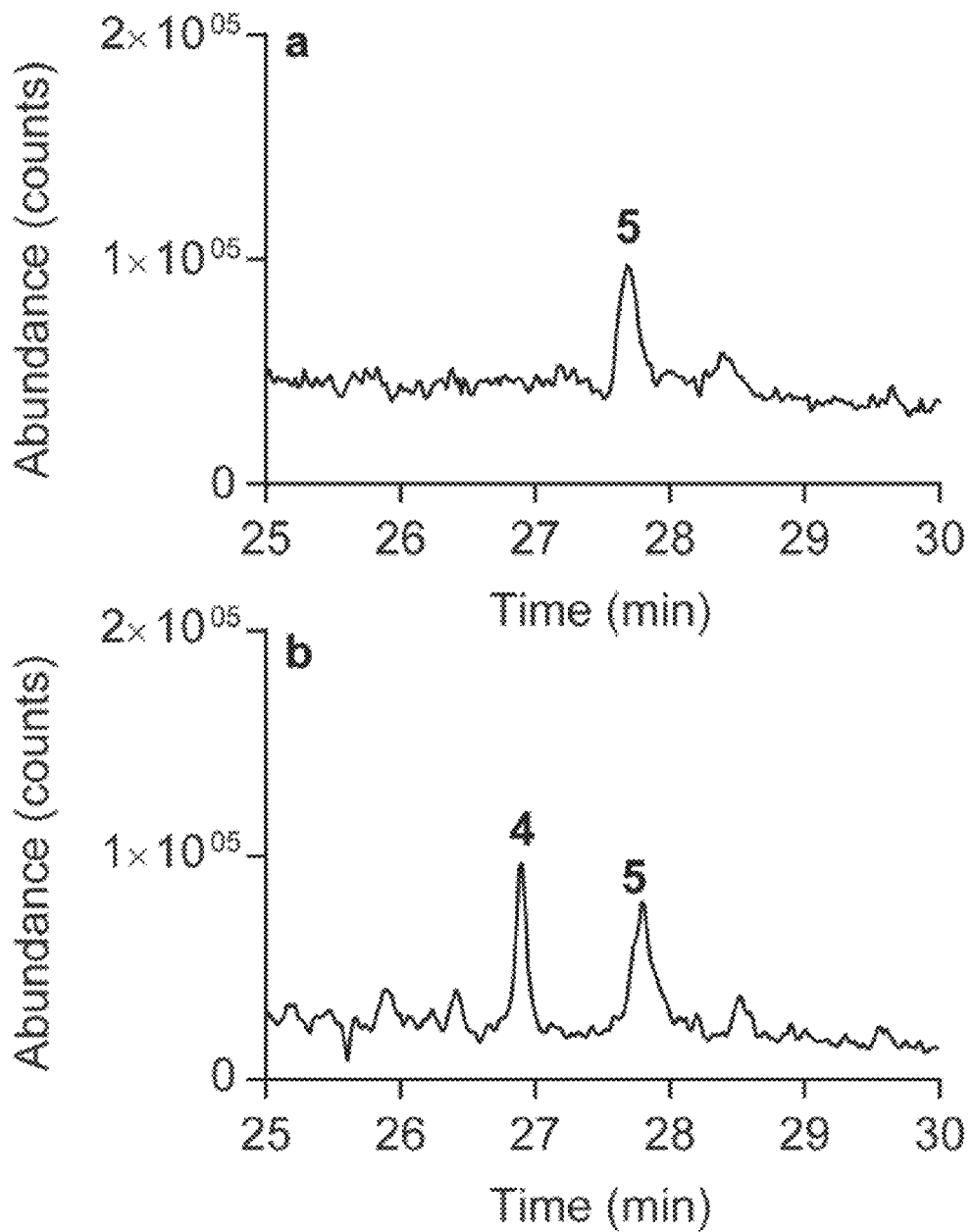
FIGS. 11A and 11B show the slow conversion of duotap-520 (5) to carbocyclinone-534 (4).

The $^1$H NMR data of 5 (Table 4) were closely related to those of 1, suggesting 5 is another type of dimerization product of 1. Interpretation of 2D-(gCOSY, gHSQCAD, and gHMBCAD) NMR spectra of 5 enabled the construction of two distinctive monomeric partial structures, including a tapinarof and a quinone analogue of tapinarof. The two units were directly connected by a C—C bond linkage, which was evident by key HMBC cross-peaks from H-1 to C-5, and from H-7' to C-5', yielding a new heterodimer of tapinarof, which was named duotap-520 (5) (FIG. 2F). The structure was finally supported by the molecular formula ($C_{34}H_{32}O_5$) deduced from the HR-ESI-QTOF-MS data ([M+H]$^+$ m/z 521.2320, calcd 521.2321). Comprehensive analyses of NMR, X-ray crystallography, ECD, and computational data of new molecules 4 and 5 supported them as tapinarof drug metabolism products. Under aerobic conditions, 5 could be slowly converted to 4 (FIGS. 11A and 11B). Stilbene dimers are commonly found in plants and possess a wide range of biological activities. Various structural motifs such as benzofuran, dibenzocycloheptanoid, dibenzooctahydropentalene, and tetraarylfuran have been formed by dimerization and/or polymerization of stilbene monomers. The current findings of the tapinarof dimers expand the stilbene structural repertoire.

Figures 3A, 3B, 3C, 3D, 3E, 3F:
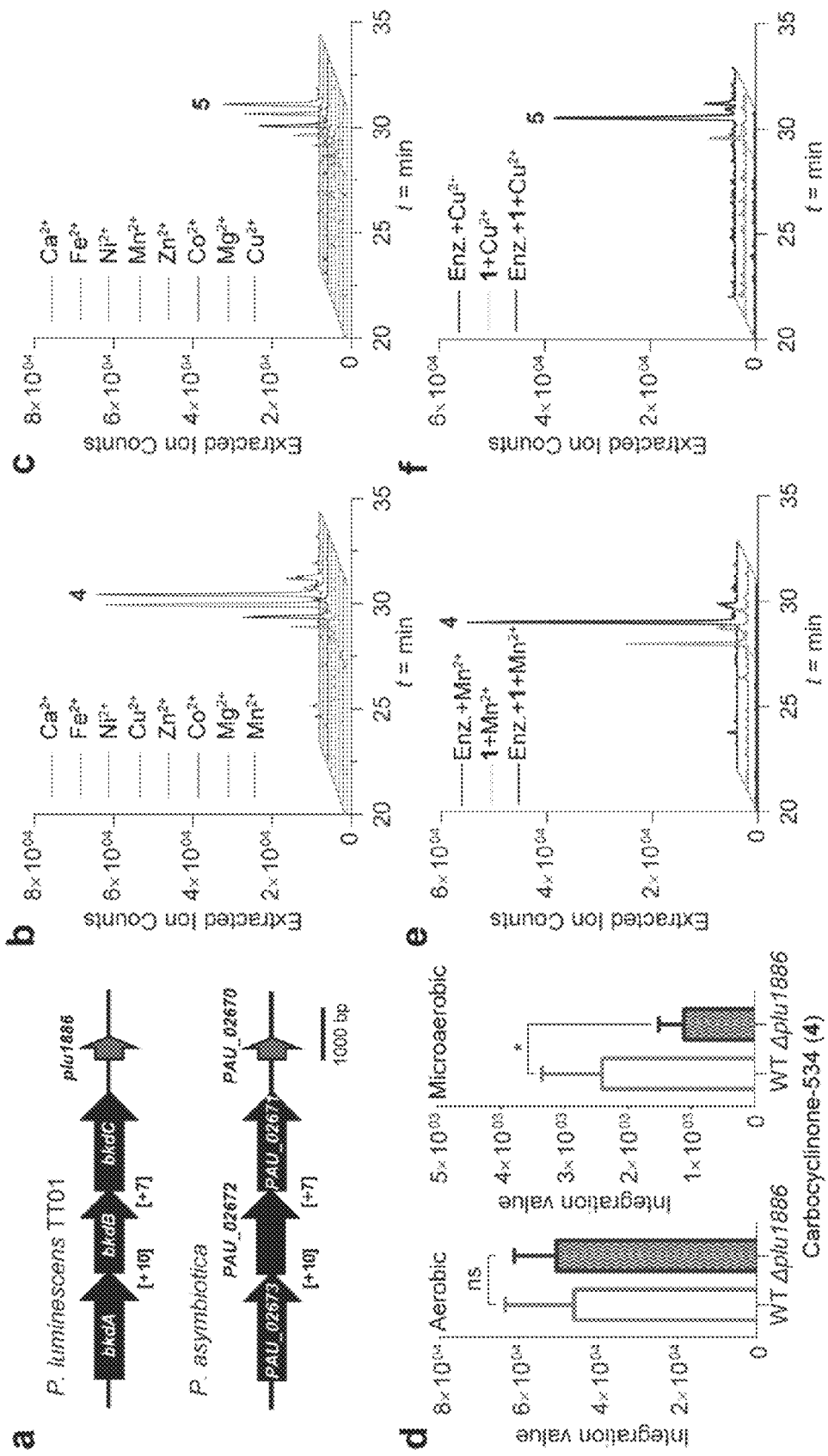
FIG. 3A shows the annotation of Plu1886 adjacent to known tapinarof biosynthetic genes and synteny with *P. asymbiotica*.
FIGS. 3B and 3C show extracted ion chromatograms of enzyme reactions showing relative production of 4 and 5 with varying metal ion supplements.
FIG. 3D shows production of 4 between wild-type *P. luminescens* and Δplu1886 in aerobic and microaerobic culture conditions. Data are mean±SEM for six biological replicates. *P<0.05 by two-tailed student's t-test. ns indicates not-significant.
FIGS. 3E and 3F show extracted ion counts of m/z 535 and 521 corresponding to 4 and 5 from in vitro reactions with tapinarof (1) in the presence and absence of Plu1886.

An Orphan Bacterial Cupin Enzyme Catalyzes Regioselective Dimerization of Tapinarof. Enzymatic oxidative dimerization of natural stilbenes has previously been described. For example, plant peroxidases are responsible for converting monomeric trans-resveratrol into dimeric δ- and ε-viniferin by forming a benzofuran core. Similarly, it has been shown that a laccase-like stilbene oxidase encoded by necrotrophic fungi utilizes plant polyphenols to produce polymerization products. Given the resorcinol moiety in 1, it was also anticipated that a facile oxidation process could lead to the dimerization of 1 to yield 4 and 5 (Compound 1). To support this, the tapinarof biosynthetic gene cluster encoded in the genomes of *P. luminescens* TT01 and *P. asymbiotica*, which is fragmented into at least four regions of the genome, was evaluated. Using similar genome context, a separate clustered gene involved in the stereoselective epoxidation of tapinarof to 2 was previously identified. In this study, focus was on gene plu1886 that encodes a candidate cupin-type enzyme and is located adjacent to bkdC (plu1885), a ketosynthase that participates in tapinarof biosynthesis. Genome synteny analysis revealed that Plu1886 is conserved in *Photorhabdus* species including *P. asymbiotica* (FIG. 3A). Proteins in the cupin superfamily are widespread in plants and are known to catalyze diverse oxidation reactions.

TABLE 5

Oligonucleotide primers used for cloning of Plu1886.

| Primer Name | Sequence |
| --- | --- |
| 1886-F | 5'-GAATTCCATATGGAATTTAT TAAAAATAGATTTTGTCACTGGA ACGG-3' |
| 1886-R | 5'-GAATTCAAGCTTTTAAACCT TTAATTCCTCTGGCGTT CCC-3' |

Figure 12:
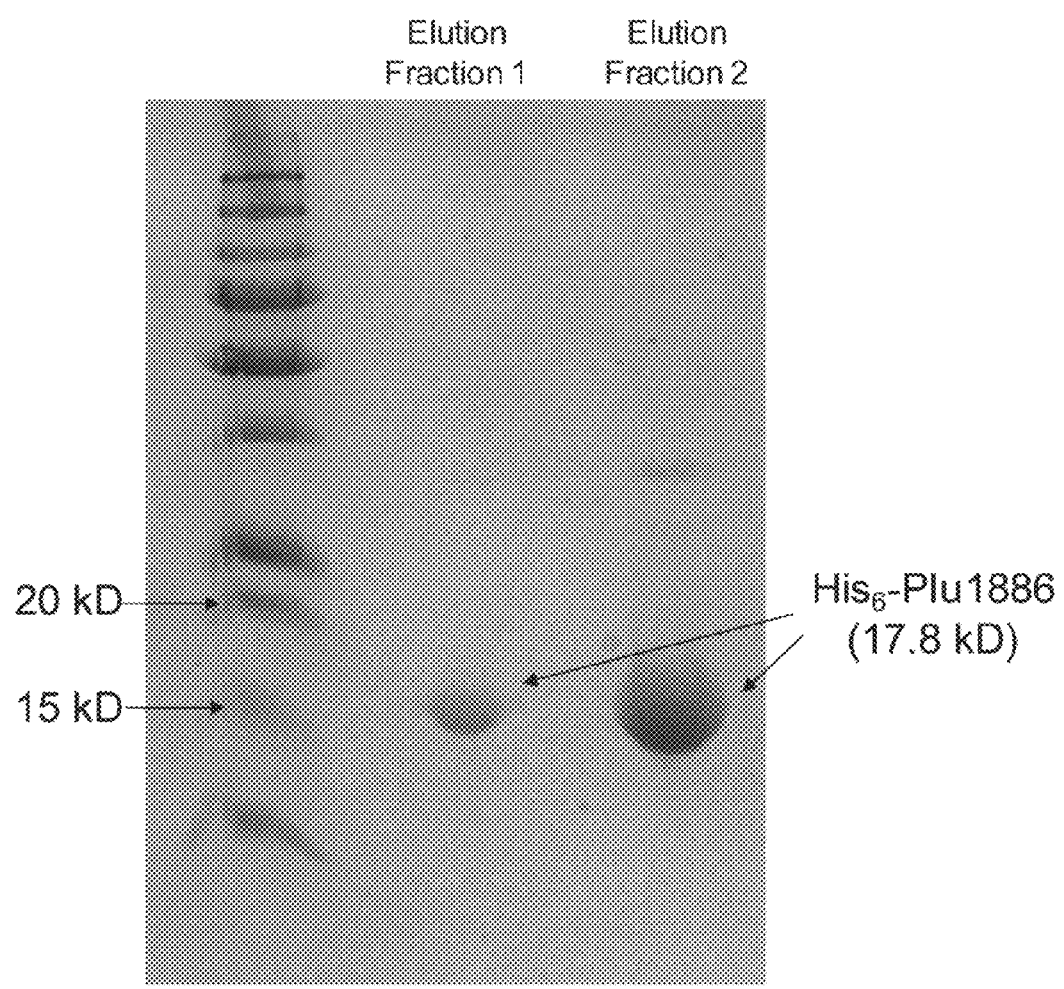
FIG. 12 shows the SDS-PAGE gel of elution fractions from the purification of $His_6$-Plu1886.

To establish function of Plu1886 in vitro, an N-terminal His$_6$-tagged-Plu1886 variant was cloned, overexpressed, and purified (Table 5 and FIG. 12). Oligonucleotide primers used in cloning of the N-terminal His$_6$-tagged-Plu1886 variant included primer 1886-F (SEQ ID NO: 2) and 1886-R (SEQ ID NO: 3). Preparative biochemical reconstitution of isolated Plu1886 was carried out on 100 µL scale reactions supplemented with 1 mM substrate 1 and 10 µM Plu1886 at 37° C. Because oxidative cupin enzymes frequently use metal ions to catalyze reactions, eight different metal supplements ($Ni^{2+}$, $Ca^{2+}$, $Fe^{2+}$, $Cu^{2+}$, $Zn^{2+}$, $Co^{2+}$, $Mg^{2+}$, and $Mn^{2+}$) were tested at 1 mM for their effects on the in vitro activity of Plu1886. Following incubation, the reactions were lyophilized, extracted with methanol, and analyzed by LC-MS. EIC analysis of the reactions demonstrated conversion of substrate 1 into 4 and 5 in the presence of various metals, with highest production of 4 in the presence of $Mn^{2+}$ and of 5 in the presence of $Cu^{2+}$ (FIGS. 3B, 3C). The ECD spectrum of purified enzymatic product 4 also showed no Cotton effects, which is consistent with the naturally isolated racemic mixture of 4 (FIG. 3D). While some spontaneous production of 4 and 5 occurs in the presence of metal supplements under the conditions of the experiments, significant enzyme-dependent enhancements (FIGS. 3E and 3F) were observed. Product 5 was prepared at earlier incubation times (2 h incubation shown), while 4 accumulated only at later time points (overnight incubation shown). The cupin protein appears to bifurcate regioselective dimerization of 1 to 4 or 1 to 5 in a redox-active metal-dependent manner. While the biological roles of this metal dependency remain undefined, it is intriguing that human blood and serum, as well as insect circulatory fluid, are enriched in copper.

Figure 4:
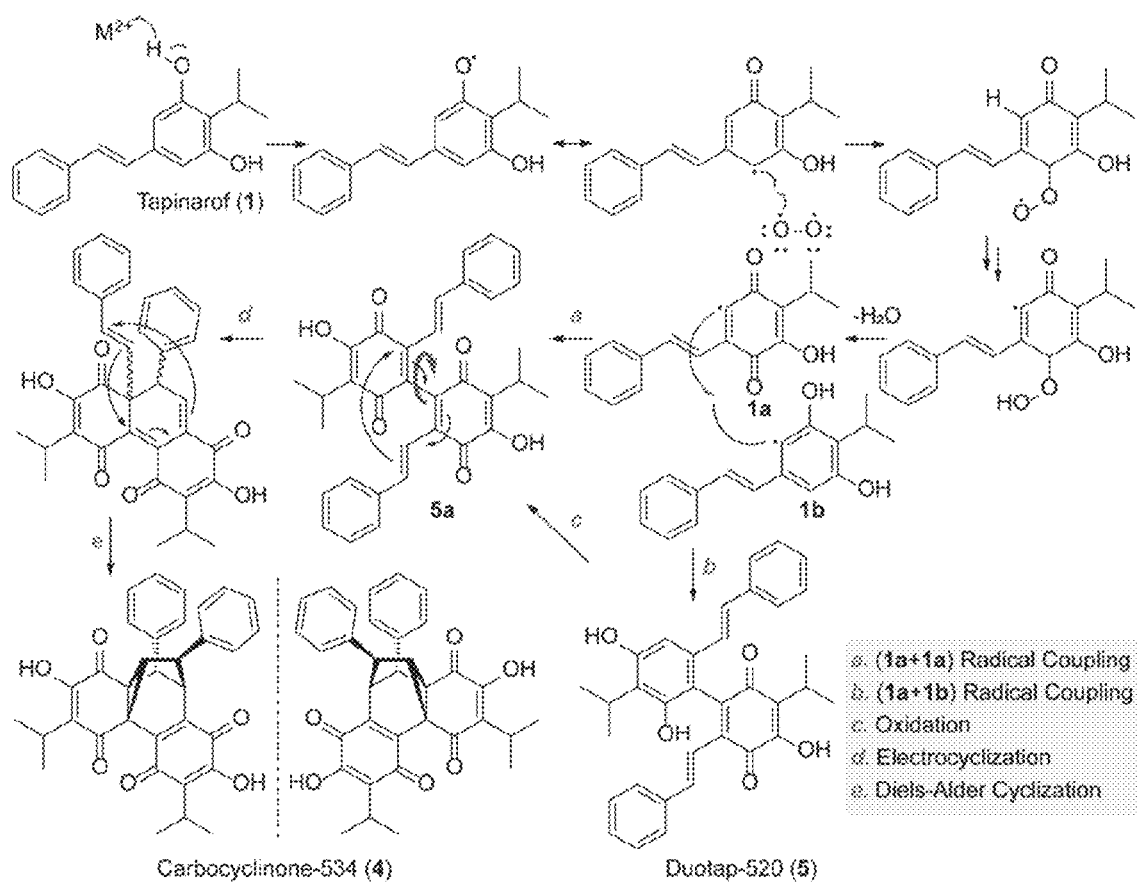
FIG. 4 illustrates the proposed pathway of carbocyclinone-534 (4) and duotap-520 (5) via regioselective dimerization of tapinarof (1).
Figure 13:
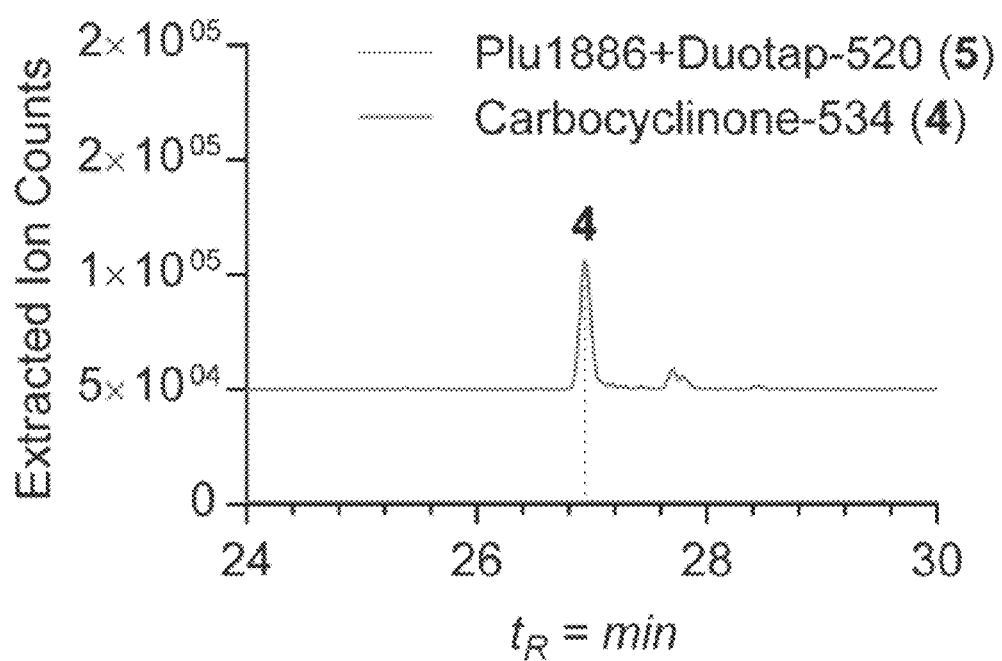
FIG. 13 shows a representative trial of in vitro production of carbocyclinone-534 (4) from the supplementation of duotap-520 (5) in the presence of Plu1886 at 37° C. for overnight. Red line indicates the EIC data of pure compound carbocyclinone-534 (4) and blue line indicates the EIC data of in vitro reaction of duotap-520 in the presence of Plu1886.

Proposed Biosynthesis of Metabolites 4 and 5. Based on the structural and protein biochemical studies, a biosynthesis of 4 and 5 via an oxidative dearomatization route was proposed (FIG. 4). Plu1886 could abstract a hydrogen atom from the resorcinol ring in 1 to form a semiquinone radical, which could undergo a peroxidation sequence in the presence of molecular oxygen. Peroxide decomposition and radical rearrangement to 1a followed by dimerization with a second equivalent of 1a could construct the unstable homodimeric benzoquinone intermediate 5a, which was not detected in the screens. This enzyme product could undergo a spontaneous facile electrocyclization followed by a Diels Alder cyclization to set the cyclopropane ring, leading to the final racemic product 4. In contrast, coupling of monomers 1b and 1a could yield heterodimeric 5, which can slowly oxidize to 4 via 5a (FIG. 4). Of note, 5 was not a substrate of Plu1886 in the formation of 4, suggesting bifurcation at the monomeric coupling step depending on metal supplement (FIG. 13). Chemical oxidation of 1 using 3 mmol $KMnO_4$ followed by reflux for 30 min in water[61] yielded multiple uncharacterized oxidation products including dimers, but none of them correlated with 5 (data not shown).

Figures 5A, 5B, 5C, 5D, 5E:
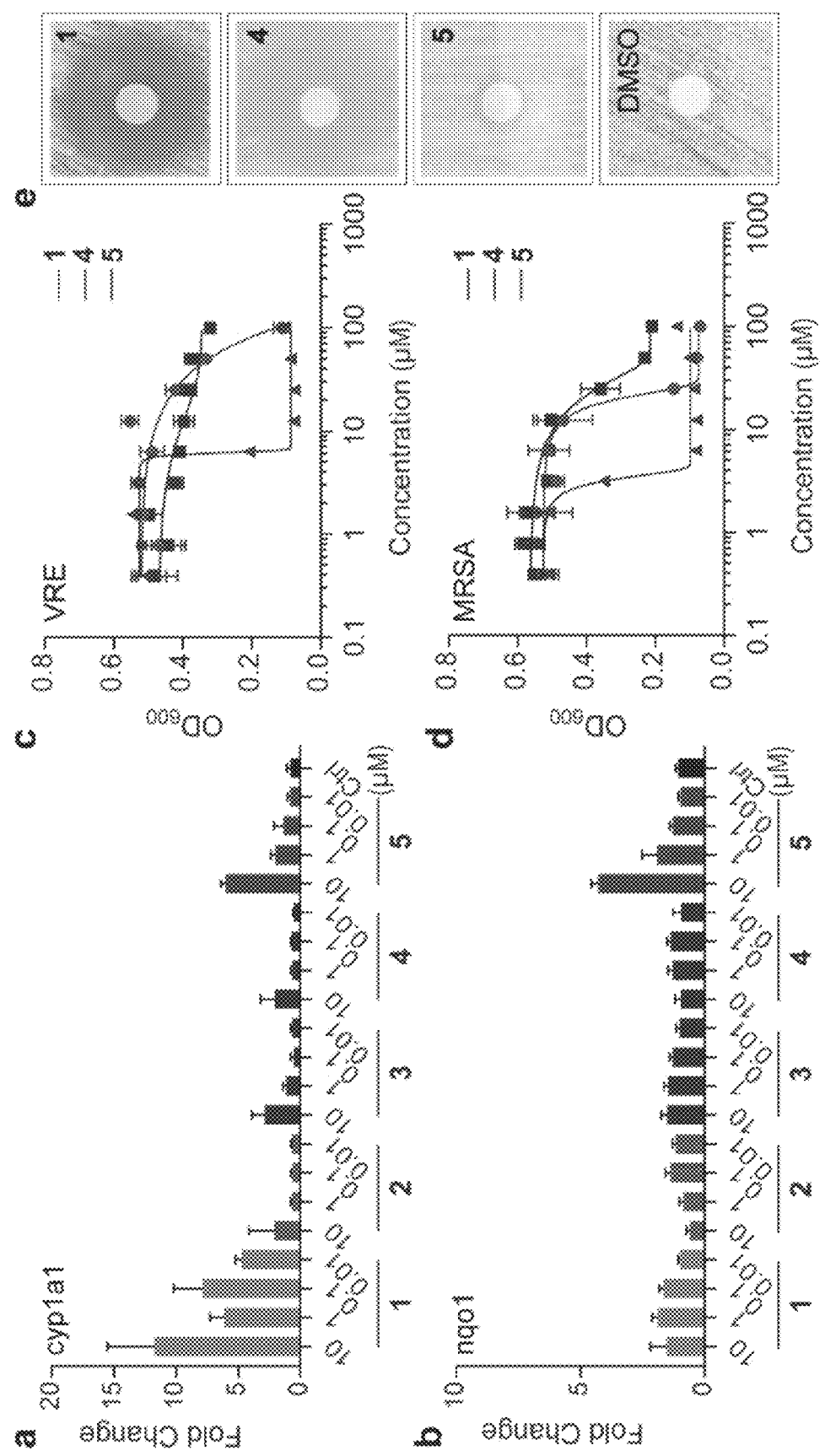
FIGS. 5A and 5B show activation of cyp1a1 and nqo1, respectively, by metabolites in human Hct116 cells. The mean and SD of three biological replicates for each concentration are shown.
FIGS. 5C and 5D show dose-response curves of metabolites against vancomycin-resistant *Enterococcus faecalis* (VRE) and methicillin-resistant *Staphylococcus aureus* (MRSA). The mean and SD of three independent replicates are shown.
FIG. 5E shows the results of a disk diffusion assay to evaluate inhibitory activity of compounds against *Mycobacterium smegmatis* (100 µg compound/disk).
Figures 14A, 14B:
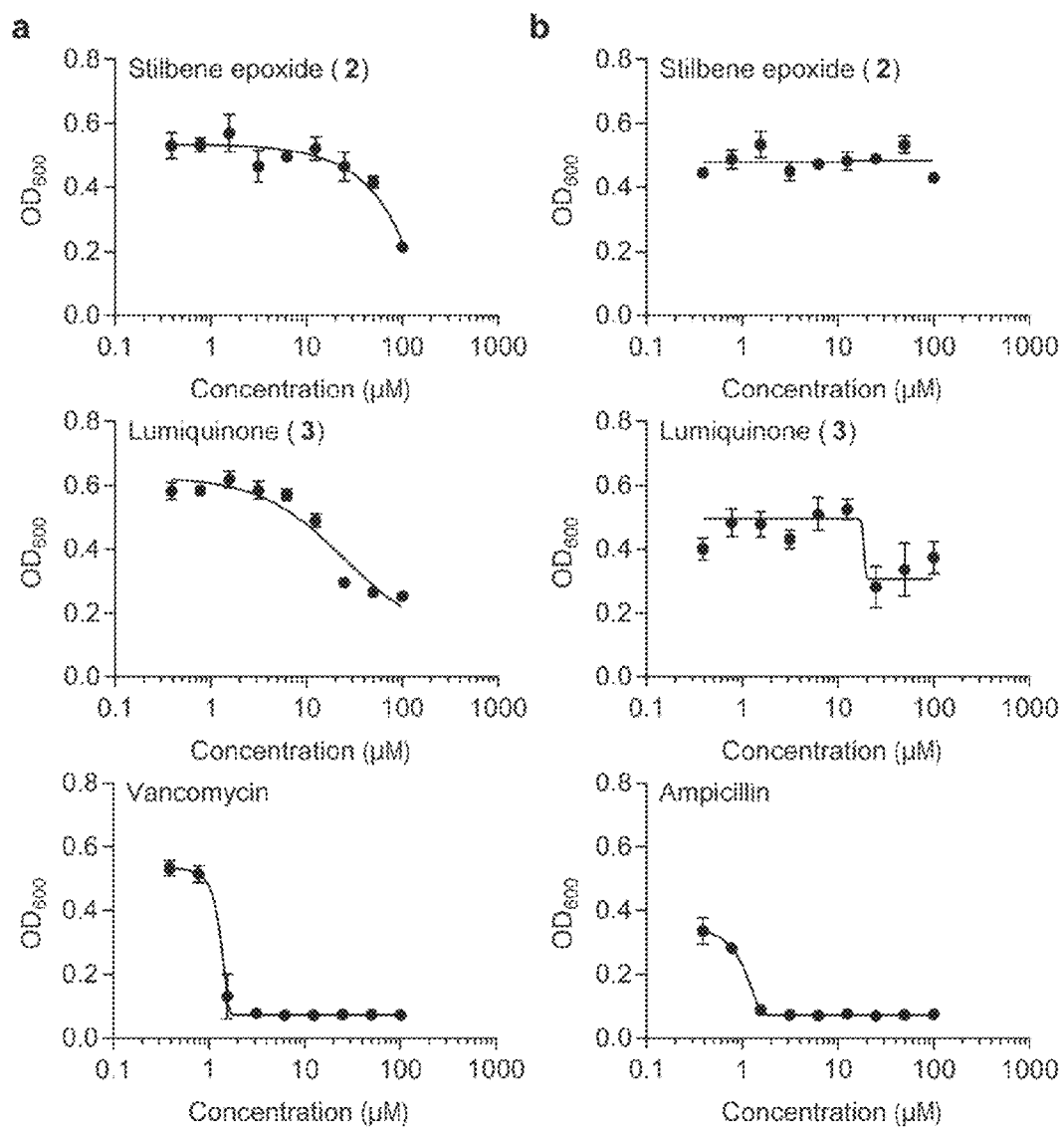
FIGS. 14A and 14B show the growth inhibitory effects of stilbene epoxide (2) and lumiquinone (3) against methicillin-resistant *Staphylococcus aureus* (MRSA, FIG. 14A) and vancomycin-resistant *Enterococcus faecalis* (VRE, FIG. 14B). Vancomycin and ampicillin were used for positive antibiotic controls. Triplicate data is presented with error bars representing the standard deviation.
Figure 15:
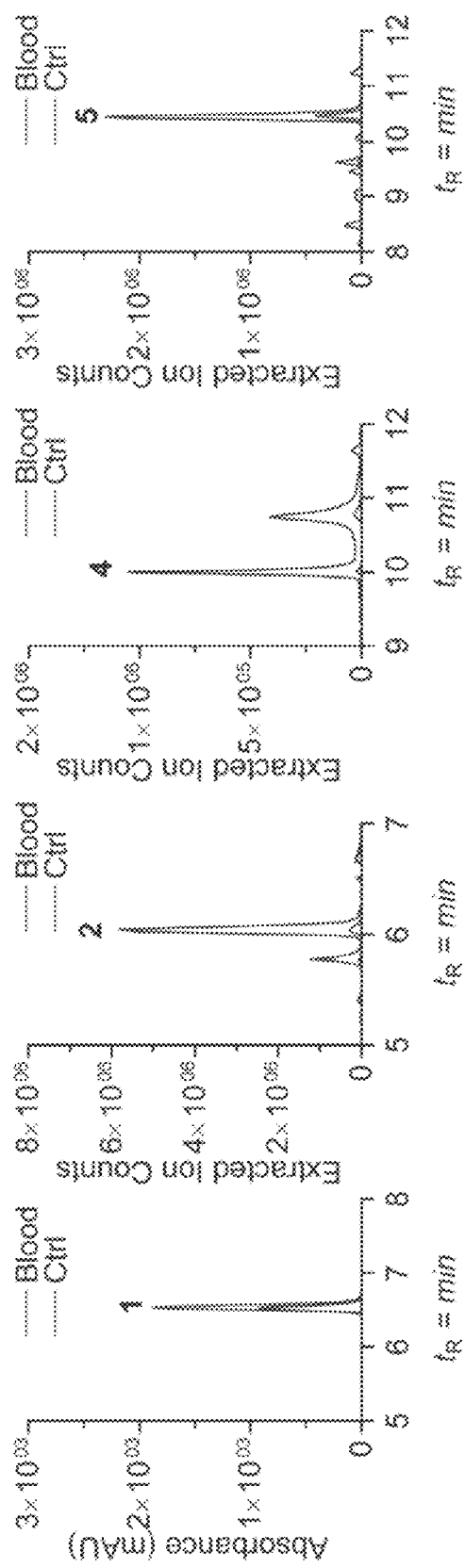
FIG. 15 shows the extracted ion chromatograms for stilebenes 1, 2, 4, and 5 following incubation of 1 on blood agar plates versus water agar plate controls. The molecules could be formed spontaneously over long incubation periods, and blood accelerated the transformations relative to controls. Samples (100 mg $mL^{-1}$) in triplicate were spread on the agar plate and aerobically incubated at 37° C. for 4 h. Whole agar plates were extracted with MeOH and analyzed using a reversed-phase $C_{18}$ HPLC analytical column (Phenomenex Kinetex $C_{18}$ (100 Å) 5 µm (4.6×250 mm) with a linear gradient from 50 to 100% aqueous ACN in 0.1% formic acid over 15 min with a flow rate of 0.7 mL $min^{-1}$.

Tapinarof-Derived Products Activate the Expression of Nrf2 and Exhibit Divergent Antibiosis. To examine if tapinarof analogues and its biotransformation products activate the AhR and Nrf2 signaling pathways, human HCT116 cells were cultured in the presence of 1-5 at varying concentrations. Total RNA was harvested, and qRT-PCR was used to assess relative transcript levels of cyp1a1 and nqo1, genes downstream in the AhR and Nrf2 signaling pathways, respectively. Treatment of cells with 2-5 activated the AhR pathway at 10 µM, which was less active than the parent drug 1 (FIG. 5A). However, tapinarof metabolism product 5 activated the antioxidant Nrf2 signaling pathway gene more robustly than parent drug 1 (FIG. 5B). Because 4 and 5 can be produced enzymatically, in buffers over time, and in blood agar (FIGS. 14A and 14B), these drug metabolism trajectories may contribute to the clinical efficacy of tapinarof.

Tapinarof has previously been shown to weakly inhibit the growth of a panel of microorganisms, including Gram-positive bacteria. Thus, antimicrobial activities of 1-5 were evaluated on two antibiotic-resistant human pathogens, methicillin-resistant *Staphylococcus aureus* (MRSA) and vancomycin-resistant *Enteroroccus faecalis* (VRE) using the minimum inhibitory concentration (MIC) method. The MIC values of tapinarof 1 against these pathogens were 50.5 and 27.0 µM, whereas the MIC values of dimer 5 were considerably more potent at 6.5 µM and 4.1 µM against VRE and MRSA, respectively (FIGS. 5A-5E and FIG. 15). However, activity of 4 was attenuated in these assays, and 2 and 3 similarly showed little to no activity (FIGS. 5A-5E and FIGS. 14A and 14B). The antimycobacterial activities of 1, 4, and 5 were examined. Zone of inhibition analysis using an agar disk diffusion assay with a concentration of 100 µg/disk demonstrated that 4 inhibits the growth of *Mycobacterium smegmatis* at a similar level as 1, whereas 5 was conversely much less active. These data indicate that the metal-dependent cupin bifurcation of 1 to 4 or 5, not only dictates alternative structural paths, but also controls alternative functional outcomes. The much stronger antimicrobial activity of 5 relative to tapinarof could more profoundly alter the microbiome, which is known to be a factor in psoriasis disease severity.

Figure 16:
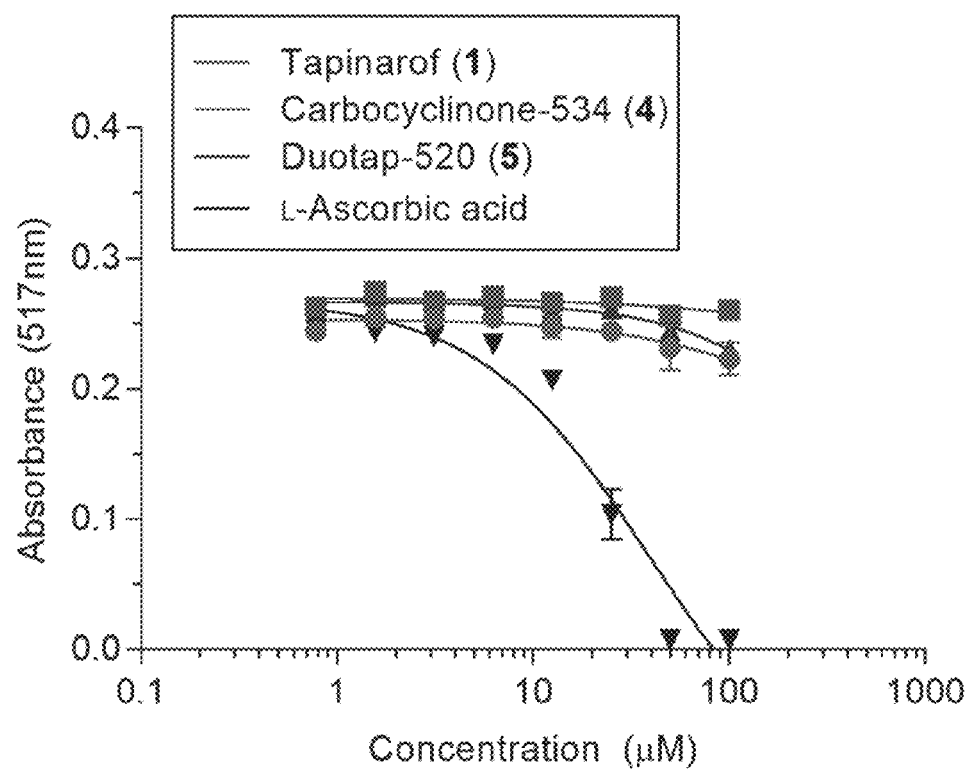
FIG. 16 shows the DPPH radical scavenging assay data of tapinarof (1), carbocyclinone-534 (4), and duotap-520 (5). Triplicate data is presented with error bars representing the standard deviation.
Figure 17:
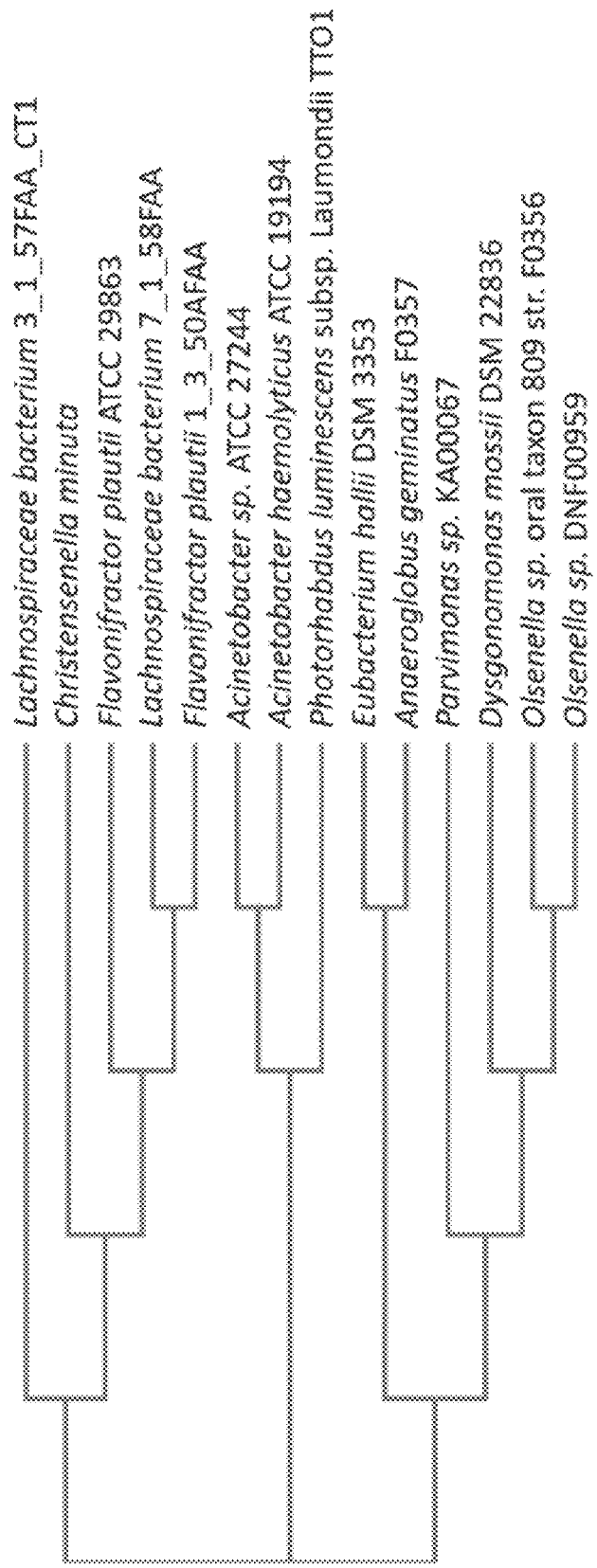
FIG. 17 depicts a phylogenetic tree showing relationship between Plu1886 from *Photorhabdus luminescens* and homologous cupin domain-containing proteins from the human microbiome. Protein sequences were obtained using NCBI BLAST for sequences similar to Plu1886, and results were limited to data from the human microbiome project. The phylogenetic tree was prepared using Clustal Omega at EMBL-EBI.

Pathogens of the skin represent a source of molecules that could serve as leads for the treatment of skin diseases. *P. asymbiotica* causes bloodstream and severe soft tissue infections in humans, including the skin, and all known *Photorhabdus* members produce tapinarof, a phase 3 drug used for the treatment of atopic dermatitis and the autoimmune skin disease psoriasis. Redox stress regulates the differential production of tapinarof and its drug metabolism products—two novel tapinarof dimers 4 and 5. While these products can be formed spontaneously in aerobic conditions over long incubation periods, a conserved cupin-type protein Plu1886 enhances the regioselective dimerization of tapinarof to 4 and 5, depending on redox-active cofactors. Relative to tapinarof, its metabolism product 5 exhibited significantly higher inhibitory activity against multi-drug resistant (MDR) strains, including the common skin pathogen MRSA, whereas product 4 maintained comparable antimycobacterial activity. It was further supported that these products contribute to cellular phenotypes associated with clinical efficacy, including the activation of human AhR and Nrf2 reporter genes. In the cell-based assays, duotap (Compound 1) (5) showed stronger activity than tapinarof in its ability to regulate the Nrf2 antioxidant reporter gene nqo1 (free-radical scavenging activity of 5 was not detected using the 1,3-diphenyl-1-picrylhydrazyl assay with concentrations up to 100 μM), FIG. 16. Similar to the functional drug transformations observed here, the composition of the skin microbiome could be affected by the antimicrobial tapinarof transformation products with Gram-positive (MRSA and VRE) and *Mycobacterial* activities. Conversely, select microbiome members like *P. asymbiotica* could regulate the direction and extent of these transformations, which would be subject to inter-individual microbiome variability. Indeed, homologous cupin domain-containing enzymes were identified in the human microbiome (FIG. 17). Based on the observations, analogous reactions could be expected of dietary stilbenes in the gut, and, in principle, the structures and functions of those metabolism products could underlie the inter-individual variability previously observed for stilbenes in IBD clinical trials. Indeed, Nrf2 activation was recently shown to be protective against IBD symptoms in an ulcerative colitis mouse model. The studies on tapinarof provide a molecular foundation for deciphering the broader functional host-microbe-stilbene metabolic axes in the gut and on the skin.

Methods

High-Resolution LC-MS Metabolite Profiles of *Photorhabdus* Bacteria in Response to Redox Stress. *Photorhabdus luminescens* cultures were grown in 5 mL LB liquid medium triplicates supplemented with methyl viologen dichloride hydrate (0 control, 6.25, and 12.5 μM; 250 rpm aerobic growth at 30° C. for 18 h). The cultures were centrifuged at 2,000×g for 20 min at 4° C. The cleared spent media were extracted with 6 mL ethyl acetate and dried. Crude materials were dissolved in methanol and analyzed by high-resolution ESI-QTOF-MS [column; Phenomenex Kinetex $C_{18}$ (100 Å) 5 μm (4.6×250 mm), flow rate; 0.7 mL min$^{-1}$, mobile phase; a $H_2O$/acetonitrile (MeCN) gradient containing 0.1% formic acid (v/v): 0-30 min, 10-100% ACN; hold for 5 min, 100% ACN; 2 min, 100-10% ACN; 5 min post-time, 10% ACN; instrument: Agilent iFunnel 6550]. Comparative metabolic profiles were achieved by the analyses of UV and LC-MS traces of the stress-induced samples compared to controls. Extracted ion count (EIC) chromatograms were evaluated for the selected redox-stress responsive metabolites with complex chromophores.

Isolation and Characterization of Metabolites. A total of 100 L culture of *P. luminescens* TT01 was cultivated in a LB liquid medium at 30° C. under aerobic conditions with 250 rpm. The culture was centrifuged and the medium was extracted twice with 100 L ethyl acetate (200 L). Drug metabolism products 4 and 5 (Compound 1) were isolated from the crude materials over three rounds of reversed-phase HPLC chromatography, using an Agilent Polaris C18 column, a Phenomenex C18 column, and a Phenyl-Hexyl column. Structures of metabolites were identified as follows: (1) NMR-based structural characterization was achieved by the interpretation of one-dimensional ($^1H$, $^{13}C$, and 1D-NOESY) and two-dimensional [gCOSY, gHSQCAD, gHMBCAD, and 1,1-ADEQUATEAD ($^1J_{CC}$50 Hz)] experiments in methanol-$d_4$. The cyclopropyl-motif and connectivities were further supported by the analyses of LR-HSQMBC and 1,1-ADEQUATEAD ($^1J_{CC}$10 Hz) NMR data. (2) X-ray crystal structure analysis enabled us to confirm the absolute structure of 4 as a racemic mixture. (3) The absolute configuration of the enantiomers of 4 was achieved by optical rotation analysis and comparison to computational and experimental ECD spectra of individual enantiomers, which were purified using chiral-phase super critical fluid chromatography (Lotus Separations, LLC).

Functional analyses of Plu1886 in vitro. Gene plu1886 was PCR-amplified from *P. luminescens* TT01 chromosomal DNA, purified, ligated into pET28a(+)(EMD Bioscience), and cloned into *E. coli* DH10B (Table 5). Positive plu1886 constructs were sequence validated. The gene was introduced into *E. coli* BL21 (DE3) by transformation, expressed, and purified as an N-terminal $His_6$ tagged-variant using Ni-NTA resin. The in vitro enzymatic assays were performed in a total of 100 μL (10 μM enzyme, 1 mM tapinarof, 100 mM sodium phosphate buffer, pH 7.4). Metal ions ($NiCl_2$, $CaCl_2$, $FeSO_4$, $CuSO_4$, $ZnSO_4$, $CoCl_2$, $MgSO_4$, $MnCl_2$) were also individually supplemented at 1 mM. Reactions were incubated at 37° C. overnight (FIG. 3B, 3C, 3E) or 2 h (FIG. 3F), lyophilized, and extracted with MeOH. Enzymatic products were analyzed by single quadrupole LC/MS (Agilent 6120) or high-resolution LC-ESI-QTOF-MS using a Phenomenex Kinetix C18 (100 Å) 5 μm (4.6× 250 mm) column with the following $H_2O$-ACN gradient containing 0.1% formic acid at a flow rate of 0.7 mL min$^{-1}$: 0-30 min 10-100% ACN, 30-35 min 100% ACN, 35-37 min 10% ACN.

Determination of Minimum Inhibitory Concentration. All compounds were freshly dissolved in DMSO at a stock solution of 10 mM. DMSO (solvent vehicle) was used as a negative control and vancomycin and ampicillin were used as positive controls for MRSA and VRE, respectively. Compounds were dispensed into 96-well plates at 100, 50, 25, 12.5, 6.25, 3.13, 1.56, 0.78, and 0.39 μM. Overnight cultures of MRSA grown in tryptic soy broth and VRE grown in brain heart infusion medium were diluted to $OD_{600}$ of 0.1, and 50 μL of fresh cell culture broth was added to each well. The plates were sealed and incubated at 37° C. overnight. Plates were then monitored for $OD_{600}$ using a PerkinElmer Envision 2100 multimode plate reader (PerkinElmer, Waltham, MA, USA).

Disk Diffusion Assay. Growth inhibitory properties of compounds against *Mycobacterium smegmatis* were assessed using the disk diffusion method. A turbid culture of *M. smegmatis* grown in Middlebrook 7H9 liquid medium was diluted to $OD_{600}$=0.1 and streaked on an LB agar plate with a sterile cotton swab. Compounds (10 μL of each sample with a concentration of 100 μg/disk) were added to sterile paper disks (7 mm), and DMSO was used as a negative control. Paper disks soaked with samples were placed on the plate and incubated at 37° C. for 48 h.

AhR and Nrf2 Assay. Hct116 cells were cultured at 37° C. with 5% $CO_2$ in DMEM/F12 medium supplemented with 5% heat-inactivated FBS and 25 mM HEPES. Cells were seeded into 24-well tissue culture plates and grown to 60% confluence. Compounds, diluted in DMSO were then added, ensuring a constant 0.5% DMSO v/v vehicle concentration. Cells were incubated with compounds for 24 hours. Total RNA was then collected with the Qiagen RNeasy Plus Mini Kit. qRT-PCR was performed using the NEB Luna One-Step RT-qPCR kit (E3005) following the standard manufacturer's protocol. Relative transcript levels of cyp1a1 and nqo1 were quantified using the ddCq method, using glyceraldehyde-3-phosphate dehydrogenase (GAPDH) as the reference gene. Melt curve analysis was used to monitor qPCR amplification.

Figure 18:
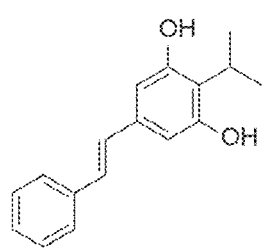
FIG. 18 shows structures of stilbene monomers (1, 6, and 7) and derivatives (5, 8, and 9, corresponding to Compound 1, Compound 3, and Compound 2, respectively).
Figure 18:
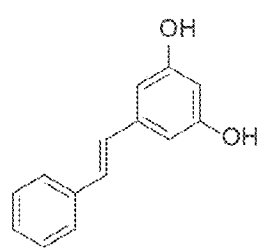
Figure 18:
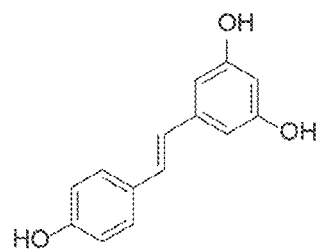
Figure 18:
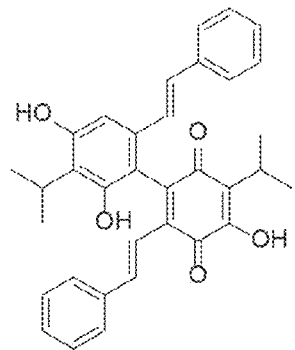
Figure 18:
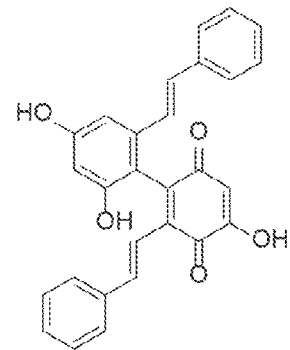
Figure 18:
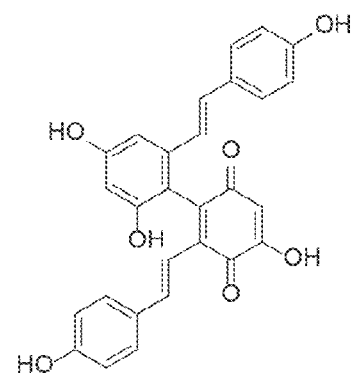

Compounds of Formula I Target the Bacterial Cell Wall Without Selecting for Antibiotic Resistance Photorhabdus stilbene 1 is transformed into dimer 5 through spontaneous oxidation chemistry, enhanced by the cupin enzyme Plu1886. A plant stilbene, pinosylvin (6), can be used as a Plu1886 substrate to make a second derivative of this molecule, duotap-436 (Compound 3) (8). Although resveratrol, another common plant stilbene, did not form a Plu1886-dependent duotap (dimeric) product, it did appear to dimerize spontaneously when incubated in the presence of copper to produce a product that matched the expected duotap dimer by high resolution mass spectrometry ([M+H]$^+$ 469.1297). This spontaneous dimerization product was isolated and confirmed that it was the resveratrol-derived duotap-468 (Compound 2) (9) by 1D and 2D NMR. Notably, the molecule appeared to tautomerize over the course of structural elucidation, but following drying and repetition of $^1$H NMR, it was established that the molecule still showed one set of peaks and was not degrading. Isolation and structural characterization of 6 allowed us to establish a small panel of stilbene monomers and duotap dimers for preliminary structure activity relationship studies (FIG. 18).

Figures 19A, 19B, 19C, 19D, 19E, 19F:
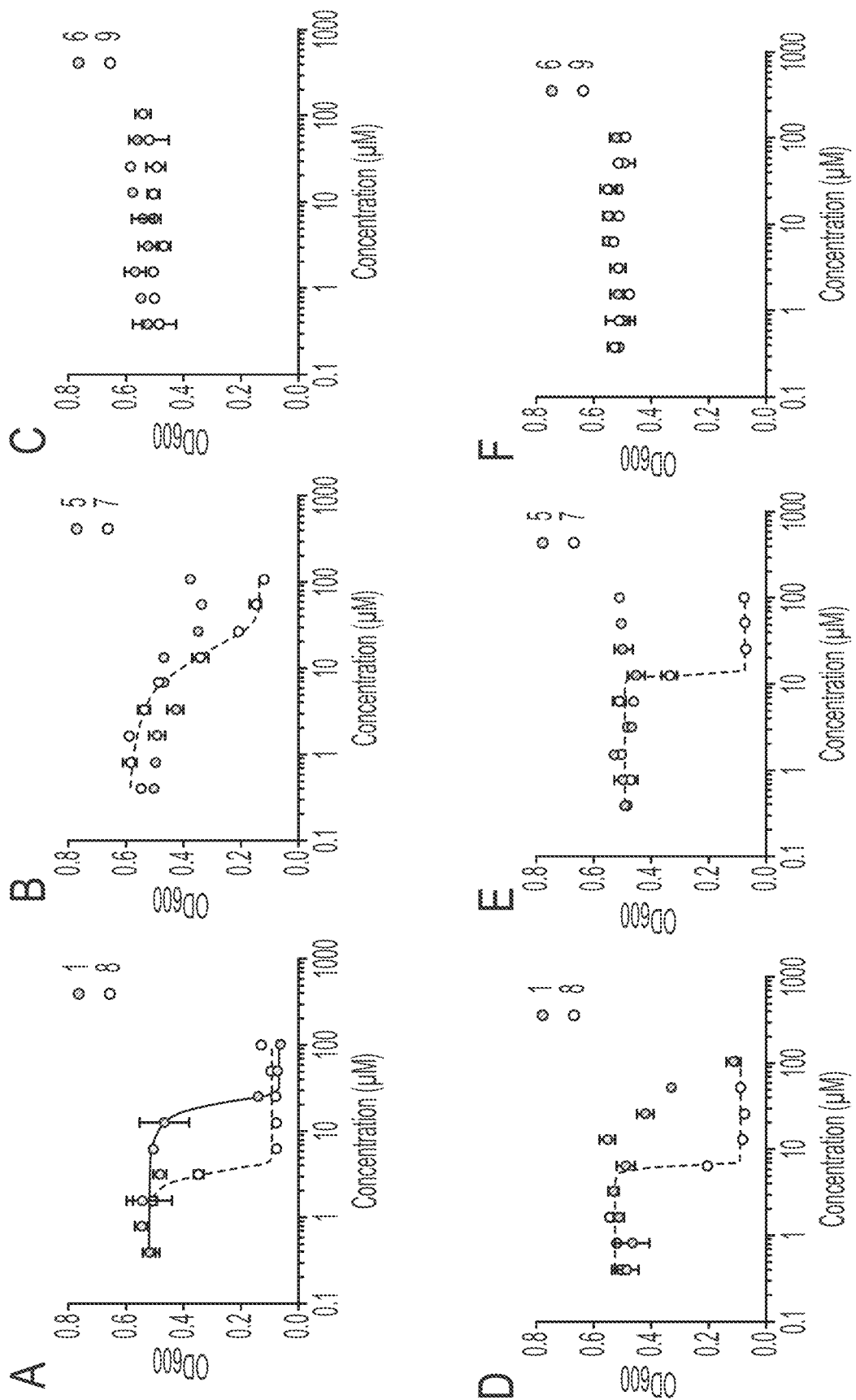
FIGS. 19A-19F show the effects of stilbene monomer to dimer conversion on the minimal inhibitory concentrations of tapinarof (1), Compound 1 (5), pinosylvin (6), Compound 3 (8), resveratrol (7), and Compound 2 (9) against methicillin-resistant *Staphylococcus aureus* (MRSA, FIGS. 19A-19C) and vancomycin-resistant *Enterococcus faecalis* (VRE, FIGS. 19D-19F). Data is represented in triplicate with error bars showing the standard deviation.

The antibiotic activities of this panel of molecules against MRSA (FIG. 19A-C) and VRE (FIGS. 19D-19F). Similar to the functional transformation observed between 1 and 5, 8 displays significantly enhanced antibiotic activity compared to 6, particularly against VRE. On the other hand, 9 showed no enhancement of activity against these pathogens in comparison to 7. Assessment of the relative potencies of this panel of compounds allowed for identification of some initial structure activity relationships for the duotap family of antibiotics, which in various embodiments include compounds of Formula I. Elimination of the isopropyl groups resulted in a slight decrease in antibiotic activity, while substitution of polar hydroxyl groups on the aromatic rings abolished activity against these bacteria at concentrations up to 100 µM (Table 6). In some cases, increasing the polarity of the duotap molecules appears to result in diminished activity. Of note, plant-derived 8 has decently potent activity (6 µg/mL against VRE).

TABLE 6

Minimal inhibitory concentrations (µM) of compounds 1-6 against MRSA and VRE.

| | S. aureus (methicillin resistant) | E. faecalis (vancomycin resistant) |
|---|---|---|
| 1 | 27 | 51 |
| 5 | >100 | >100 |
| 6 | >100 | >100 |
| 8 | 4 | 6 |
| 7 | 25 | 14 |
| 9 | >100 | >100 |

Figure 20A:
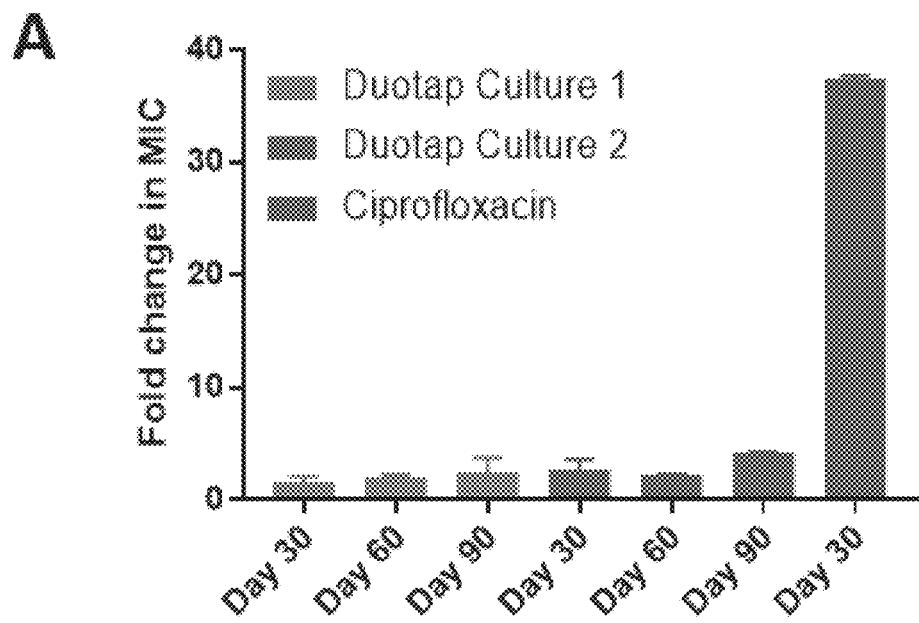
FIGS. 20A-20C show (FIG. 20) fold change in MIC for two independent cultures (Duotap-1 and Duotap-2) grown in the presence of sub-inhibitory levels of duotap-520 after 30, 60, and 90 days. Fold change in MIC for one culture grown in the presence of sub-inhibitory levels of ciprofloxacin for 30 days is shown as a positive control. Error bars represent the standard deviation in three independent measurements of the MIC for each resistant strain.
Figure 20B:
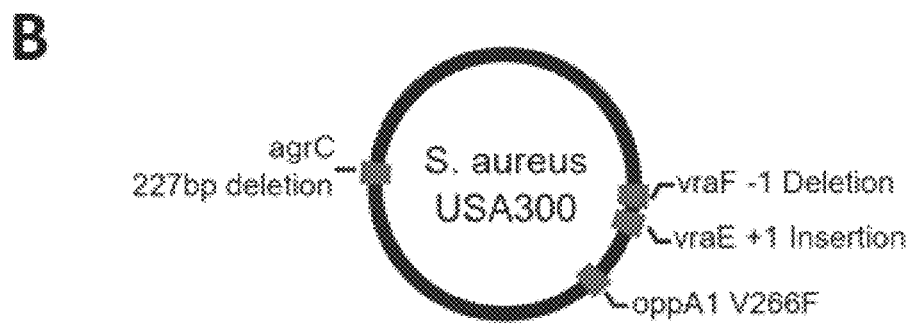
Figure 20C:
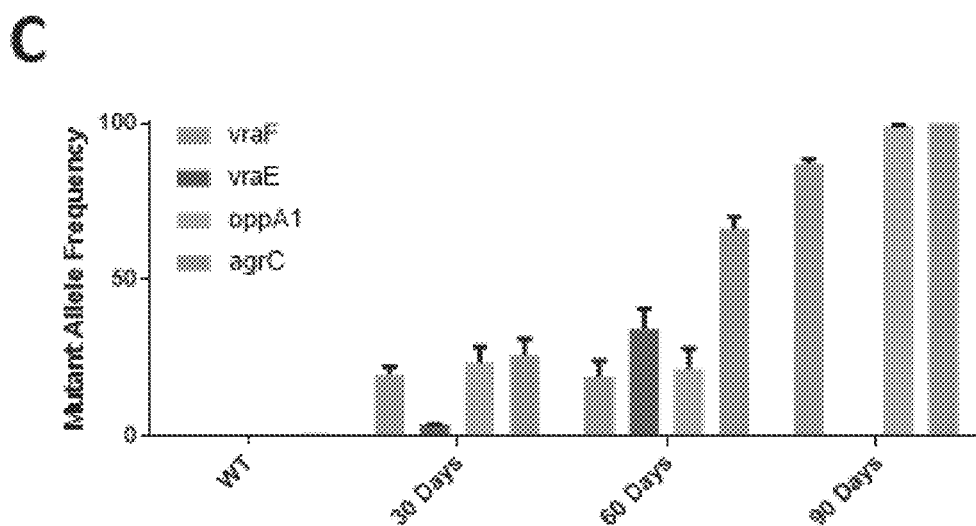
Figure 23A:
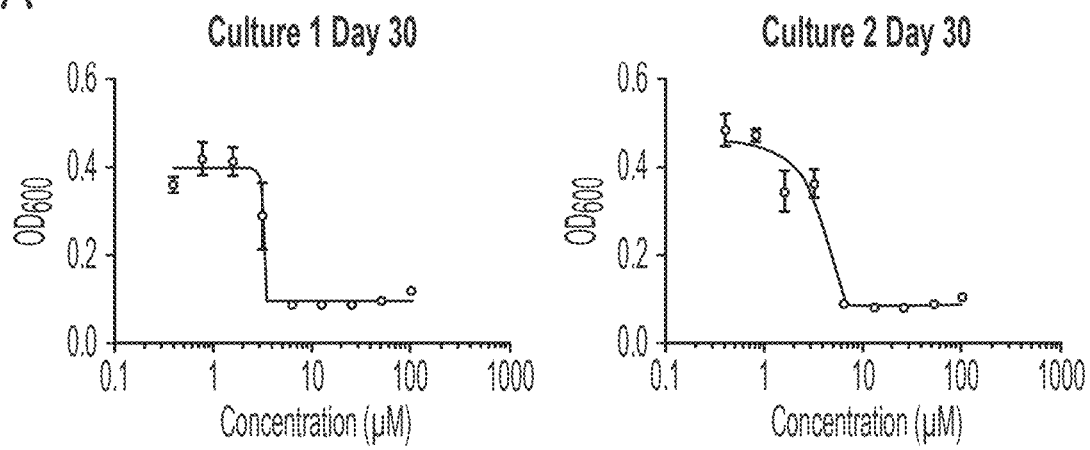
FIGS. 23A-23C show the growth inhibitory effects of duotap-520 against two independent cultures of methicillin-resistant *Staphylococcus aureus* (MRSA) after growth in the presence of sub-inhibitory levels of antibiotic for 30 days (FIG. 23A), 60 days (FIG. 23B), and 90 days (FIG. 23C). Data is represented in triplicate with error bars showing the standard deviation. The MIC for each culture was tested three times, and representative data are shown.
Figure 23B:
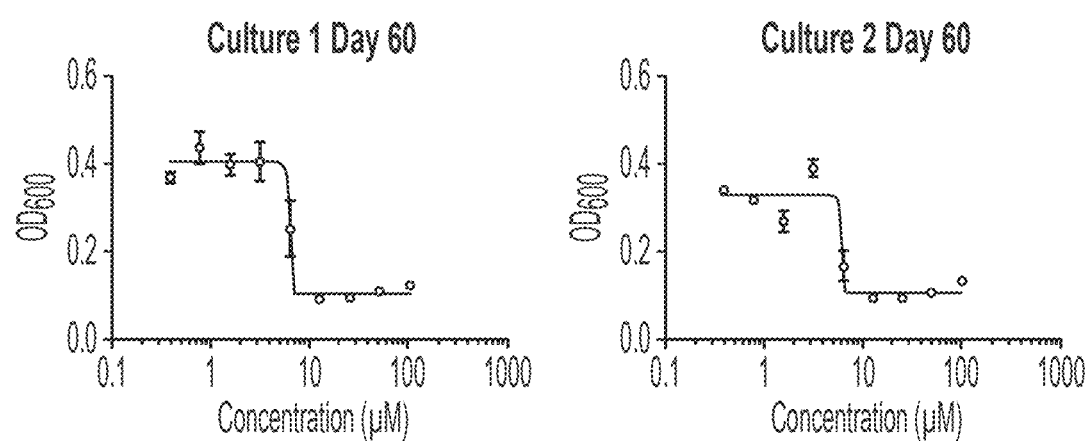
Figure 23C:
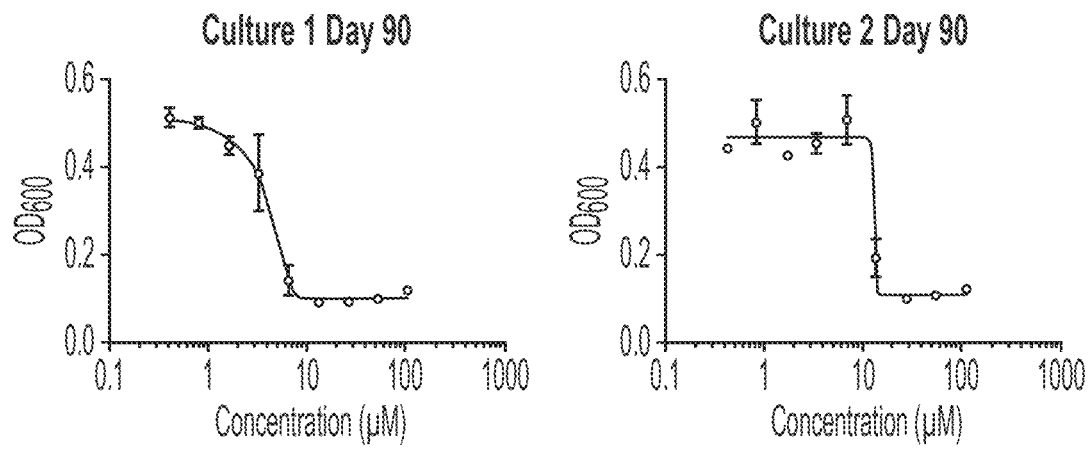

An attempt to culture MRSA mutants resistant to compounds of Formula I was made by subculturing two independent cultures of bacteria continuously in the presence of non-lethal concentrations of 5. After 90 days, only mutants that were approximately 2-fold (culture 1) and 4-fold (culture 2) more resistant were obtained (FIGS. 20A, 23A, and 23C). In contrast, attempts to develop resistance to ciprofloxacin under identical conditions led to resistance mutants with an increase in MIC of approximately 37-fold after only 30 days. To determine the mutations responsible for the slight increase in MIC over 90 days in the duotap-resistant mutants, MRSA populations were analyzed from both cultures at 30, 60, and 90 days by whole genome sequencing. Analysis of the sequencing results primarily revealed mutations in genes previously associated with vancomycin-intermediate S. aureus (VISA) that allow bacteria to synthesize a thicker cell wall (Tables 7-14). Relatively few mutations had accumulated through the 90-day subculture. Of note, frameshifting indels in vraE, vraF, and agrC, as well as a V266F mutation in oppA1 were observed in populations from both cultures (FIG. 20B). All 4 genes have been previously implicated as mechanisms of antibiotic resistance. VraF, oppA1, and agrC mutants gradually increased in frequency within the population throughout the experiment, nearly reaching fixation by 90 days (FIG. 20C). VraE mutants were initially enriched at 60 days but fell out of the population by 90 days.

TABLE 7

Mutations in MRSA at Day 0 of Subculturing

| Position | Base change | Amino acid change | Polymorphism type | Variant frequency | Annotated gene product |
|---|---|---|---|---|---|
| 2,872,915 | T -> C | | SNP | 28.60% | |
| 2,872,914 | A -> C | | SNP | 29.00% | |
| 2,872,914 | A -> G | | SNP | 29.00% | |
| 2,872,912 | TT -> AC | | Substitution | 29.3% -> 32.4% | |
| 1,419,999 | G -> A | V -> I | SNP | 36.50% | M3 family oligoendopeptidase F |
| 512,874 | C -> T | | SNP | 26.60% | |
| 512,643 | A -> G | | SNP | 37.20% | |
| 111,516 | C -> A | Q -> K | SNP | 37.60% | possible staphylococcal tandem lipoprotein |
| 111,512 | A -> G | | SNP | 40.50% | possible staphylococcal tandem lipoprotein |

TABLE 7-continued

Mutations in MRSA at Day 0 of Subculturing

| Position | Base change | Amino acid change | Polymorphism type | Variant frequency | Annotated gene product |
|---|---|---|---|---|---|
| 76,353 | G -> A | | SNP | 43.30% | |
| 76,322 | G -> A | | SNP | 39.80% | |
| 76,295 | T -> C | | SNP | 47.00% | |
| 76,265 | C -> T | | SNP | 28.00% | |
| 36,608 | G -> T | | SNP | 32.50% | |
| 36,581 | C -> T | | SNP | 44.30% | |
| 36,479 | T -> C | T -> A | SNP | 60.10% | IS431mec transposase |
| 36,471 | A -> G | | SNP | 40.40% | IS431mec transposase |
| 36,444 | C -> T | | SNP | 43.90% | IS431mec transposase |
| 36,413 | C -> T | V -> I | SNP | 43.50% | IS431mec transposase |
| 36,315 | G -> A | | SNP | 58.00% | IS431mec transposase |
| 36,269 | C -> T | A -> T | SNP | 57.70% | IS431mec transposase |
| 36,124 | G -> A | A -> V | SNP | 54.10% | IS431mec transposase |
| 35,817 | A -> T | | SNP | 36.30% | |
| 35,816 | A -> C | | SNP | 25.90% | |
| 4 | A -> T | | SNP | 28.60% | |
| 2 | (ACT)2 -> (ACT)3 | | Insertion | 25.00% | |
| 2 | C -> T | | SNP | 75.00% | |
| 1 | A -> T | | SNP | 37.50% | |

TABLE 8

Mutations in MRSA Culture 1 at Day 30 of Subculturing with Compounds of Formula I

| Position | Base change | Amino acid change | Polymorphism type | Variant frequency | Annotated gene product |
|---|---|---|---|---|---|
| 2,872,915 | T -> C | | SNP | 35.00% | |
| 2,872,914 | A -> C | | SNP | 42.90% | |
| 2,872,913 | T -> A | | SNP | 27.30% | |
| 2,872,911 | +TA | | Insertion | 29.40% | |
| 2,872,911 | (T)4 -> (T)5 | | Insertion | 35.30% | |
| 2,872,911 | (T)4 -> (T)5 | | Insertion | 26.50% | |
| 2,149,327 | G -> T | A -> S | SNP | 25.90% | accessory gene regulator protein C |
| 1,419,999 | G -> A | V -> I | SNP | 31.00% | M3 family oligoendopeptidase F |
| 512,643 | A -> G | | SNP | 30.50% | |
| 111,516 | C -> A | Q -> K | SNP | 34.40% | possible staphylococcal tandem lipoprotein |
| 111,512 | A -> G | | SNP | 36.80% | possible staphylococcal tandem lipoprotein |
| 76,353 | G -> A | | SNP | 44.70% | |
| 76,322 | G -> A | | SNP | 44.30% | |
| 76,295 | T -> C | | SNP | 51.20% | |
| 76,265 | C -> T | | SNP | 25.50% | |
| 36,608 | G -> T | | SNP | 30.80% | |
| 36,581 | C -> T | | SNP | 46.40% | |
| 36,479 | T -> C | T -> A | SNP | 53.10% | IS431mec transposase |
| 36,471 | A -> G | | SNP | 35.10% | IS431mec transposase |
| 36,444 | C -> T | | SNP | 39.10% | IS431mec transposase |
| 36,413 | C -> T | V -> I | SNP | 41.50% | IS431mec transposase |
| 36,315 | G -> A | | SNP | 58.50% | IS431mec transposase |

TABLE 8-continued

Mutations in MRSA Culture 1 at Day 30 of Subculturing with Compounds of Formula I

| Position | Base change | Amino acid change | Polymorphism type | Variant frequency | Annotated gene product |
|---|---|---|---|---|---|
| 36,269 | C -> T | A -> T | SNP | 57.50% | IS431mec transposase |
| 36,124 | G -> A | A -> V | SNP | 58.10% | IS431mec transposase |
| 36,087 | A -> G | | SNP | 56.40% | IS431mec transposase |
| 35,816 | A -> C | | SNP | 26.90% | |
| 4 | +ATACTA | | Insertion | 25.00% | |
| 4 | A -> T | | SNP | 25.00% | |
| 2 | (ACT)2 -> (ACT)3 | | Insertion | 42.30% | |
| 2 | C -> A | | SNP | 34.60% | |
| 2 | C -> T | | SNP | 50.00% | |

TABLE 9

Mutations in MRSA Culture 2 at Day 30 of Subculturing with Compounds of Formula I

| Position | Base change | Amino acid change | Polymorphism type | Variant frequency | Annotated gene product |
|---|---|---|---|---|---|
| 2,872,914 | A -> C | | SNP | 33.30% | |
| 2,872,911 | (T)4 -> (T)5 | | Insertion | 29.00% | |
| 2,149,327 | G -> T | A -> S | SNP | 31.80% | accessory gene regulator protein C |
| 1,419,999 | G -> A | V -> I | SNP | 32.00% | M3 family oligoendopeptidase F |
| 992,936 | G -> T | V -> F | SNP | 27.20% | oligopeptide ABC superfamily ATP binding cassette transporter, binding protein |
| 512,643 | A -> G | | SNP | 30.40% | |
| 111,516 | C -> A | Q -> K | SNP | 32.20% | possible staphylococcal tandem lipoprotein |
| 111,512 | A -> G | | SNP | 31.90% | possible staphylococcal tandem lipoprotein |
| 76,353 | G -> A | | SNP | 43.70% | |
| 76,322 | G -> A | | SNP | 40.90% | |
| 76,295 | T -> C | | SNP | 51.10% | |
| 76,265 | C -> T | | SNP | 26.10% | |
| 36,608 | G -> T | | SNP | 29.60% | |
| 36,581 | C -> T | | SNP | 50.70% | |
| 36,479 | T -> C | T -> A | SNP | 60.20% | IS431mec transposase |
| 36,471 | A -> G | | SNP | 35.70% | IS431mec transposase |
| 36,444 | C -> T | | SNP | 42.50% | IS431mec transposase |
| 36,413 | C -> T | V -> I | SNP | 46.80% | IS431mec transposase |
| 36,315 | G -> A | | SNP | 55.40% | IS431mec transposase |
| 36,269 | C -> T | A -> T | SNP | 53.90% | IS431mec transposase |
| 36,124 | G -> A | A -> V | SNP | 59.00% | IS431mec transposase |
| 2 | (ACT)2 -> (ACT)3 | | Insertion | 40.00% | |
| 2 | C -> A | | SNP | 28.00% | |
| 2 | C -> T | | SNP | 28.00% | |
| 1 | A -> T | | SNP | 31.60% | |

TABLE 10

Mutations in MRSA Culture 1 at Day 60 of Subculturing with Compounds of Formula I

| Position | Base change | Amino acid change | Polymorphism type | Variant frequency | Annotated gene product |
|---|---|---|---|---|---|
| 2,872,915 | T -> C | | SNP | 60.00% | |
| 2,872,912 | T -> C | | SNP | 31.40% | |
| 2,149,327 | G -> T | A -> S | SNP | 76.50% | accessory gene regulator protein C |
| 2,149,325 | A -> T | N -> I | SNP | 60.60% | accessory gene regulator protein C |
| 2,149,322 | +T | | Insertion | 33.30% | accessory gene regulator protein C |
| 2,149,319 | T -> G | L -> R | SNP | 42.10% | accessory gene regulator protein C |
| 2,149,317 | T -> A | | SNP | 38.90% | accessory gene regulator protein C |
| 2,149,110 | AAT -> GGC | N -> G | Substitution | 27.6% -> 28.6% | accessory gene regulator protein C |
| 2,149,106 | AA -> TG | | Substitution | 33.3% -> 36.1% | accessory gene regulator protein C |
| 1,274,154 | C -> T | A -> V | SNP | 47.20% | CodY family transcriptional regulator |
| 992,936 | G -> T | V -> F | SNP | 26.20% | oligopeptide ABC superfamily ATP binding cassette transporter, binding protein |
| 736,885 | (A)2 -> (A)3 | | Insertion | 38.90% | ABC superfamily ATP binding cassette transporter, membrane protein (vraE) |
| 512,874 | C -> T | | SNP | 25.30% | |
| 512,643 | A -> G | | SNP | 35.30% | |
| 111,516 | C -> A | Q -> K | SNP | 34.60% | possible staphylococcal tandem lipoprotein |
| 111,512 | A -> G | | SNP | 34.00% | possible staphylococcal tandem lipoprotein |
| 76,353 | G -> A | | SNP | 42.10% | |
| 76,322 | G -> A | | SNP | 39.10% | |
| 76,295 | T -> C | | SNP | 46.50% | |
| 76,265 | C -> T | | SNP | 26.70% | |
| 36,581 | C -> T | | SNP | 47.90% | |
| 36,479 | T -> C | T -> A | SNP | 46.30% | IS431mec transposase |
| 36,471 | A -> G | | SNP | 27.50% | IS431mec transposase |
| 36,413 | C -> T | V -> I | SNP | 41.40% | IS431mec transposase |
| 36,315 | G -> A | | SNP | 53.90% | IS431mec transposase |
| 36,269 | C -> T | A -> T | SNP | 55.10% | IS431mec transposase |
| 36,124 | G -> A | A -> V | SNP | 55.10% | IS431mec transposase |
| 36,087 | A -> G | | SNP | 57.60% | IS431mec transposase |
| 35,817 | A -> T | | SNP | 30.70% | |
| 2 | C -> A | | SNP | 37.50% | |
| 2 | C -> T | | SNP | 41.70% | |
| 2 | (ACT)2 -> (ACT)3 | | Insertion | 50.00% | |
| 1 | A -> T | | SNP | 64.70% | |

TABLE 11

Mutations in MRSA Culture 2 at Day 60 of Subculturing with Compounds of Formula I

| Position | Base change | Amino acid change | Polymorphism type | Variant frequency | Annotated gene product |
|---|---|---|---|---|---|
| 2,872,914 | A -> C | | SNP | 52.20% | |
| 2,872,913 | T -> A | | SNP | 34.60% | |
| 2,872,911 | (T)4 -> (T)5 | | Insertion | 32.10% | |
| 2,872,911 | (T)4 -> (T)5 | | Insertion | 25.00% | |
| 2,872,911 | (T)4 -> (T)5 | | Insertion | 42.90% | |
| 2,872,911 | +AC | | Insertion | 32.10% | |
| 2,149,327 | G -> T | A -> S | SNP | 61.10% | accessory gene regulator protein C |
| 2,149,325 | A -> T | N -> I | SNP | 41.30% | accessory gene regulator protein C |
| 2,149,322 | +T | | Insertion | 29.30% | accessory gene regulator protein C |
| 2,149,319 | T -> G | L -> R | SNP | 36.40% | accessory gene regulator protein C |
| 2,149,110 | T -> C | | SNP | 26.90% | accessory gene regulator protein C |
| 2,149,104 | +GC | | Insertion | 26.20% | accessory gene regulator protein C |
| 1,758,858 | (C)3 -> (C)4 | | Insertion | 34.80% | hypothetical protein |
| 736,885 | (A)2 -> (A)3 | | Insertion | 29.90% | ABC superfamily ATP binding cassette transporter, membrane protein (vraE) |
| 512,874 | C -> T | | SNP | 27.50% | |
| 512,643 | A -> G | | SNP | 31.80% | |
| 156,714 | G -> A | | SNP | 36.60% | transcriptional regulator |
| 111,516 | C -> A | Q -> K | SNP | 32.90% | possible staphylococcal tandem lipoprotein |
| 111,512 | A -> G | | SNP | 34.20% | possible staphylococcal tandem lipoprotein |
| 76,353 | G -> A | | SNP | 43.60% | |
| 76,322 | G -> A | | SNP | 41.20% | |
| 76,295 | T -> C | | SNP | 49.30% | |
| 76,265 | C -> T | | SNP | 25.20% | |
| 36,608 | G -> T | | SNP | 31.30% | |
| 36,581 | C -> T | | SNP | 46.20% | |
| 36,479 | T -> C | T -> A | SNP | 57.70% | IS431mec transposase |
| 36,471 | A -> G | | SNP | 39.20% | IS431mec transposase |
| 36,444 | C -> T | | SNP | 43.00% | IS431mec transposase |
| 36,413 | C -> T | V -> I | SNP | 44.30% | IS431mec transposase |
| 36,315 | G -> A | | SNP | 55.80% | IS431mec transposase |
| 36,269 | C -> T | A -> T | SNP | 53.90% | IS431mec transposase |
| 36,124 | G -> A | A -> V | SNP | 57.80% | IS431mec transposase |
| 36,087 | A -> G | | SNP | 56.60% | IS431mec transposase |
| 2 | C -> A | | SNP | 40.90% | |
| 2 | C -> T | | SNP | 27.30% | |
| 2 | (ACT)2 -> (ACT)3 | | Insertion | 50.00% | |
| 1 | A -> T | | SNP | 64.70% | |

TABLE 12

Mutations in MRSA Culture 1 at Day 90 of Subculturing with Compounds of Formula I

| Position | Base change | Amino acid change | Polymorphism type | Variant frequency | Annotated gene product |
|---|---|---|---|---|---|
| 2,872,915 | T -> C | | SNP | 37.50% | |
| 2,872,914 | A -> C | | SNP | 36.40% | |
| 2,872,911 | (T)4 -> (T)5 | | Insertion | 29.30% | |
| 2,357,993 | -TAATCC | GL -> | Deletion | 28.5% -> 29.1% | DNA-directed RNA polymerase alpha subunit |
| 2,149,327 | G -> T | A -> S | SNP | 100.00% | accessory gene regulator protein C |
| 2,149,325 | A -> T | N -> I | SNP | 72.70% | accessory gene regulator protein C |
| 2,149,324 | A -> T | N -> Y | SNP | 32.40% | accessory gene regulator protein C |
| 2,149,322 | +T | | Insertion | 50.00% | accessory gene regulator protein C |
| 2,149,319 | T -> G | L -> R | SNP | 83.30% | accessory gene regulator protein C |
| 2,149,317 | ATT -> CTA | I -> L | Substitution | 72.7% -> 100.0% | accessory gene regulator protein C |
| 2,149,110 | AAT -> GGC | N -> G | Substitution | 40.9% -> 42.1% | accessory gene regulator protein C |
| 2,149,106 | AA -> TG | | Substitution | 46.2% -> 51.4% | accessory gene regulator protein C |
| 2,149,104 | +GC | | Insertion | 28.20% | accessory gene regulator protein C |
| 2,128,358 | G -> A | | SNP | 25.20% | hypothetical protein |
| 1,759,187 | C -> T | | SNP | 46.70% | |
| 992,936 | G -> T | V -> F | SNP | 99.40% | oligopeptide ABC superfamily ATP binding cassette transporter, binding protein (oppA1) |
| 909,762 | T -> A | | SNP | 26.40% | |
| 909,758 | A -> T | | SNP | 25.30% | |
| 734,971 | (A)7 -> (A)6 | | Deletion | 86.30% | possible ABC superfamily ATP binding cassette transporter, ABC protein (vraF) |
| 512,874 | C -> T | | SNP | 25.80% | |
| 512,643 | A -> G | | SNP | 29.40% | |
| 236,819 | A -> G | I -> V | SNP | 44.10% | oligopeptide ABC superfamily ATP binding cassette transporter, membrane protein |
| 111,516 | C -> A | Q -> K | SNP | 33.60% | possible staphylococcal tandem lipoprotein |
| 111,512 | A -> G | | SNP | 36.60% | possible staphylococcal tandem lipoprotein |
| 76,353 | G -> A | | SNP | 41.10% | |
| 76,322 | G -> A | | SNP | 40.20% | |
| 76,295 | T -> C | | SNP | 49.10% | |
| 76,265 | C -> T | | SNP | 25.20% | |
| 36,581 | C -> T | | SNP | 47.30% | |
| 36,479 | T -> C | T -> A | SNP | 51.20% | IS431mec transposase |
| 36,471 | A -> G | | SNP | 35.80% | IS431mec transposase |
| 36,444 | C -> T | | SNP | 38.70% | IS431mec transposase |
| 36,413 | C -> T | V -> I | SNP | 42.10% | IS431mec transposase |
| 36,315 | G -> A | | SNP | 55.10% | IS431mec transposase |
| 36,269 | C -> T | A -> T | SNP | 56.30% | IS431mec transposase |
| 36,124 | G -> A | A -> V | SNP | 53.90% | IS431mec transposase |
| 36,087 | A -> G | | SNP | 55.00% | IS431mec transposase |

TABLE 12-continued

Mutations in MRSA Culture 1 at Day 90 of Subculturing with Compounds of Formula I

| Position | Base change | Amino acid change | Polymorphism type | Variant frequency | Annotated gene product |
|---|---|---|---|---|---|
| 26,710 | A -> G | I -> V | SNP | 42.70% | sensor histidine kinase VicK |
| 4 | A -> T |  | SNP | 29.70% |  |
| 4 | +ATACTA |  | Insertion | 29.70% |  |
| 2 | C -> A |  | SNP | 42.30% |  |
| 2 | C -> T |  | SNP | 42.30% |  |
| 2 | (ACT)2 -> (ACT)3 |  | Insertion | 38.50% |  |
| 1 | A -> T |  | SNP | 63.20% |  |

TABLE 13

Mutations in MRSA Culture 2 at Day 90 of Subculturing with Compounds of Formula I

| Position | Base change | Amino acid change | Polymorphism type | Variant frequency | Annotated gene product |
|---|---|---|---|---|---|
| 2,872,915 | T -> C |  | SNP | 25.00% |  |
| 2,872,914 | A -> C |  | SNP | 36.00% |  |
| 2,872,911 | (T)4 -> (T)5 |  | Insertion | 30.00% |  |
| 2,692,688 | G -> T | GL -> | SNP | 99.50% |  |
| 2,149,327 | G -> T | A -> S | SNP | 100.00% | accessory gene regulator protein C |
| 2,149,325 | A -> T | N -> 1 | SNP | 73.10% | accessory gene regulator protein C |
| 2,149,324 | A -> T | N -> Y | SNP | 31.80% | accessory gene regulator protein C |
| 2,149,322 | +T |  | Insertion | 65.00% | accessory gene regulator protein C |
| 2,149,319 | T -> G | L -> R | SNP | 87.50% | accessory gene regulator protein C |
| 2,149,317 | ATT -> CTA | I -> L | Substitution | 80.0% -> 100.0% | accessory gene regulator protein C |
| 2,149,110 | AAT -> GGC | N -> G | Substitution | 40.0% -> 44.4% | accessory gene regulator protein C |
| 2,149,106 | AA -> TG |  | Substitution | 57.7% -> 62.1% | accessory gene regulator protein C |
| 2,149,104 | +GC |  | Insertion | 27.60% | accessory gene regulator protein C |
| 1,106,272 | G -> A |  | SNP | 84.90% | dihydrolipoyl dehydrogenase |
| 1,005,832 | -TTTGA |  | Deletion | 64.2% -> 65.4% | possible dithiol-disulfide isomerase |
| 992,936 | G -> T | V -> F | SNP | 99.20% | oligopeptide ABC superfamily ATP binding cassette transporter, binding protein (oppA1) |
| 734,971 | (A)7 -> (A)6 |  | Deletion | 88.10% | possible ABC superfamily ATP binding cassette transporter, ABC protein (vraF) |
| 512,643 | A -> G |  | SNP | 34.30% |  |
| 218,120 | C -> A |  | SNP | 88.40% | possible LIVCS family branched chain amino acid:cation symporter |
| 111,516 | C -> A |  | SNP | 29.70% | possible staphylococcal tandem lipoprotein |
| 111,512 | A -> G |  | SNP | 30.80% | possible staphylococcal tandem lipoprotein |
| 76,353 | G -> A | I -> V | SNP | 45.70% |  |
| 76,322 | G -> A | Q -> K | SNP | 41.30% |  |
| 76,295 | T -> C |  | SNP | 46.30% |  |
| 76,265 | C -> T |  | SNP | 29.30% |  |

TABLE 13-continued

Mutations in MRSA Culture 2 at Day 90 of Subculturing with Compounds of Formula I

| Position | Base change | Amino acid change | Polymorphism type | Variant frequency | Annotated gene product |
|---|---|---|---|---|---|
| 36,581 | C -> T | | SNP | 51.70% | |
| 36,479 | T -> C | | SNP | 55.40% | IS431mec transposase |
| 36,471 | A -> G | | SNP | 34.40% | IS431mec transposase |
| 36,444 | C -> T | | SNP | 40.00% | IS431mec transposase |
| 36,413 | C -> T | T -> A | SNP | 44.90% | IS431mec transposase |
| 36,315 | G -> A | | SNP | 57.50% | IS431mec transposase |
| 36,269 | C -> T | | SNP | 58.40% | IS431mec transposase |
| 36,124 | G -> A | V -> I | SNP | 60.10% | IS431mec transposase |
| 36,087 | A -> G | | SNP | 57.80% | IS431mec transposase |
| 4 | A -> T | A -> T | SNP | 35.70% | |
| 4 | +T | A -> V | Insertion | 25.00% | |
| 4 | -ATACTA | | Insertion | 35.70% | |
| 2 | C -> A | I -> V | SNP | 52.20% | |
| 2 | C -> T | | SNP | 30.40% | |
| 2 | (ACT)2 -> (ACT)3 | | Insertion | 39.10% | |
| 1 | A -> T | | SNP | 50.00% | |

Figures 21A, 21B, 21C, 21D:
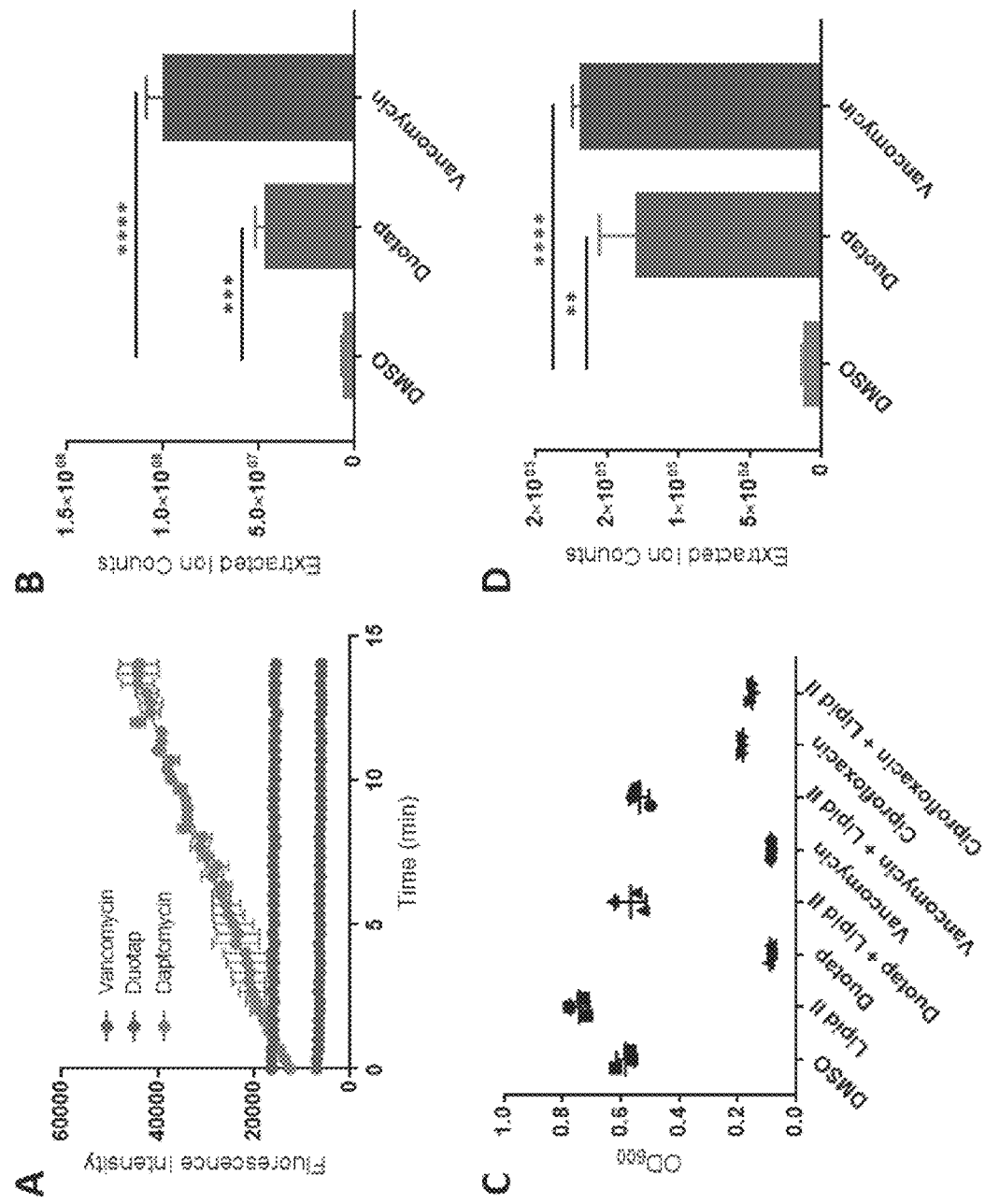
FIGS. 21A-21D show (FIG. 21A) SYTOX Green fluorescence assay for antibiotic-induced bacterial membrane permeability. Vancomycin was used as a negative control, and daptomycin was used as a positive control. Error bars represent the standard error of the mean across 3 biological replicates.
Figures 22A, 22B:
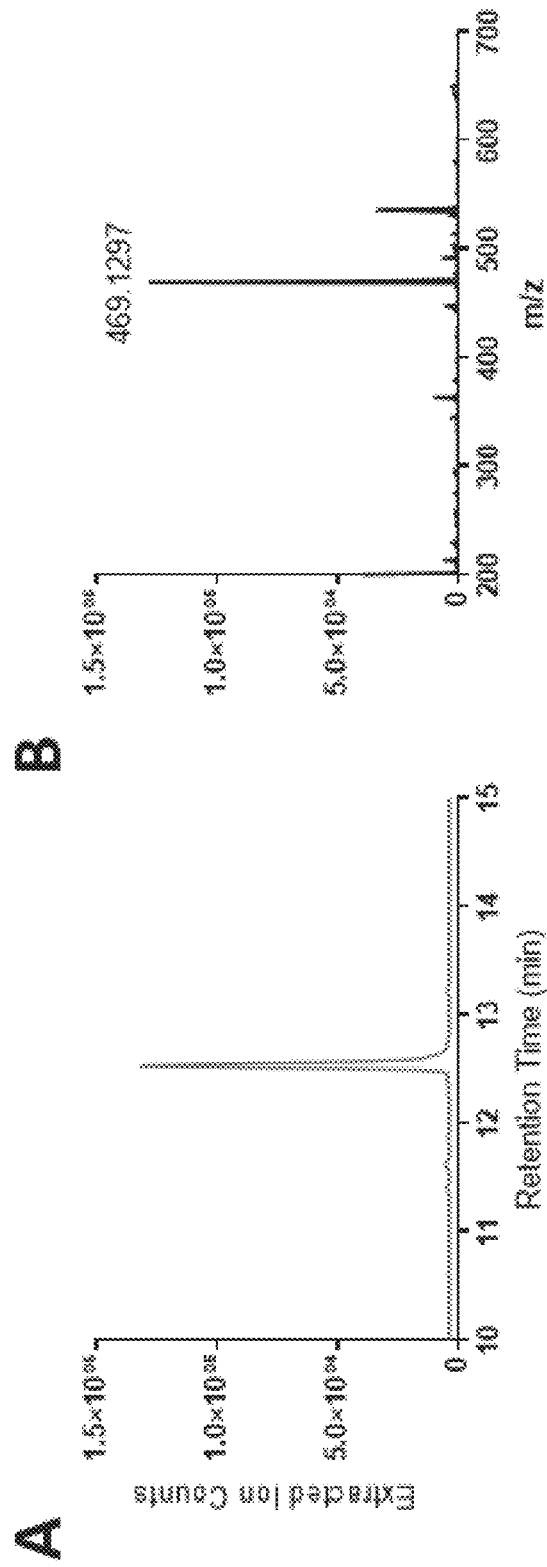
FIGS. 22A-22B illustrate extracted ion chromatogram (EIC) (FIG. 22A) and HR-ESI-QTOF-MS (FIG. 22B) for duotap-468 (Compound 2).

Without being bound by theory, the genome sequencing data suggests that compounds of Formula I can target the bacterial cell wall. This is also consistent with the lack of resistance development observed, as it is more difficult for bacteria to mutate crucial cell wall components compared to other typical antibiotic targets, such as proteins. Teixobactin and malacidin, for example, bind to the cell wall precursor lipid II and do not select for development of resistance under similar experimental conditions. A recently reported class of synthetic retinoid derivatives kill gram positive bacteria by permeabilizing the cell membrane and also do not select for resistance. The effects of compounds of Formula I on the bacterial cell wall were thus investigated. Membrane permeability in MRSA treated with SYTOX Green and showed that compounds of Formula I did not appear to alter the integrity of the bacterial membrane (FIG. 21A). MRSA treated with daptomycin, on the other hand, displayed an increase in membrane permeability, indicating that daptomycin and compounds of Formula I have distinct mechanisms of action. The effects of compounds of Formula I on cell wall biosynthesis was investigated by looking for accumulation of the cell wall precursor molecule UDP-MurNAc-pentapeptide (FIG. 21B). Similar to vancomycin, a significant increase in the level of this precursor in cells treated with compounds of Formula I was observed, suggesting that the target is downstream of this intermediate in cell wall biosynthesis.

Lipid II is a crucial peptidoglycan building block downstream of UDP-MurNAc-pentapeptide and is the target of several antibiotics, including vancomycin. Bacteria were grown in the presence of lethal concentrations of antibiotics with and without supplementation of lipid II into the media. Complementation of lipid II in the presence of compounds of Formula I and vancomycin restored MRSA growth to antibiotic-free levels (FIG. 21C). In contrast, addition of lipid II was not able to rescue bacterial growth in the presence of ciprofloxacin, which is a DNA gyrase inhibitor and does not target the cell wall. Based on these results, and without being bound by theory, the target of compounds of Formula I such as duotap-520 is between the UDP-MurNAc-pentapeptide and lipid II intermediates in cell wall biosynthesis. Because the resistant strains did not contain any mutations in MraY or MurG, the enzymes involved in this portion of the pathway, the binding of compounds of Formula I directly to one of the lipid precursors in the pathway, namely lipid II, undecaprenyl phosphate (C55-P), or undecaprenyl pyrophosphate (C55-PP) was invesitgated. These lipids are the targets of numerous antibiotics. Compounds that bind to lipid II are known to result in its accumulation in cells, while compounds that bind to C55-P or C55-PP result in a reduction in lipid II levels. The effects of compounds of Formula I such as duotap-520 on lipid II pools in bacteria were determined. The lipid tail of lipid II can be removed by boiling in acidic conditions, allowing quantification by LC-MS. Following this protocol, an accumulation of a mass matching de-lipidated lipid II when bacteria were treated with either compounds of Formula I or vancomycin (FIG. 21D) was observed. The identity of this molecule was confirmed by tandem mass spectrometry and compared to published fragmentation data. Without being bound by theory, it is believed that compounds of Formula I target the bacterial cell wall by binding to lipid II and preventing its polymerization and cross-linking into peptidoglycan.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Enumerated Embodiments

The following exemplary embodiments are provided, the numbering of which is not to be construed as designating levels of importance:

Embodiment 1 provides a compound of Formula I, or a salt, solvate, tautomer, enantiomer, or geometric isomer thereof:

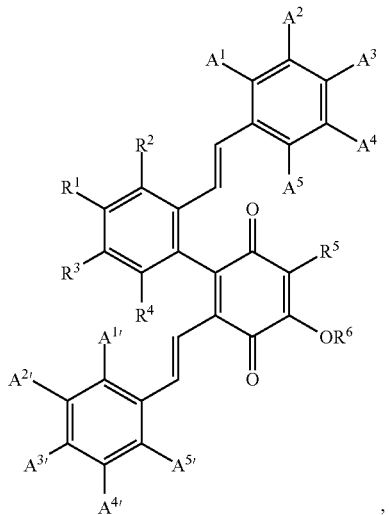

Formula I wherein:
- at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R;
- at each occurrence $R^6$ is independently selected from hydrogen, CF$_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R; and
- at each occurrence R is independently hydrogen, (C$_1$-C$_{100}$)hydrocarbyl, alkyl, acyl, cycloalkyl, aryl, aralkyl, heterocyclyl, heteroaryl, or heteroarylalkyl.

Embodiment 2 provides the compound of embodiment 1, wherein the compound is of Formula II, or a salt, solvate, tautomer, enantiomer, or geometric isomer thereof:

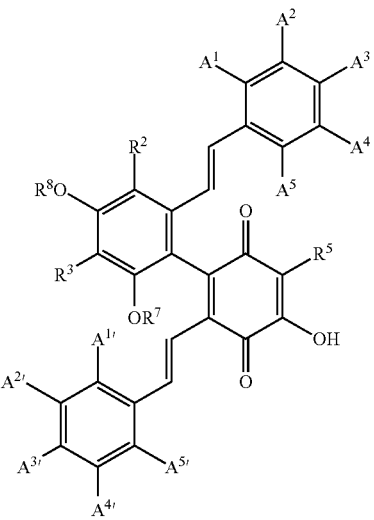

Formula II wherein at each occurrence $R^7$ and $R^8$ are independently selected from hydrogen, CF$_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R.

Embodiment 3 provides the compound of any one of embodiments 1-2, wherein the compound is of Formula III, or a salt, solvate, tautomer, enantiomer, or geometric isomer thereof:

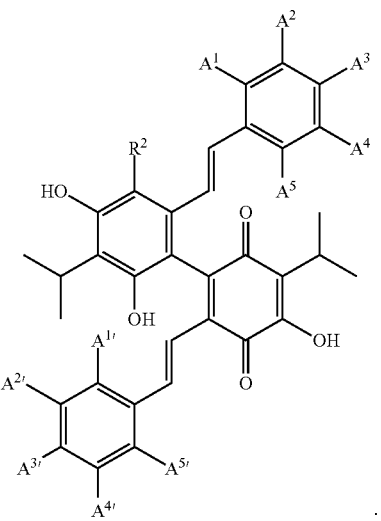

Formula III

Embodiment 4 provides the compound of any one of embodiments 1-3, wherein at least one of $A^1$, $A^2$, $A^3$, $A^4$, $A^5$, $A^{1'}$, $A^{2'}$, $A^{3'}$, $A^{4'}$, and $A^{5'}$ is not hydrogen.

Embodiment 5 provides the compound of any one of embodiments 1-4, wherein $A^1$ and $A^{1'}$ are the same, $A^2$ and $A^{2'}$ are the same, $A^3$ and $A^{3'}$ are the same, $A^4$ and $A^{4'}$ are the same, and $A^5$ and $A^{5'}$ are the same.

Embodiment 6 provides the compound of any one of embodiments 1-5, wherein $A^1$, $A^2$, $A^3$, $A^4$, and $A^5$ are hydrogen.

Embodiment 7 provides the compound of any one of embodiments 1-6, wherein $R^3$ and $R^5$ are iso-propyl.

Embodiment 8 provides the compound of any one of embodiments 1-7, wherein $R^1$ and $R^4$ are OH.

Embodiment 9 provides the compound of any one of embodiments 1-8, wherein $R^3$ and $R^5$ are hydrogen.

Embodiment 10 provides the compound of any one of embodiments 1-9, wherein $A^3$ and $A^{3'}$ are OH.

Embodiment 11 provides the compound of any one of embodiments 1-10, wherein the compound is selected from the group consisting of:

Compound 1

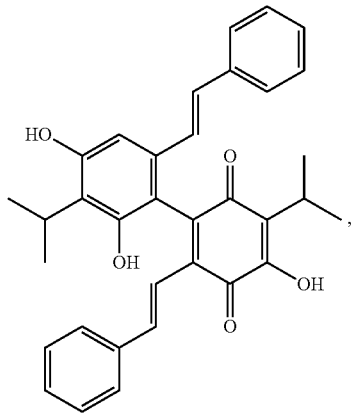

Compound 2

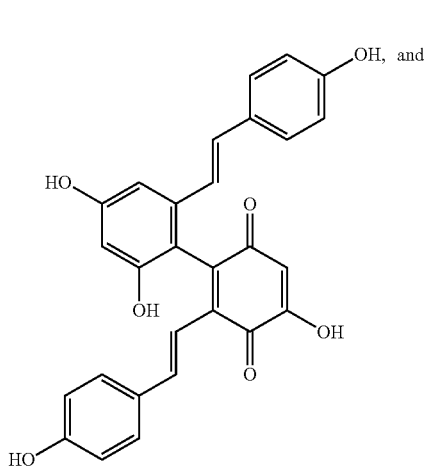

Compound 3

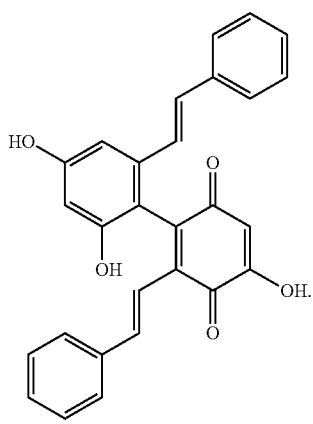

Embodiment 12 provides a pharmaceutical composition comprising the compound of any one of embodiments 1-11, or a salt, solvate, tautomer, enantiomer, or geometric isomer thereof, and at least one pharmaceutically acceptable excipient.

Embodiment 13 provides a method of making a compound of Formula Ia, the method comprising: contacting a compound of Formula IV, or a salt, solvate, tautomer, enantiomer, or geometric isomer thereof:

Formula IV

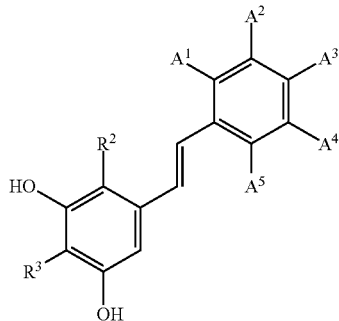

with a medium comprising an organism and at least one metal salt, to produce a compound of Formula Ia, or a salt, solvate, tautomer, enantiomer, or geometric isomer thereof:

Formula Ia

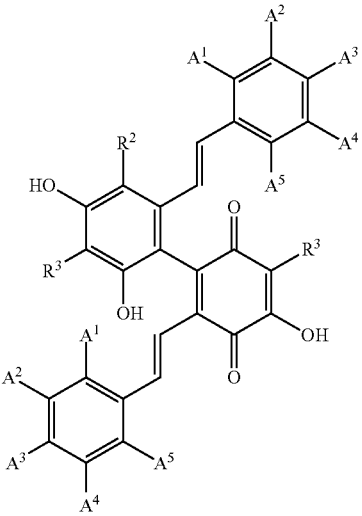

wherein:
at each occurrence $R^2$, $R^3$, $A^1$, $A^2$, $A^3$, $A^4$, and $A^5$, is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R; and
at each occurrence R is independently hydrogen, (C$_1$-C$_{100}$)hydrocarbyl, alkyl, acyl, cycloalkyl, aryl, aralkyl, heterocyclyl, heteroaryl, or heteroarylalkyl.

Embodiment 14 provides the method of embodiment 13, wherein the organism comprises a transformed organism containing a Plu1886 gene.

Embodiment 15 provides the method of any one of embodiments 13-14, wherein the transformed organism is *E. coli* BL21 (DE3).

Embodiment 16 provides the method of any one of embodiments 13-15, wherein the Plu1886 gene is from *P. luminescens*.

Embodiment 17 provides the method of any one of embodiments 13-16, wherein the metal salt is a salt of Li, Na, K, Cs, Mg, Ca, Sr, Ba, Sc, Ti, V, Cr, Mn, Fe, Co, Ni, Cu, Zn, Zr, Ru, Rh, Pd, Ag, W, Re, Os, Ir, Pt, or Au.

Embodiment 18 provides the method of any one of embodiments 13-17, wherein the salt is a chloride, bromide, iodide, fluoride, sulfate ($SO_4^{2-}$), phosphate ($PO_4^{2-}$), nitrate, or carbonate.

Embodiment 19 provides the method of any one of embodiments 13-18, wherein the metal salt is at least one salt selected from $NiCl_2$, $CaCl_2$, $FeSO_4$, $CuSO_4$, $ZnSO_4$, $CoCl_2$, $MgSO_4$, or $MnCl_2$.

Embodiment 20 provides the method of any one of embodiments 13-19, wherein the medium comprises a buffer.

Embodiment 21 provides the method of any one of embodiments 13-20, wherein the medium comprises a gastrointestinal tract of a subject, the organism comprises a bacterial population (microbiome) in the subject, and the metal salt comprises a metal salt in the gastrointestinal tract of the subject.

Embodiment 22 provides a method of killing or disinfecting bacteria, the method comprising contacting a bacterial population with a compound of Formula I, or a salt, solvate, tautomer, enantiomer, or geometric isomer thereof:

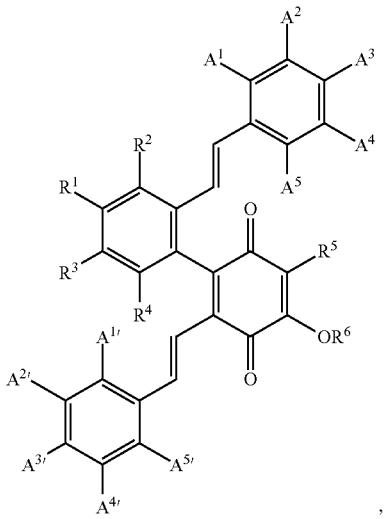

Formula I wherein:
at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, $NO_2$, $ONO_2$, azido, $CF_3$, $OCF_3$, R, methylenedioxy, ethylenedioxy, N(R)$_2$, SR, SOR, $SO_2$R, $SO_2$N(R)$_2$, $SO_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R;

at each occurrence $R^6$ is independently selected from hydrogen, $CF_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R;

at each occurrence R is independently hydrogen, ($C_1$-$C_{100}$)hydrocarbyl, alkyl, acyl, cycloalkyl, aryl, aralkyl, heterocyclyl, heteroaryl, or heteroarylalkyl; and wherein the bacterial population is killed or disinfected after coming into contact with the compound of Formula I.

Embodiment 23 provides the method of embodiment 22, wherein the bacterial population comprises a pathogenic bacterial population that is pathogenic in a mammal.

Embodiment 24 provides the method of any one of embodiments 22-23, wherein the bacterial population comprises at least one bacterial genus selected from *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia*.

Embodiment 25 provides the method of any one of embodiments 22-24, wherein the bacterial population comprises methicillin-resistant *Staphylococcus aureus* (MRSA), vancomycin-resistant *Enterococcus faecalis* (VRE), or a combination thereof.

Embodiment 26 provides the method of any one of embodiments 22-25, wherein the compound kills or disinfects at least about 95% of the bacterial population.

Embodiment 27 provides the method of any one of embodiments 22-26, wherein the compound has a minimum inhibitory concentration (MIC) of about 0.5 µM to about 50 µM.

Embodiment 28 provides the method of any one of embodiments 22-27, wherein the compound has a MIC of about 1 µM to about 10 µM toward MRSA or VRE.

Embodiment 29 provides the method of any one of embodiments 22-28, wherein the bacterial population does not develop resistance after exposure to the compound for a prolonged period.

Embodiment 30 provides the method of any one of embodiments 22-29, wherein the prolonged period is at least about 1 week.

Embodiment 31 provides the method of any one of embodiments 22-30, wherein the bacterial population is killed at least about 95% as effectively after coming into contact with the compound for the prolonged period as compared to a percentage of a similar bacterial population killed after first coming into contact with the compound.

Embodiment 32 provides the method of any one of embodiments 22-31, wherein the bacterial population is present on or in a non-living object.

Embodiment 33 provides the method of any one of embodiments 22-32, wherein the non-living object comprises metals, ceramics, glass, wood, fabrics, rubber, plastic, polymers, composite materials made from any combination of the foregoing, and/or any combinations thereof.

Embodiment 34 provides the method of any one of embodiments 22-33, wherein the compound kills or disinfects at least about 95% of the bacterial population on the non-living object.

Embodiment 35 provides a method of treating a bacterial infection in a subject, the method comprising administering to the subject a therapeutically effective amount of a composition comprising at least one pharmaceutically acceptable excipient and a compound of Formula I, or a salt, solvate, tautomer, enantiomer, or geometric isomer thereof:

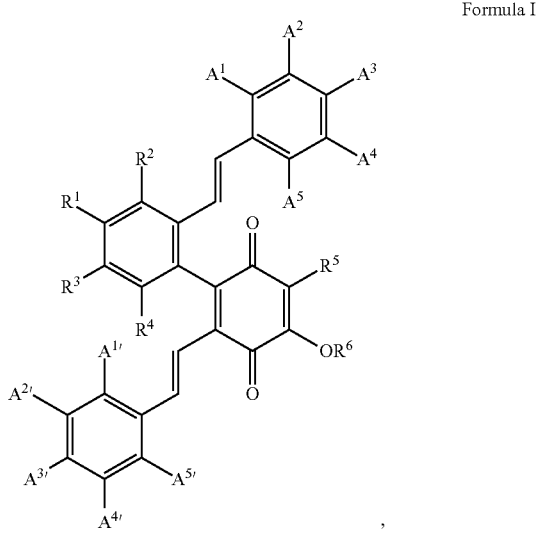

Formula I wherein:
at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R;

at each occurrence $R^6$ is independently selected from hydrogen, CF$_3$, R, methylenedioxy, ethylenedioxy, OR, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R; and at each occurrence R is independently hydrogen, (C$_1$-C$_{100}$)hydrocarbyl, alkyl, acyl, cycloalkyl, aryl, aralkyl, heterocyclyl, heteroaryl, or heteroarylalkyl.

Embodiment 36 provides the method of embodiment 35, wherein the bacterial infection comprises bacterial vaginosis, bacterial meningitis I, bacterial pneumonia, bacterial upper respiratory infections, ear infections, eye infections, skin infections, thrush, urinary tract infection, bacterial gastroenteritis, impetigo, erysipelas, and/or cellulitis.

Embodiment 37 provides the method of any one of embodiments 35-36, wherein the subject is a human.

Embodiment 38 provides the method of any one of embodiments 35-37, wherein the administering is by an administration route selected from oral, transdermal, transmucosal, nasal, rectal, intravesical, intrapulmonary, intraduodenal, intragastrical, intrathecal, subcutaneous, intramuscular, intradermal, intra-arterial, intravenous, intrabronchial, inhalation, and topical.

Embodiment 39 provides a method of treating or ameliorating psoriasis or atopic dermatitis, the method comprising: contacting the skin of a subject with a composition comprising 0.0001 to 10% (w/w) of the compound of any one of claims 1-12.

Embodiment 40 provides the method of embodiment 39, wherein the composition is a topical or transdermal composition.

Embodiment 41 provides the method of any one of embodiments 39-40, wherein the composition comprises at least one other active agent.

Embodiment 42 provides the method of any one of embodiments 39-41, wherein the at least one other agent is an anti-inflammatory agent, an analgesic agent, or an antimicrobial agent.

Embodiment 43 provides the method of any one of embodiments 39-42, wherein the compositions comprises at least one pharmaceutically or cosmetically acceptable excipient.

Embodiment 44 provides the method of any one of embodiments 39-43, wherein the subject is human.

What is claimed is:

1. A compound of Formula I, or a salt, solvate, tautomer, enantiomer, or geometric isomer thereof:

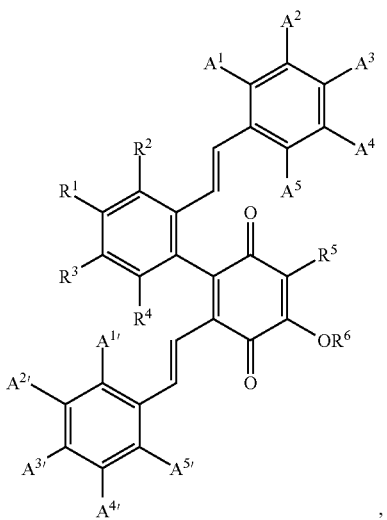

Formula I wherein:
at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R;

at each occurrence $R^6$ is independently selected from hydrogen, CF$_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R; and at each occurrence R is independently hydrogen, (C$_1$-C$_{100}$) hydrocarbyl, alkyl, acyl, cycloalkyl, aryl, aralkyl, heterocyclyl, heteroaryl, or heteroarylalkyl.

2. The compound of claim 1, wherein the compound is of Formula II, or a salt, solvate, tautomer, enantiomer, or geometric isomer thereof:

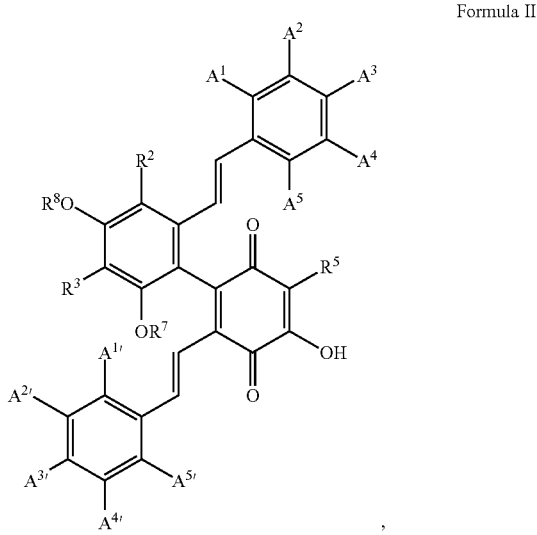

Formula II wherein at each occurrence $R^7$ and $R^8$ are independently selected from hydrogen, $CF_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R.

3. The compound of claim 1, wherein the compound is of Formula III, or a salt, solvate, tautomer, enantiomer, or geometric isomer thereof:

Formula III

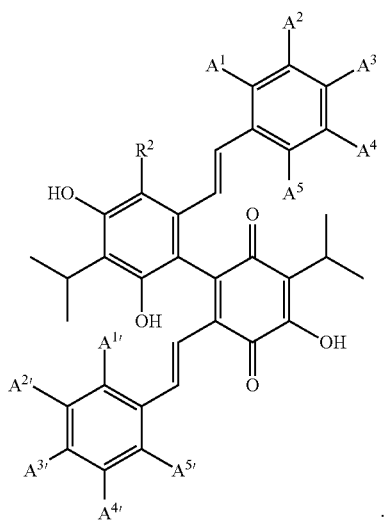

4. The compound of claim 3, wherein at least one of $A^1$, $A^2$, $A^3$, $A^4$, $A^5$, $A^{1'}$, $A^{2'}$, $A^{3'}$, $A^{4'}$, and $A^{5'}$ is not hydrogen.

5. The compound of claim 1, wherein $A^1$ and $A^{1'}$ are the same, $A^2$ and $A^{2'}$ are the same, $A^3$ and $A^{3'}$ are the same, $A^4$ and $A^{4'}$ are the same, and $A^5$ and $A^{5'}$ are the same.

6. The compound of claim 1, wherein at least one of the following applies:
$A^1$, $A^2$, $A^3$, $A^4$, and $A^5$ are hydrogen;
$R^3$ and $R^5$ are isopropyl;
$R^1$ and $R^4$ are OH;
$R^3$ and $R^5$ are hydrogen;
$A^3$ and $A^{3'}$ are OH.

7. The compound of claim 1, which is selected from the group consisting of:

Compound 1

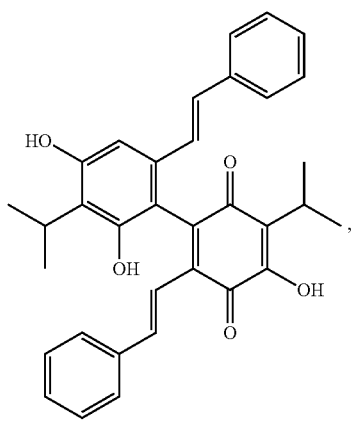

Compound 2

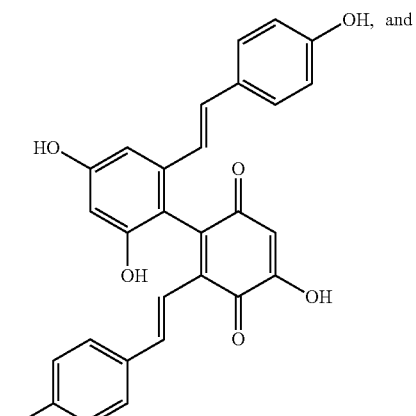

Compound 3

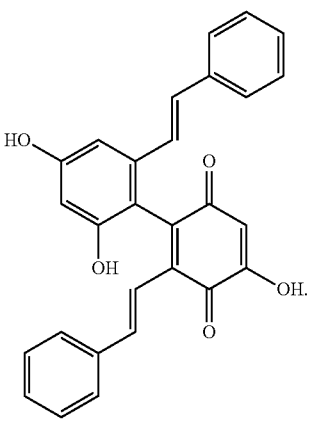

8. A pharmaceutical composition comprising the compound of claim 1, or a salt, solvate, tautomer, enantiomer, or geometric isomer thereof, and at least one pharmaceutically acceptable excipient.

9. A method of making a compound of Formula Ia, the method comprising:
contacting a compound of Formula IV, or a salt, solvate, tautomer, enantiomer, or geometric isomer thereof:

Formula IV

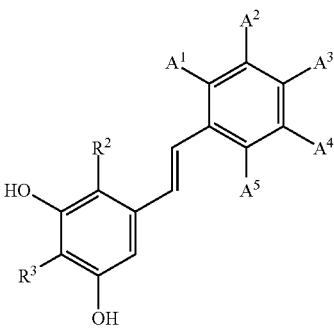

with a medium comprising an organism and at least one metal salt, to yield a compound of Formula Ia, or a salt, solvate, tautomer, enantiomer, or geometric isomer thereof:

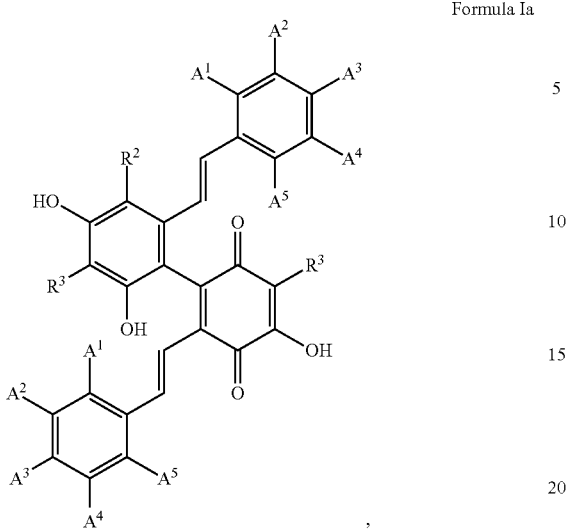

Formula Ia

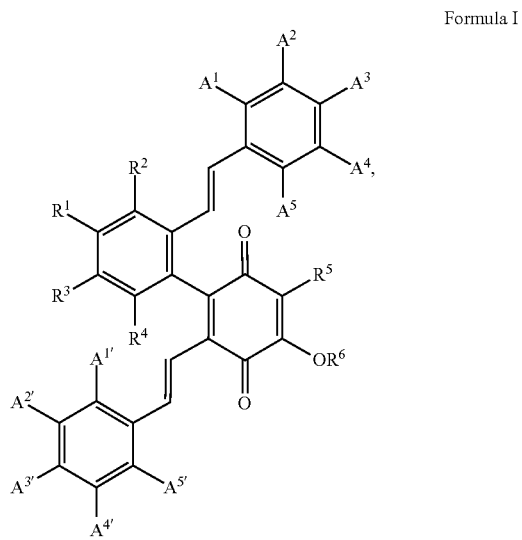

Formula I wherein:
at each occurrence $R^2$, $R^3$, $A^1$, $A^2$, $A^3$, $A^4$, and $A^5$, is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R; and
at each occurrence R is independently hydrogen, (C$_1$-C$_{100}$) hydrocarbyl, alkyl, acyl, cycloalkyl, aryl, aralkyl, heterocyclyl, heteroaryl, or heteroarylalkyl.

10. The method of claim 9, wherein the organism comprises a transformed organism containing a Plu1886 gene.

11. The method of claim 10, wherein at least one of the following applies:
the transformed organism is *E. coli* BL21 (DE3);
the Plu1886 gene is from *P. luminescens*.

12. The method of claim 9, wherein at least one of the following applies:
the metal salt is a salt of Li, Na, K, Cs, Mg, Ca, Sr, Ba, Sc, Ti, V, Cr, Mn, Fe, Co, Ni, Cu, Zn, Zr, Ru, Rh, Pd, Ag, W, Re, Os, Ir, Pt, or Au;
the salt is a chloride, bromide, iodide, fluoride, sulfate (SO$_4{}^{2-}$), phosphate (PO$_4{}^{2-}$), nitrate, or carbonate;
the metal salt is at least one salt selected from NiCl$_2$, CaCl$_2$, FeSO$_4$, CuSO$_4$, ZnSO$_4$, CoCl$_2$, MgSO$_4$, or MnCl$_2$.

13. The method of claim 9, wherein the medium comprises
(a) a buffer, or
(b) a gastrointestinal tract of a subject, wherein the organism comprises a bacterial population in the subject, and wherein the metal salt comprises a metal salt in the gastrointestinal tract of the subject.

14. A method of killing or disinfecting bacteria, the method comprising:
contacting a bacterial population with a compound of Formula I, or a salt, solvate, tautomer, enantiomer, or geometric isomer thereof:

wherein:
at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R;
at each occurrence $R^6$ is independently selected from hydrogen, CF$_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R; and
at each occurrence R is independently hydrogen, (C$_1$-C$_{100}$) hydrocarbyl, alkyl, acyl, cycloalkyl, aryl, aralkyl, heterocyclyl, heteroaryl, or heteroarylalkyl;
wherein the bacterial population is killed or disinfected after coming into contact with the compound of Formula I, or salt, solvate, tautomer, enantiomer, or geometric isomer thereof.

15. The method of claim 14, wherein the bacterial population comprises a pathogenic bacterial population that is pathogenic in a mammal.

16. The method of claim 14, wherein at least one the following applies:
the bacterial population comprises at least one bacterial genus selected from *Bacillus, Bartonella, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio*, and *Yersinia*;
the bacterial population comprises methicillin-resistant *Staphylococcus aureus* (MRSA), vancomycin-resistant *Enterococcus faecalis* (VRE), or a combination thereof.

17. The method of claim 14, wherein at least one of the following applies:
the compound kills or disinfects at least about 95% of the bacterial population;
the compound has a minimum inhibitory concentration (MIC) of about 0.5 μM to about 50 μM;
the compound has a MIC of about 1 μM to about 10 μM toward MRSA or VRE;
the bacterial population does not develop resistance after exposure to the compound for a prolonged period, optionally wherein the prolonged period is at least about 1 week;
the bacterial population is killed at least about 95% as effectively after coming into contact with the compound for the prolonged period as compared to a percentage of a similar bacterial population killed after first coming into contact with the compound;
the bacterial population is present on or in a non-living object.

18. The method of claim 17, wherein at least one applies:
the non-living object comprises metals, ceramics, glass, wood, fabrics, rubber, plastic, polymers, composite materials made from any combination of the foregoing, or any combinations thereof;
the compound kills or disinfects at least about 95% of the bacterial population on the non-living object.

19. A method of treating a bacterial infection in a subject, the method comprising:
administering to the subject a therapeutically effective amount of a composition comprising at least one pharmaceutically acceptable excipient and a compound of Formula I, or a salt, solvate, tautomer, enantiomer, or geometric isomer thereof:

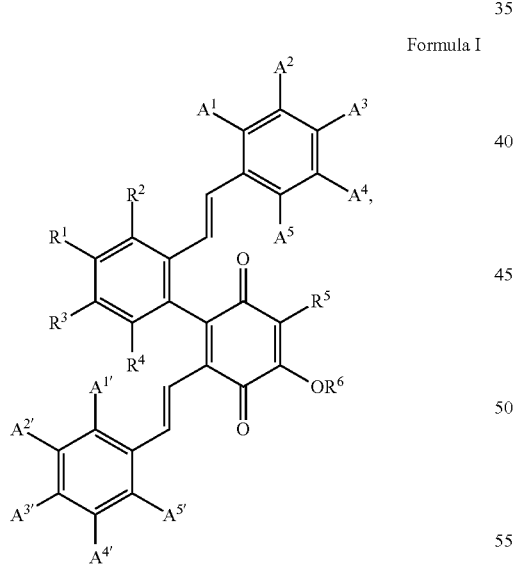

Formula I wherein:
at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R;
at each occurrence $R^6$ is independently selected from hydrogen, CF$_3$, R, methylenedioxy, ethylenedioxy, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{1-2}$N(R)C(O)R, (CH$_2$)$_{1-2}$N(R)N(R)$_2$, C(=NH)N(R)$_2$, C(O)N(OR)R, and C(=NOR)R; and
at each occurrence R is independently hydrogen, alkyl, acyl, cycloalkyl, aryl, aralkyl, heterocyclyl, heteroaryl, or heteroarylalkyl.

20. The method of claim 19, wherein at least one of the following applies:
the bacterial infection comprises bacterial vaginosis, bacterial meningitis I, bacterial pneumonia, bacterial upper respiratory infections, ear infections, eye infections, skin infections, thrush, urinary tract infection, bacterial gastroenteritis, impetigo, erysipelas, or cellulitis;
the administering is by an administration route selected from oral, transdermal, transmucosal, nasal, rectal, intravesical, intrapulmonary, intraduodenal, intragastrical, intrathecal, subcutaneous, intramuscular, intradermal, intra-arterial, intravenous, intrabronchial, inhalation, and topical.

21. A method of treating or ameliorating psoriasis or atopic dermatitis, the method comprising:
contacting the skin of a subject with a composition comprising the compound of Formula I, or a salt, solvate, tautomer, enantiomer, or geometric isomer thereof:

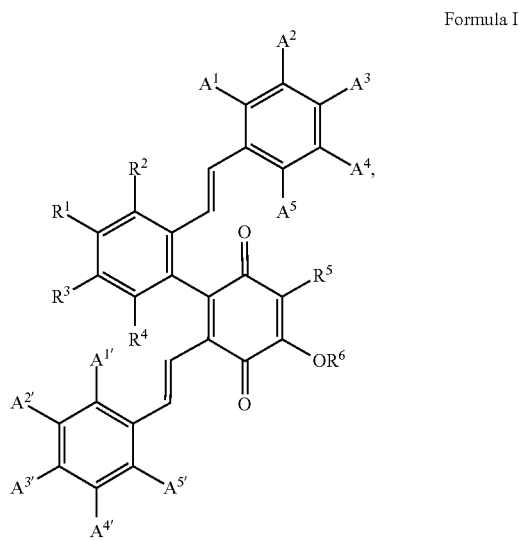

Formula I wherein:
at each occurrence $R^1$, $R^2$, $R^3$, $R^4$, $R^5$, $A^1$, $A^2$, $A^3$, $A^4$, $A^5$, $A^{1'}$, $A^{2'}$, $A^{3'}$, $A^{4'}$, and $A^{5'}$ is independently selected from hydrogen, F, Cl, Br, I, OR, OC(O)N(R)$_2$, CN, NO, NO$_2$, ONO$_2$, azido, CF$_3$, OCF$_3$, R, methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N $(R)_2$, $N(R)C(O)OR$, $N(R)C(O)R$, $N(R)C(S)R$, $N(R)C(O)N(R)_2$, $N(R)C(S)N(R)_2$, $N(COR)COR$, $N(OR)R$, $C(=NH)N(R)_2$, $C(O)N(OR)R$, and $C(=NOR)R$;

at each occurrence $R^6$ is independently selected from hydrogen, $CF_3$, R, methylenedioxy, ethylenedioxy, $C(O)R$, $C(O)C(O)R$, $C(O)CH_2C(O)R$, $C(S)R$, $C(O)OR$, $OC(O)R$, $C(O)N(R)_2$, $OC(O)N(R)_2$, $C(S)N(R)_2$, $(CH_2)_{1-2}N(R)C(O)R$, $(CH_2)_{1-2}N(R)N(R)_2$, $C(=NH)N(R)_2$, $C(O)N(OR)R$, and $C(=NOR)R$; and at each occurrence R is independently hydrogen, alkyl, acyl, cycloalkyl, aryl, aralkyl, heterocyclyl, heteroaryl, or heteroarylalkyl.

22. The method of claim 21, wherein at least one of the following applies:

the composition is a topical or transdermal composition;

the composition comprises at least one other active agent, optionally wherein the at least one other agent is an anti-inflammatory agent, an analgesic agent, or an anti-microbial agent;

the composition comprises at least one pharmaceutically or cosmetically acceptable excipient;

the composition comprises 0.0001 to 10% (w/w) of the compound.

23. The method of claim 13, wherein the bacterial population comprises at least a fraction of the subject's microbiome.

* * * * *

SEQUENCE LISTING

```
<160> NUMBER OF SEQ ID NOS: 3

<210> SEQ ID NO 1
<211> LENGTH: 423
<212> TYPE: DNA
<213> ORGANISM: Photorhabdus luminescens

<400> SEQUENCE: 1
atggaattta ttaaaaatag attttgtcac tggaacggtg aacaccttgt tgtcgataca      60
atggccagaa atcataaaat ggttaacagt atgggaacgg gcgagggatt agtttcgttt     120
gatggctttg gtgctgatct aattcgtttc agcaaagatg aggggatgca gaatcatact     180
cacttagggc atcatatctt atttgtcctc gcaggaacgg gttatgttat ttatgcgggt     240
```

-continued

```
gaaaagcata aaatagagcc tggagtttgt tattttgtga atggagaaat agatcacgcg      300
attaaagcaa ccagcgattt ggttatgctt gttgtcggta ataatcattg tgcggttgat      360
gcgcaagata ggacgacgct ggtgccatat agagagggaa cgccagagga attaaaggtt      420
taa                                                                    423

<210> SEQ ID NO 2
<211> LENGTH: 47
<212> TYPE: DNA
<213> ORGANISM: Artificial Sequence
<220> FEATURE:
<223> OTHER INFORMATION: Recombinant

<400> SEQUENCE: 2
gaattccata tggaatttat taaaaataga ttttgtcact ggaacgg                    47

<210> SEQ ID NO 3
<211> LENGTH: 40
<212> TYPE: DNA
<213> ORGANISM: Artificial Sequence
<220> FEATURE:
<223> OTHER INFORMATION: Recombinant

<400> SEQUENCE: 3
gaattcaagc ttttaaacct ttaattcctc tggcgttccc                            40
```